United States Patent
Wood et al.

(10) Patent No.: US 8,002,711 B2
(45) Date of Patent: Aug. 23, 2011

(54) METHODS AND DEVICES FOR RELIEVING STRESS

(75) Inventors: Michael Wood, Miami Beach, FL (US); Adam Forbes, New York, NY (US); Kirstin Rhys, Brooklyn, NY (US)

(73) Assignee: Respironics, Inc., Murrsyville, PA (US)

( * ) Notice: Subject to any disclaimer, the term of this patent is extended or adjusted under 35 U.S.C. 154(b) by 993 days.

(21) Appl. No.: 11/408,682

(22) Filed: Apr. 20, 2006

(65) Prior Publication Data

US 2007/0056582 A1 Mar. 15, 2007

Related U.S. Application Data

(63) Continuation-in-part of application No. 11/084,456, filed on Mar. 18, 2005, now Pat. No. 7,691,049.

(60) Provisional application No. 60/673,148, filed on Apr. 20, 2005, provisional application No. 60/673,627, filed on Apr. 21, 2005, provisional application No. 60/705,883, filed on Aug. 4, 2005.

(51) Int. Cl.
*A61B 5/08* (2006.01)
(52) U.S. Cl. .......................... 600/529; 600/26; 600/515
(58) Field of Classification Search .................. 600/26, 600/515
See application file for complete search history.

(56) References Cited

U.S. PATENT DOCUMENTS

| | | | |
|---|---|---|---|
| 4,510,944 A | 4/1985 | Porges | |
| 4,519,395 A | 5/1985 | Hrushesky | |
| 4,960,129 A | 10/1990 | dePaola et al. | |
| 5,148,812 A | 9/1992 | Verrier et al. | |
| 5,265,617 A | 11/1993 | Verrier et al. | |
| 5,277,189 A | 1/1994 | Jacobs | |
| 5,291,400 A | 3/1994 | Gilham | |
| 5,423,325 A | 6/1995 | Burton | |
| 5,520,192 A | 5/1996 | Kitney et al. | |
| 5,579,775 A | 12/1996 | Dempsey et al. | |
| 5,603,331 A | 2/1997 | Heemels et al. | |
| 5,682,901 A | 11/1997 | Kamen | |
| 5,687,734 A | 11/1997 | Dempsey et al. | |
| 5,718,235 A | 2/1998 | Golosarsky et al. | |
| 5,807,247 A | 9/1998 | Merchant et al. | |
| 5,853,364 A | 12/1998 | Baker et al. | |
| 5,891,044 A | 4/1999 | Golosarsky et al. | |
| 5,997,482 A * | 12/1999 | Vaschillo et al. | 600/484 |
| 6,002,952 A | 12/1999 | Diab et al. | |
| 6,026,320 A | 2/2000 | Carlson et al. | |
| 6,083,172 A | 7/2000 | Baker et al. | |
| 6,099,481 A | 8/2000 | Daniels et al. | |
| 6,106,481 A | 8/2000 | Cohen | |
| 6,144,877 A | 11/2000 | DePetrillo | |
| 6,179,784 B1 | 1/2001 | Daniels et al. | |
| 6,212,427 B1 | 4/2001 | Hoover | |
| 6,269,263 B1 | 7/2001 | Ohnishi et al. | |
| 6,305,943 B1 | 10/2001 | Pougatchev et al. | |
| 6,358,201 B1 | 3/2002 | Childre et al. | |
| 6,411,833 B1 | 6/2002 | Baker, Jr. et al. | |
| 6,416,473 B1 | 7/2002 | Risk et al. | |

(Continued)

*Primary Examiner* — Carl H Layno
*Assistant Examiner* — Natasha N Patel

(57) ABSTRACT

Easy to use, cost-effective methods and devices for evaluating and treating stress and thereby disorders caused or exacerbated by stress are provided. More particularly methods and devices for identifying RSA waves during respiration which provide a subject with real-time RSA wave information are provided. These methods and devices also can be used to identify drop points in RSA waves. Such methods and devices provide subjects with the ability to maintain parasympathetic outflow and thereby prevent and/or reduce levels of stress.

17 Claims, 90 Drawing Sheets

BOTTOM LEVEL ($bp_n$) = 1

U.S. PATENT DOCUMENTS

| | | |
|---|---|---|
| 6,487,442 B1 | 11/2002 | Wood |
| 6,490,480 B1 | 12/2002 | Lerner |
| 6,529,772 B2 | 3/2003 | Carlson et al. |
| 6,532,382 B2 | 3/2003 | Meier et al. |
| 6,539,249 B1 | 3/2003 | Kadhiresan et al. |
| 6,572,558 B2 | 6/2003 | Masakov et al. |
| 6,626,843 B2 * | 9/2003 | Hillsman ............... 600/529 |
| 6,656,116 B2 * | 12/2003 | Kim et al. ............... 600/300 |
| 6,658,276 B2 | 12/2003 | Kianl et al. |
| 6,678,547 B2 | 1/2004 | Carlson et al. |
| 6,699,194 B1 | 3/2004 | Diab et al. |
| 6,702,752 B2 | 3/2004 | Dekker |
| 6,731,974 B2 | 5/2004 | Levitan et al. |
| 6,805,673 B2 | 10/2004 | Dekker |
| 6,836,681 B2 | 12/2004 | Stabler et al. |
| 6,850,788 B2 | 2/2005 | Al-Ali |
| 2002/0045806 A1 | 4/2002 | Baker et al. |
| 2002/0111555 A1 | 8/2002 | Stabler et al. |
| 2002/0137994 A1 | 9/2002 | Baker et al. |
| 2002/0161291 A1 | 10/2002 | Kianl et al. |
| 2003/0018357 A1 | 1/2003 | Luthra et al. |
| 2003/0045807 A1 | 3/2003 | Daniels et al. |
| 2003/0078505 A1 | 4/2003 | Kim et al. |
| 2003/0163034 A1 | 8/2003 | Dekker |
| 2003/0163050 A1 | 8/2003 | Dekker |
| 2003/0163054 A1 | 8/2003 | Dekker |
| 2003/0181798 A1 | 9/2003 | Al-Ali |
| 2004/0019289 A1 | 1/2004 | Ross |
| 2004/0122486 A1 * | 6/2004 | Stahmann et al. ............... 607/60 |
| 2004/0122487 A1 | 6/2004 | Hatelsad et al. |
| 2004/0127804 A1 | 7/2004 | Hatelsad et al. |
| 2004/0181134 A1 | 9/2004 | Baker et al. |
| 2004/0230104 A1 | 11/2004 | Yanagidaira et al. |
| 2004/0230252 A1 | 11/2004 | Kullok et al. |
| 2004/0236236 A1 | 11/2004 | Yanagidaria et al. |
| 2004/0249299 A1 | 12/2004 | Cobb |
| 2004/0260186 A1 | 12/2004 | Dekker |
| 2005/0021092 A1 | 1/2005 | Yun et al. |
| 2005/0033189 A1 | 2/2005 | McCraty et al. |

* cited by examiner $p\text{-}p_0 = \text{abs}(p_1 - p_0) = \text{abs}(1{,}010\text{ ms} - 10\text{ ms}) = 1{,}000\text{ ms}$ $p\text{-}p_1 = \text{abs}(p_2 - p_1) = \text{abs}(1{,}860\text{ ms} - 1{,}010\text{ms}) = 850\text{ ms}$ $p\text{-}p_2 = \text{abs}(p_3 - p_2) = \text{abs}(2{,}560\text{ ms} - 1{,}860\text{ms}) = 700\text{ ms}$ $p\text{-}p_0 = abs\,(p_1\text{-}p_0) = abs\,(1{,}010\ ms - 10\ ms) = 1{,}000\ ms$ $p\text{-}p_1 = abs\,(p_2\text{-}p_1) = abs\,(1{,}860\ ms - 1{,}010 ms) = 850\ ms$ $p\text{-}p_2 = abs\,(p_3\text{-}p_2) = abs\,(2{,}560\ ms - 1{,}860 ms) = 700\ ms$ $IBI_0 = abs\,(pp_0\text{-}pp_1) = abs\,(1{,}000\ ms - 850 ms) = 150\ ms$ $IBI_1 = abs\,(pp_1\text{-}p\text{-}p_2) = abs\,(850\ ms - 700 ms) = 150\ ms$

CONSECUTIVE TRANSITION POINTS

WAVE₁ = (P₀(LEFT VALLEY) P₆(PEAK) P₈ (RIGHT VALLEY)

WAVE₂ = (P₈(LEFT VALLEY) P₁₀ (PEAK) P₁₂ (RIGHT VALLEY)

WAVE₃ = (P₁₂ (LEFT VALLEY) P₁₃(PEAK) P₁₅ (RIGHT VALLEY)

SUMMARY

TOTAL TIME 5:00

RELAXATION POINTS 24

*FIG. 36*

CANT SEE THE
WAVES BECAUSE
ERROR CONSUMES
THE SCREEN $$\text{PEAK PLACEMENT FOR } PP_N = \frac{PP_N(p) - PP_N(V_1)}{PP(p) - PP(V_2)}$$

FREQUENCY = 60,000/WAVELENGHT MS

METHODS AND DEVICES FOR RELIEVING STRESS

RELATED APPLICATIONS

This application is a continuation-in-part of and claims priority to and benefit from U.S. application Ser. No. 11/084,456, filed Mar. 18, 2005, now U.S. Pat. No. 7,691,049. This application also claims priority to and benefit from U.S. Provisional Application No. 60/673,148, filed Apr. 20, 2005, U.S. Provisional Application No. 60/673,627, filed Apr. 21, 2005 and U.S. Provisional Application No. 60/705,883, filed Aug. 4, 2005. The contents of each of the above-referenced applications are hereby incorporated by reference in their entireties.

FIELD OF THE INVENTION

The present invention relates to methods and devices for evaluating and treating stress and stress-related disorders. More particularly the present invention relates to biofeedback devices and methods for increasing parasympathetic nerve activity by providing information on respiratory sinus arrhythmia patterns.

BACKGROUND INFORMATION

Despite the existence of many stress reduction products and services, stress and stress-related disorders still result in staggering economic and non-economic costs. It has been estimated that in the United States alone, job stress accounts for nearly $300 billion annually in terms of productivity, absenteeism and turnover. Over and above the direct work-related costs, attempts at treating stress and stress related disorders accounted for over $17 billion in anti-depression and anti-anxiety drugs in 2002. An ever upward trend in annual costs of such pharmacological treatments continues.

In addition, stress results in significant but incalculable costs due to concomitant health problems stemming directly or indirectly from underlying stress disorders. For example, studies have shown that people experiencing stress are more susceptible to viral and non-viral diseases. A common and well-known example of this is the relationship between stress and respiratory infections. Moreover, those suffering from an illness take longer to recover if suffering from stress as well.

Chronic stress can impair both the balance of the autonomic nervous system (ANS) and the efficacy of the ANS, resulting in a myriad of stress related disorders. Impairment of the ANS results in degenerative disease and premature death. For example, a clinical study examined a single two minute measurement of the ANS from 14,025 healthy men and women between the ages of 45 and 64. After eight years, those with a lower parasympathetic measurement had a much greater incidence of disease and death. Three other studies (US, Denmark, and Finland) have also examined ANS function as it relates to "all cause mortality". In each study, low parasympathetic ANS function preceded and predicted illness and death. Literally hundreds of other studies have examined ANS function as it relates to individual illnesses such as heart disease, diabetes, and stroke. For example, the British government commissioned a study on the ANS function and heart disease. Those with the lowest parasympathetic ANS function had more than a 1,000% increase in mortality rate from heart attacks. Non-economic costs of stress are also significant and include the harmful effects on relationships with family, friends, neighbors and co-workers.

The stress response involves two basic systems: the autonomic nervous system and the endocrine system. The ANS generally innervates smooth muscles of internal organs and consists of sympathetic and parasympathetic divisions. In simple terms, the sympathetic division is responsible for mobilizing energy to respond to emergencies ("fight or flight"), express emotions or perform strenuous activities, while the parasympathetic division acts to exert a calming influence and thereby balance the sympathetic system. As sympathetic nerves become increasingly active, they increase heart rate, blood pressure, breathing rates, mental activity (thereby agitating the brain) and other bodily functions. Thus, stress is maintained by high activity of the sympathetic nerves.

The endocrine system is also involved in stress-related processes. In particular, the hypothalamic-pituitary adrenal (HPA) axis plays a major role in the endocrine system's stress response. The hypothalamus secretes peptide hormones to stimulate the pituitary glands which in turn secrete its own hormones to stimulate other endocrine glands. The adrenal glands secrete cortisol which regulates metabolism and the production of energy and regulates responses in the sympathetic and parasympathetic branches of the autonomic nervous system. Cortisol levels are directly related to the degree of an individual's stress response.

In the early 1970's Dr. Herbert Benson documented the existence of a neurological and physiological state opposite of the "stress response." This state, called the "relaxation response," has been verified by other clinical investigators. From an autonomic nervous system perspective, the stress response is characterized by high activity of the sympathetic branch while the relaxation response is characterized by high activity of the parasympathetic branch. Inducing the relaxation response by definition interrupts an activated stress response. Therefore, frequent activation of the relaxation response can prevent stressors from creating on-going (i.e., chronic) stress. Also, frequent activation of the relaxation response has been shown to reverse much of the damage, including hypertension, caused by previously encountered chronic stress.

The interaction of the two branches of the autonomic nervous system (sympathetic and parasympathetic) can be characterized by examining the small changes in the time occurring between each consecutive heart beat. When an individual is at rest, variation in the beat to beat time is caused by the parasympathetic branch. This variation will increase and decrease according to an individual's respiratory pattern. During inspiration, the parasympathetic branch is inhibited, and the heart rate will begin to rise. During expiration, the parasympathetic branch engages and lowers the heart rate. This relationship between the changing heart rate and breathing is called respiratory sinus arrhythmia (RSA). RSA measurements are mathematical calculations of the degree to which the heart rate rises and falls. When the rise and fall are greater, then the activity of the parasympathetic nervous system is greater. In other words, greater RSA indicates greater parasympathetic activity. As stated previously, a sufficient increase in parasympathetic activity shifts the body into the relaxation response thereby interrupting any pre-existing stress response.

Many attempts have been made to activate the relaxation response to treat or control stress, including both invasive and non-invasive techniques and procedures. For example, acupuncture, prescription and non prescription pharmacological treatments, and psychotherapy have all been used in attempts to relieve or control stress. However, each of these therapies involves significant costs in money and time. Moreover, the effectiveness of these treatments is often less than complete and is sometimes nearly non-existent. Effectiveness often is difficult to evaluate and is many times only temporary. In addition, pharmacological treatments frequently have undesirable side effects and some may even have addiction risks. Also, even with all the available alternatives, stress still is responsible (either directly or indirectly) for more than 80% of visits to doctors.

Accordingly, a clear need exists for methods and devices for evaluating and treating stress, wherein such methods and devices are effective, non-invasive, simple to use and inexpensive. In addition, a clear need exists for methods and devices which do not have unwanted side effects or create addiction risks. In particular a clear need exists for methods and devices which promote the reduction of stress by providing high levels of uninterrupted parasympathetic activity and which are capable of immediately halting the stress response.

SUMMARY OF THE INVENTION

The present invention provides easy to use, cost-effective methods and devices for evaluating and treating stress and thereby disorders caused or exacerbated by stress. More particularly, the present invention provides methods and devices for identifying individual RSA waves and providing a subject with RSA wave information. This information can be used, for example, in biofeedback settings to assist subjects in reducing levels of stress and achieving rhythmic breathing.

The present invention also provides methods and devices which allow for the immediate cessation of the physiological stress response which prevents the stress response from harming the body and mind. Regular use of methods and devices according to the present invention allows for the reversal of physiological damage caused by prior exposures to stress, including the accumulated effects of chronic stress.

Accordingly, one exemplary embodiment of the present invention provides portable, handheld biofeedback devices for preventing, reducing or eliminating stress in human subjects.

Another exemplary embodiment of the present invention provides methods and devices for maintaining a substantially continual state of high parasympathetic activity for a sustained period of time.

Another exemplary embodiment of the present invention provides portable, handheld biofeedback devices which contain a photoplethysmograph ("PPG") sensor and a display screen to provide subjects with information on their RSA waves.

A further exemplary embodiment of the present invention provides methods and devices for training subjects to reduce levels of stress by achieving a respiration frequency of close to 6 breaths per minute.

Another exemplary embodiment of the present invention provides methods and devices which promote the reduction of stress by providing high levels of uninterrupted parasympathetic activity along with real-time feedback on such activity.

A further exemplary embodiment of the present invention provides methods and devices which give the user information about the transition in RSA waves from ascending points to descending points wherein such information can be used to guide the respiration of the user.

Yet another exemplary embodiment of the present invention provides methods for detecting and correcting erroneous data relating to RSA waves and devices which utilize such methods.

Another exemplary embodiment of the present invention provides methods for adjusting scaling on a display screen of portable biofeedback devices and devices which utilize such methods.

Still another embodiment of the present invention identifies respiration patterns including depth, rate and volume by analyzing RSA waves and provides a display of same.

BRIEF DESCRIPTION OF THE DRAWINGS

FIG. 36 illustrates an exemplary display of a session summary screen.

DETAILED DESCRIPTION

Studies have shown that controlled respiration can shift the balance between the sympathetic and parasympathetic branches. Three specific respiratory components interactively determine the amount of parasympathetic innervation. These three components include frequency, tidal volume, and expiration/inspiration ratio. In general, parasympathetic activity can be increased by reducing breath frequency, increasing tidal volume, and/or increasing the expiration/inspiration ratio. Thus, altering these three variables has the potential to increase parasympathetic activity enough to effectively elicit the relaxation response non-invasively, simply, inexpensively, and without negative side-effects.

Generally speaking, biofeedback methods and devices involve training processes which allow subjects to facilitate changes in behavior or activity in order to improve or maintain one or more physiological functions. Over time, a subject can be trained with biofeedback methods and devices to exercise greater control over these functions. In contrast to other forms of therapy in which treatment is imposed upon the subject, biofeedback methods and devices allow the subject to gradually integrate the training processes into almost automatic responses.

The present invention relates to methods and devices which can provide biofeedback information and training for subjects suffering from stress and stress-related disorders. Such biofeedback information and training may be based on an analysis of respiratory sinus arrhythmia patterns and breathing that can affect such patterns.

There are no known methods for identifying individual RSA waves during spontaneous breathing using only the RSA data set. In order to correlate RSA waves with respiration, usually heart rate and respiration rate information is collected and mapped separately. One aspect of the present invention includes the identification of the individual waves within a RSA data set. Further aspects of the present invention include the use of RSA wave patterns to provide subjects with real-time respiratory feedback information based on heart rate data. Means for decreasing or adequately controlling stress levels are also provided based on wave pattern analysis and respiratory feedback.

In addition there are no known methods for identifying individual RSA waves in real time during spontaneous breathing using only the RSA data set. An additional aspect of the present invention allows for such real-time identification and uses this information to promote the production of high levels of uninterrupted parasympathetic activity.

Exemplary Methods of Wave Pattern Identification

Figure 1:
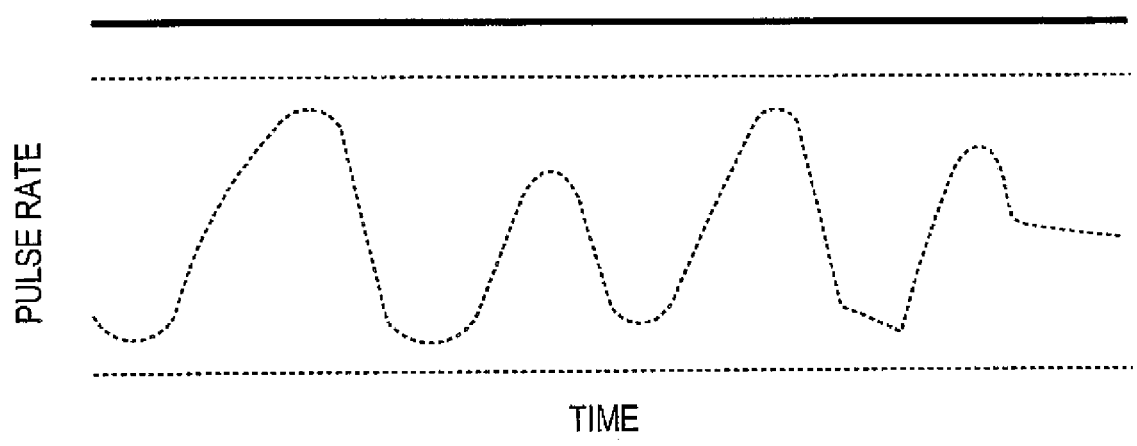
FIG. 1 illustrates a typical heart rate variability (HRV) pattern caused by respiratory sinus arrhythmia (RSA).

In one exemplary embodiment of the present invention, identification and analysis of respiratory sinus arrhythmia wave patterns begins by measuring a subject's pulse rate on a beat to beat basis. It is well established in medical literature that human heart rates, and therefore pulse rates, continually fluctuate up and down in a wave like manner (FIG. 1). These waves are known as heart rate variability (HRV) waves. When a person is physically still and resting, the HRV waves are related to a person's respiration. These resting HRV waves are medically known as respiratory sinus arrhythmia or RSA waves, as the size and shape of these waves is related to the rate, rhythm, and depth of a person's breathing. As long as a person is breathing between 4 to 15 breaths per minute, the frequency of the waves will essentially match the frequency of respiration. Most individuals breathe within this range, but even when a person is breathing outside this range, the wave frequency still provides a close approximation to the respiration frequency.

While the correlation between waves and breathing has been well established in the medical literature by visual analysis, no automated method exists to identify individual waves within a heart beat data set. An exemplary embodiment of the present invention includes a novel method of identifying each individual wave for a heart beat data set.

Figure 2:
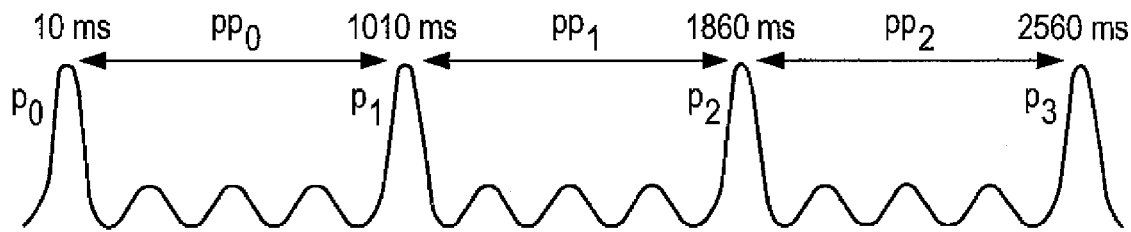
FIG. 2 illustrates an exemplary series of RSA waves and identifies several pulse peaks.

For example, the amount of time (in milliseconds) between two consecutive pulse peaks (the peak-to-peak time) is called the pp interval (pp) (FIG. 2). In an exemplary embodiment of the present invention, a device records successive pp intervals. The description of pp interval points also applies to rr intervals (the interval between consecutive R waves in an electrocardiograph or ECG), any derivative of pp intervals such as the pulse rate points, and any derivative of rr intervals such as heart rate. Collectively, these intervals may be referred to as "heart rate-related intervals." Furthermore, the same method of extracting RSA waves from pp intervals can be directly applied to these other points as well. Certain preferred embodiments of the present invention, however, parse waves within pp interval data sets.

Figure 3:
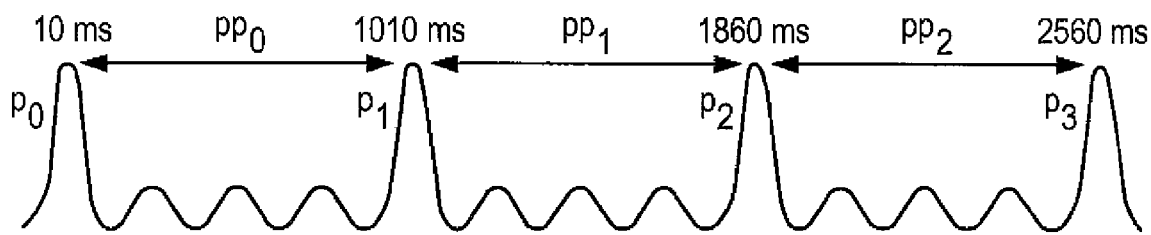
FIG. 3 illustrates an exemplary series of RSA waves and calculates the interbeat interval times (IBI) between successive pulse peaks.

The pulse rate of each recorded pp interval (60,000/pp) may be displayed on the screen each time a new pulse peak is encountered. The absolute time difference between successive pp intervals (absolute (pp[n]-pp[n−1])) is called the inter-beat interval time (IBI) (FIG. 3). An aspect of the present invention uses the pp interval times to identify individual RSA waves. The methods described herein may be used for both spontaneous and guided breathing.

Figure 4A:
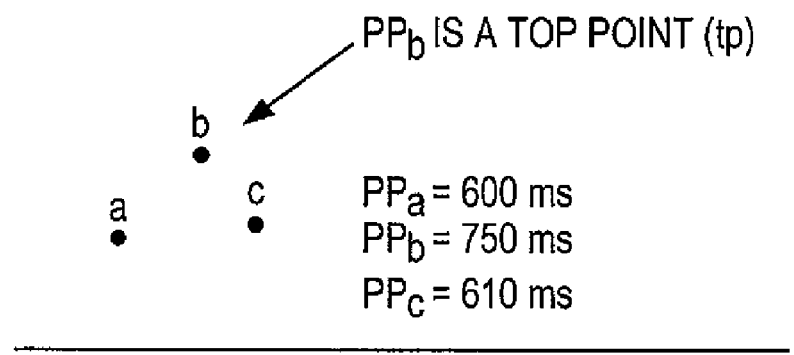
FIGS. 4a-d identify, respectively, a representative top point, bottom point, ascending transition point and descending transition point.
Figure 4B:
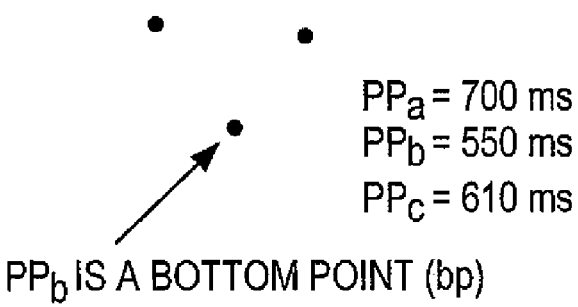
Figure 4C:
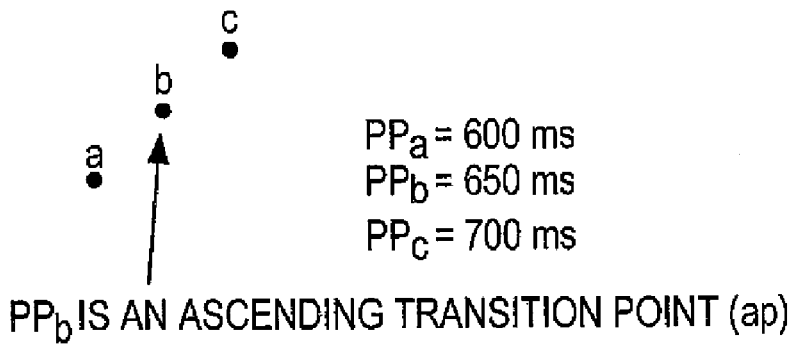
Figure 4D:
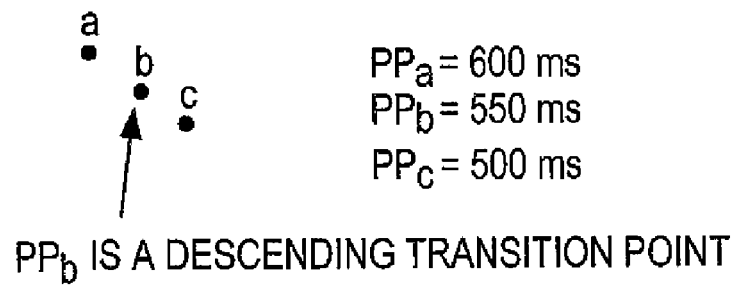
Figure 5:
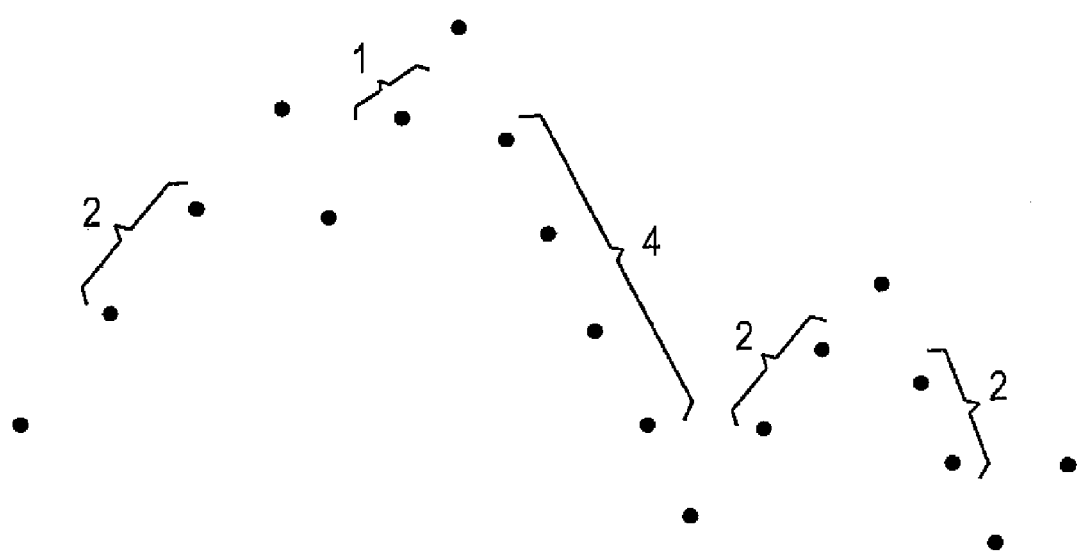
FIG. 5 illustrates representative consecutive ascending and descending transition points.

Each p-p may be categorized by examining its relationship to the p-p immediately before it (the previous pp) and the p-p immediately after it (the next p-p). A p-p may be considered a top point (tp) if the previous p-p is equal to or less than it and the next p-p is equal to or less than it as well (FIG. 4a). A p-p may be considered a bottom point (bp) if the previous p-p is equal to or greater then it and the next p-p is equal to or greater than it as well (FIG. 4b). A p-p may be considered an ascending transition point (at) if the previous p-p is less than it and the next p-p is greater than it (FIG. 4c). A p-p may be considered a descending transition point (dt) if the previous p-p is greater than it and the next p-p is less than it (FIG. 4d). Thus, a p-p may be categorized as either a top point (tp), bottom point (bp), ascending transition point (at), or descending transition point (dt). The term "transition point" can be used to refer to both ascending and descending transition points when it is not qualified with the words "ascending" or "descending". Consecutive transition points refers to a series of consecutive ascending transition points or descending transition points (FIG. 5).

Figure 6:
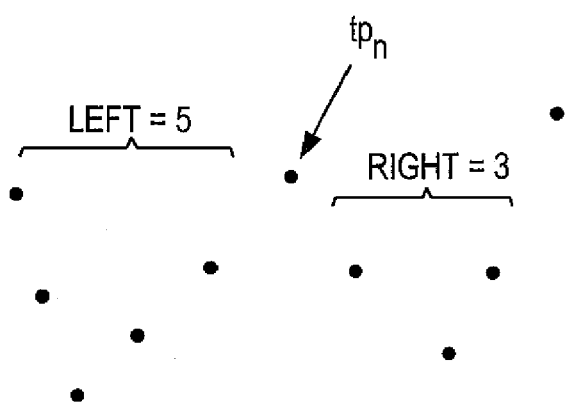
FIG. 6 illustrates an exemplary method for identifying a top point.

The term "top level" may be used to refer to the relative height of the top point. The level of a top point may be computed as follows. L=the number of consecutive points immediately to the left of the top point that are less than or equal to the top point. R=the number of consecutive points immediately to the right of the top point that are less than or equal to the top point. If L<R, then the top level is equal to L, otherwise the level of the top is equal to R. FIG. 6 illustrates, using three examples, how the top point level may be categorized.

Figure 7:
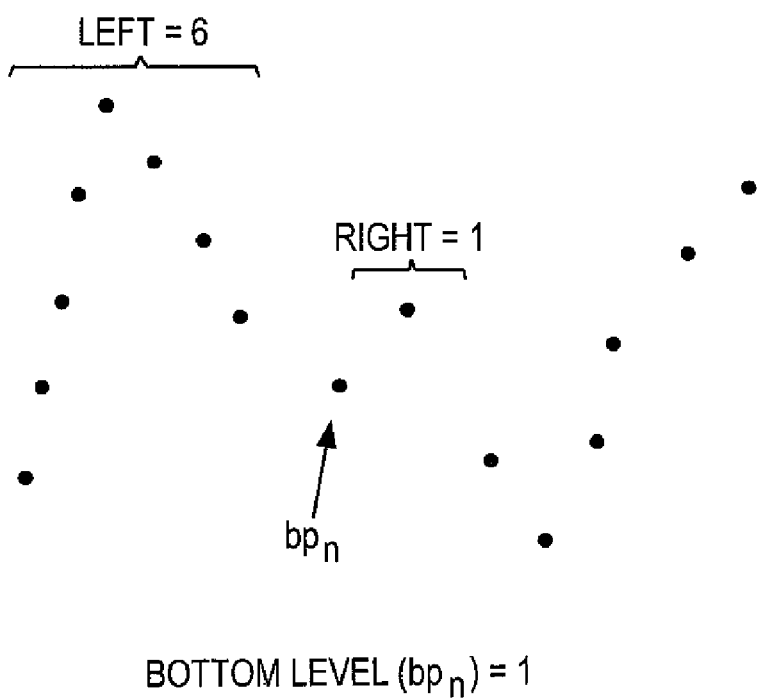
FIG. 7 illustrates an exemplary method for identifying a bottom point.

The term "bottom level" may be used to refer to the relative height of the bottom point. The level of a bottom point may be computed as follows. L=the number of consecutive points immediately to the left of the bottom point that are greater than or equal to the bottom point. R=the number of consecutive points immediately to the right of the bottom point that are greater than or equal to the bottom point. If L<R then the bottom level is equal to L otherwise the level of the bottom is equal to R. FIG. 7 illustrates, using three examples, how the bottom point level may be categorized.

Figure 8A:
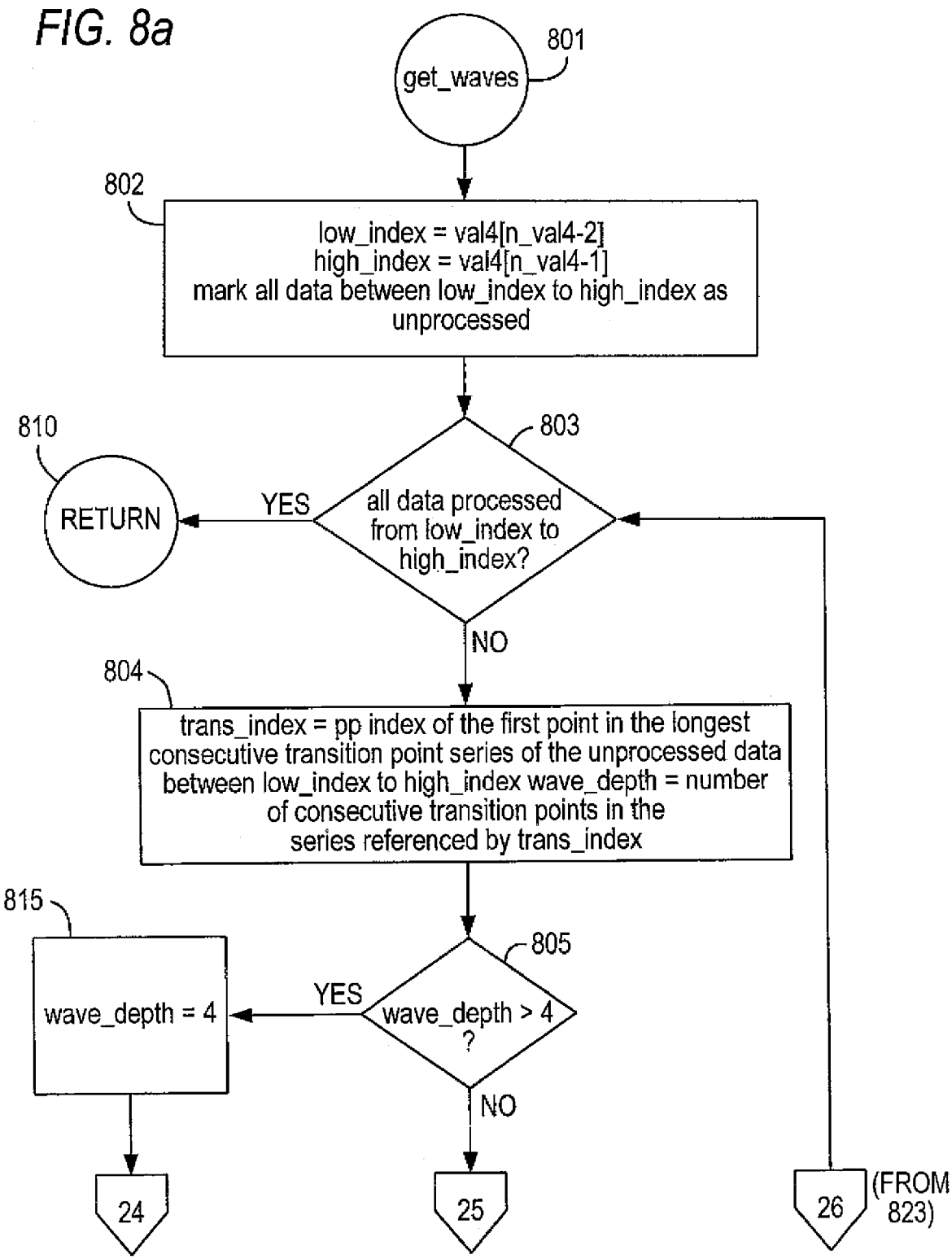
FIGS. 8(a)-(b) depict an exemplary process flow for an exemplary procedure for finding RSA waves within a data set according to an exemplary embodiment of the present invention.
Figure 8B:
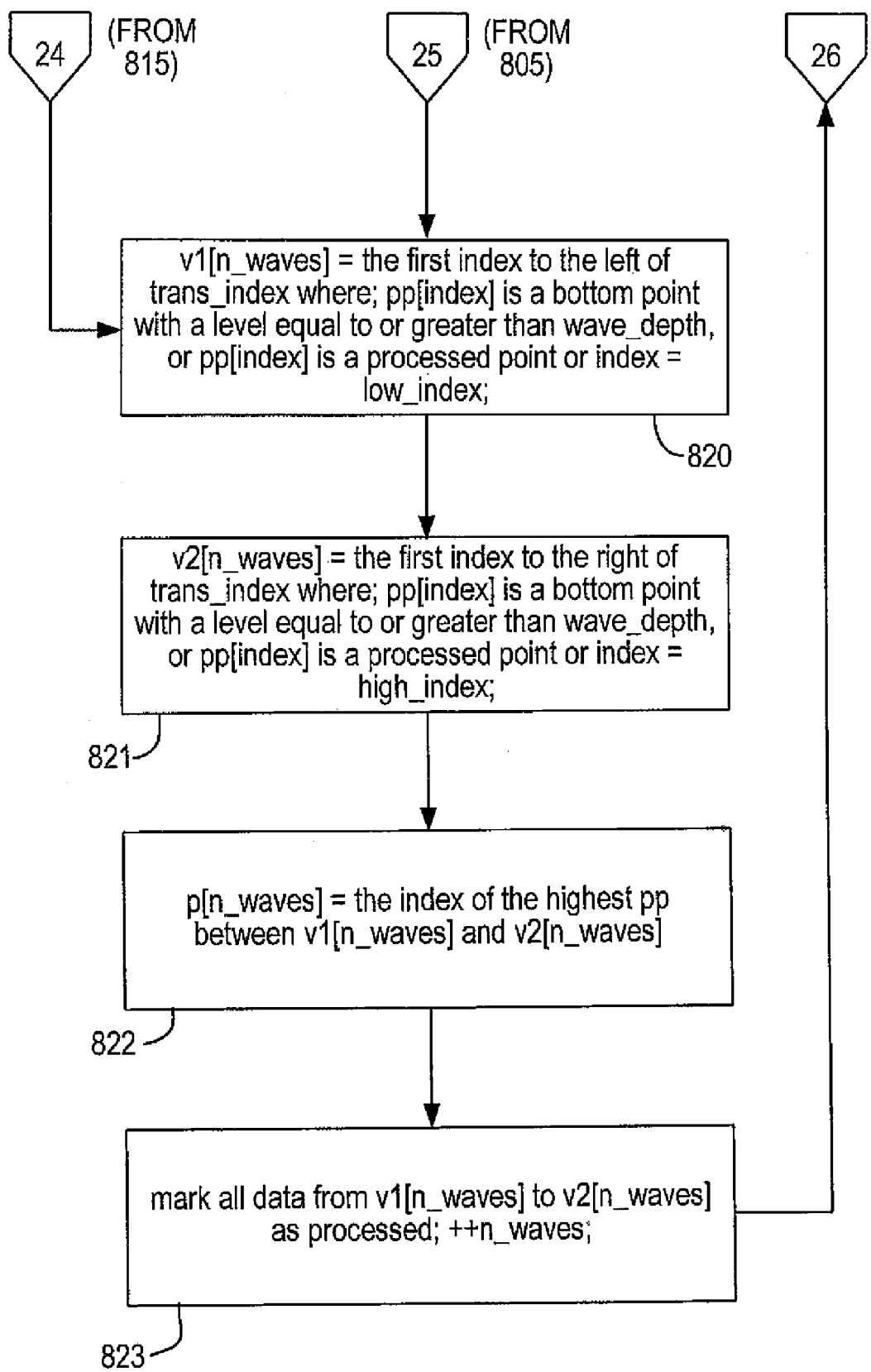
Figure 9:
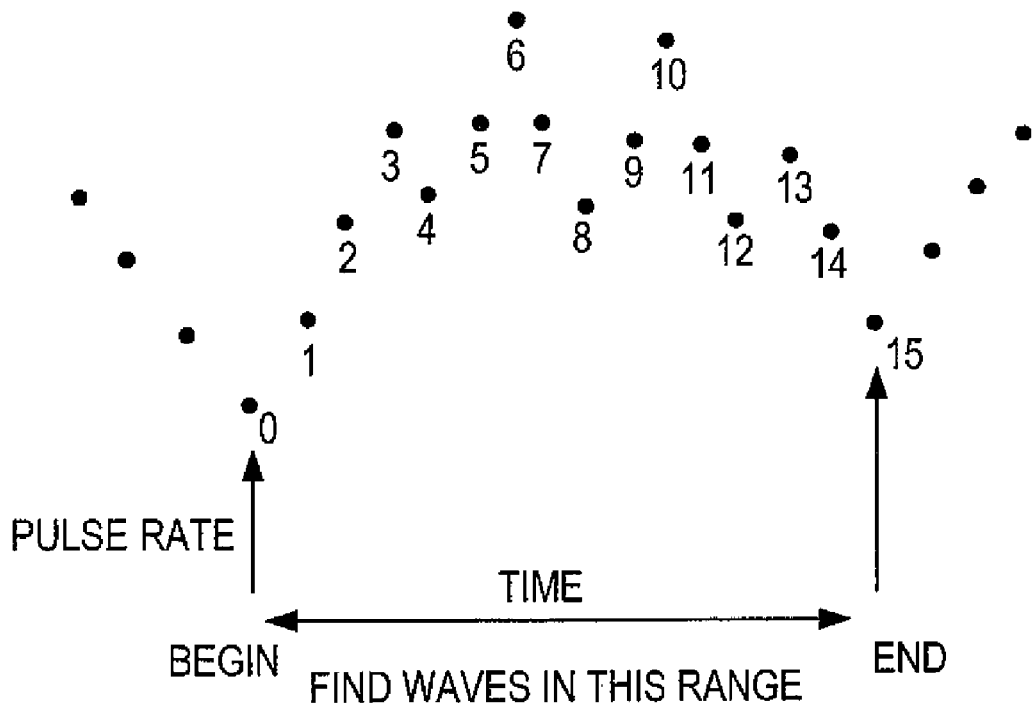
FIG. 9 illustrates an exemplary procedure for identifying RSA waves within a data set.

FIGS. 8(a)-(b) provide an exemplary flowchart which illustrates an exemplary procedure for finding the RSA waves within a data set while FIG. 9 illustrates how this procedure may be applied. In an exemplary embodiment of the present invention, the first step is to locate the highest number of consecutive transition points (ctp) in the data set. In FIG. 9 the highest number of consecutive transition points begins at point 1. There are 2 consecutive transition points. The wave depth is equal to the number of these transition points. Thus, the wave depth in this example is 2. In preferred embodiments, if the wave depth is greater than 4, the wave depth value is adjusted down to 4.

The next step is to locate the bottom point to the right of the consecutive transition points where the bottom level is equal to or greater than the wave depth. This is the right valley point (v2) of the RSA wave. In the example in FIG. 9, bottom point no. 8 has a level of 3, which is greater than the wave depth. The next step is to locate the bottom point to the right of the consecutive transition points where the bottom level is equal to or greater than the wave depth. This is the left valley point (v1) of the RSA wave. In the example provided in FIG. 9, bottom point no. 0 has a level 4, which is greater than the wave length. The next step is to find the highest point between the left valley point and the right valley point. This is the peak (p) of the RSA wave. In the example in FIG. 9, point 6 is the highest point between the two valley points. All data from the left valley point (v1) to the right valley point (v2) is considered processed data. The same procedure is repeated on the remaining unprocessed data until all possible waves have been identified.

There are a number of variations in the method described above which should be considered within the scope of the present invention. For example, a similar method could be used to find peaks on each side of a transition point series. The valley between two peak points would therefore be the lowest point between the two peaks. Also, wave depth may be based on the absolute number of transition points or a derived number based upon the number of transition points (e.g., number of transition points×75%). Also, the v1 point could be identified before the v2 point.

In preferred embodiments, the wave parsing method discussed above is used each time a new bottom level 4 point is identified. Thus, devices according to exemplary embodiments of the present invention "look" for RSA waves between bottom level 4 points. In other exemplary embodiments, devices may be configured to "look" for RSA waves after each point, or after a certain period of time elapses (every 30 seconds for example), etc. Exemplary embodiments use bottom level 4 points because they have a very high probability of delineating RSA waves. That is, they have a high probability of being valley points (v1, v2) of RSA waves.

Figure 10:
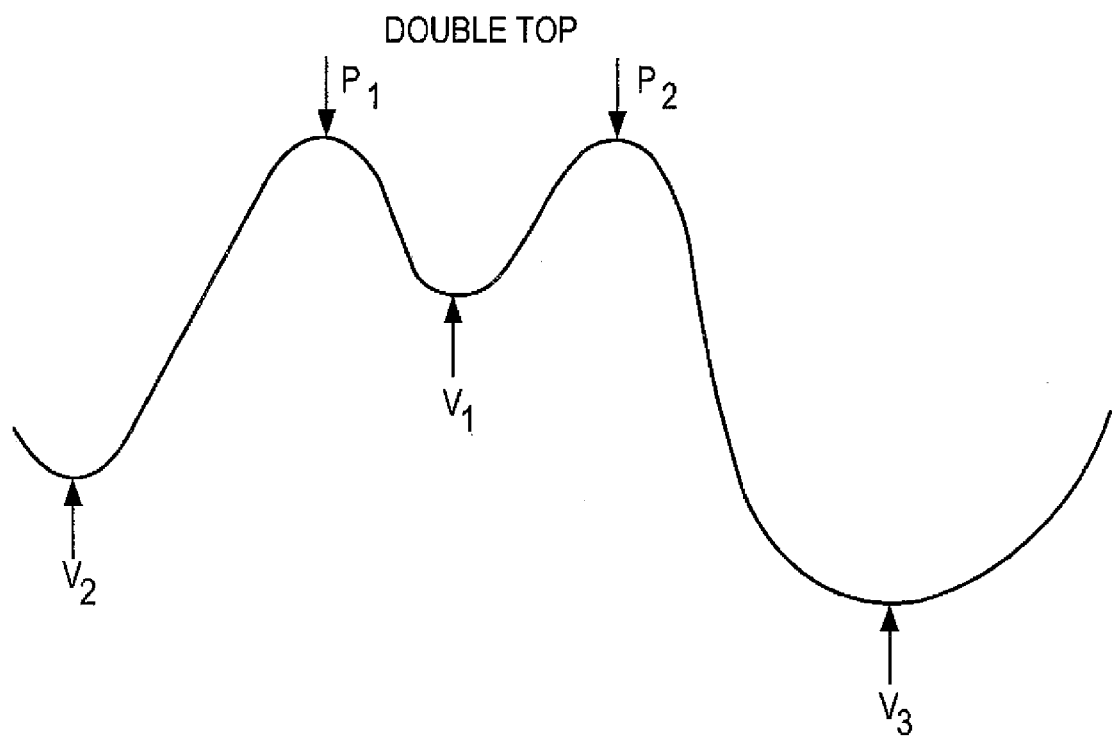
FIG. 10 illustrates an exemplary double top wave.

There are two instances where the basic RSA wave parsing methods described above may inaccurately describe an RSA wave. One may occur when a double top wave is encountered. Double top waves may be formed when a person waits a long time to inhale after he or she has already exhaled. Another may occur when double bottom waves are formed. Double bottom waves may be formed when a person holds his breath for a long time after inhaling. Double tops are easily identified by examining the ratios of lengths of the two waves (FIG. 10). When (p1-v2) is much smaller than (p1-v1), and (p2-v2) is much smaller than (p2 -v3), and (p1-v2) is very close to (p2-v3) then a double top has occurred. In preferred embodiments, double tops may be defined as situations where: ((p1-v2)/(p1-v2))<0.50 and ((p2-v2)/(p2-v3))<0.50 and ((p1-v1)/(p2-v3))>0.75. Double bottoms may be defined as the inverse of double tops.

Figure 11:
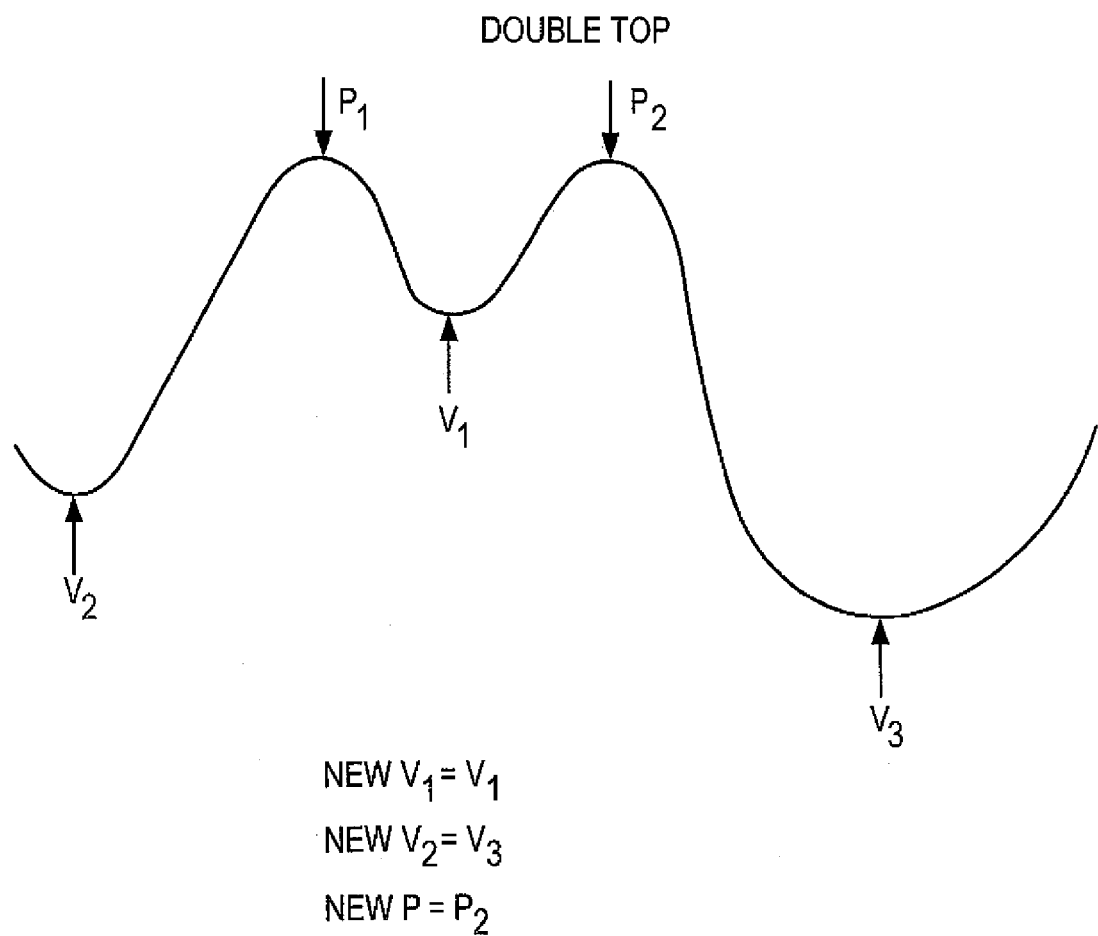
FIG. 11 illustrates an exemplary method for correcting data from a representative double top wave.

Whenever double tops or double bottoms are produced from the basic parsing method, the two waves forming the pattern may be merged together into one wave. Point v1 is the v1 of the new wave. Point v3 becomes the v2 of the new wave. The highest value between v1 and v3 is the peak point of the new wave. This is illustrated by FIG. 11

Figure 12:
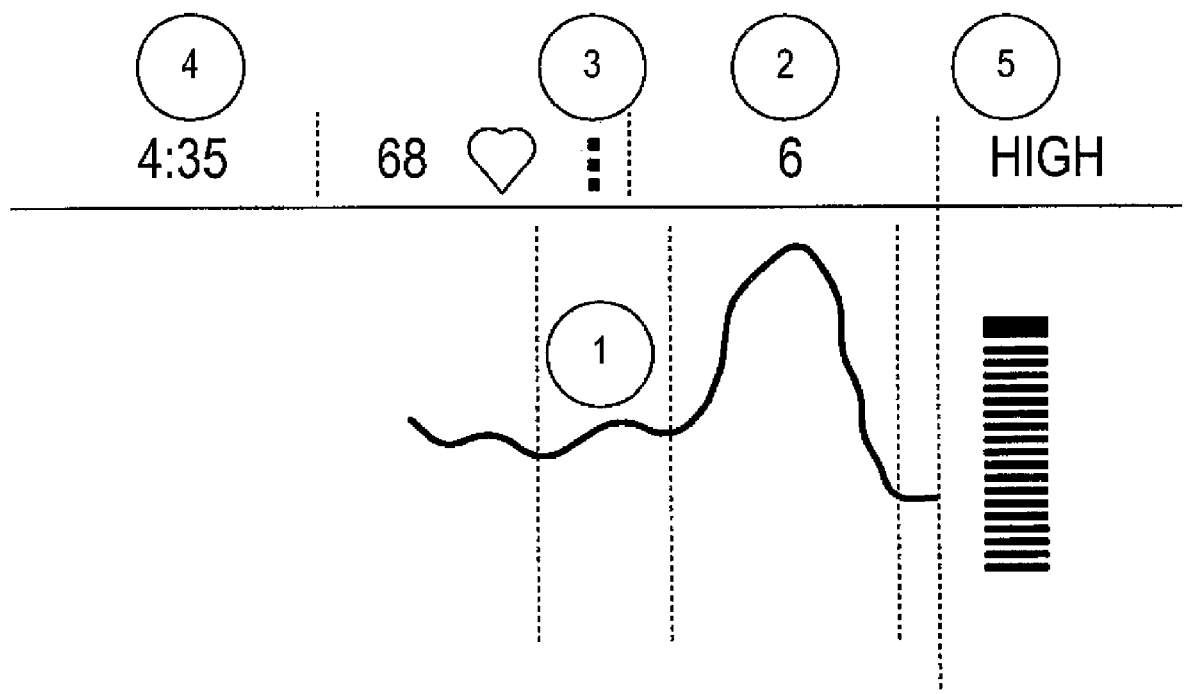
FIG. 12 illustrates an exemplary display of a stress meter.

Exemplary embodiments of the present invention can use the RSA wave information described above to assess the user's level of mental stress. This mental stress measurement may be presented in devices as a stress meter (FIG. 12(5)). For example, when a person is stressed, breathing usually becomes rapid and irregular, relative to a non-stressed state. This rapid, irregular breathing can cause the formation of short, choppy RSA waves. Methods and devices according to the present invention can be used to determine the user's stress level by determining how far the user's average wavelengths deviate from a level that represents a relaxed state. Such methods and devices also may compute how irregular (arrhythmic) the user's waves are. These two assessments may be used individually or combined into a single value to indicate the overall stress level.

Studies have demonstrated that when people are profoundly relaxed (such as in a state of deep meditation), they tend to breathe in a steady rhythm at approximately 6 breaths per minute. Such rhythmic breathing causes the RSA wavelengths to become entrained on the breathing frequency. Thus, rhythmic breathing at 6 breaths per minute will result in a series of RSA waves having wavelengths of 10 seconds. Thus, exemplary embodiments of the present invention use wavelengths of 10 seconds as the relaxation threshold when assessing the user's stress level. Exemplary embodiments also include methods and devices which compute the average wavelength of the last five waves to determine how far the average is, proportionally, from 10 seconds. This is one example of a "wavelength score".

Arrhythmic waves may be quantified using a number of standard variance formulas. Exemplary embodiments of the present invention use the sum of the differences of each consecutive wavelength in the last five waves to compute a "variance score". Exemplary embodiments also can use the sum of the differences between successive wavelengths and may use a rank order weighted averaging so that the variance of the most recent waves count more. The stress level in an exemplary embodiment of the present invention uses 70% of the "wavelength score" +30% of the "variance score". The user's stress level can be recalculated each time a new RSA wave is identified.

Stress can cause a variety of RSA wave behaviors: decreased peak to peak times, increased peak to peak frequency, decreased wavelength, increased wave frequency, decreased amplitude, irregular wavelengths, irregular wave frequencies, irregular amplitudes, irregular peak to peak times, irregular peak to peak frequencies, irregular peak placements or decreased variation. Any one of the preceding variables, or any combinations thereof, can be applied to RSA waves and used as an indicator of the level of stress. Identifying individual RSA waves and using any of the preceding variables alone, in combination with each other, and/or in combination with other variables, to evaluate stress is within the scope of the present invention and has not been described in the prior art.

In addition to using the identified RSA waves for determining stress levels, devices and methods according to exemplary embodiments of the present invention can also use RSA wave information to determine and display both average heart rate and wave frequency. The average of all the pulse rates in the last wave may be used to assess average heart rate. For example, each time a new RSA wave is identified, the average of the pulse rates may be computed and the heart rate may be updated. The wave frequency display also may be updated every time that a new RSA wave is identified. Exemplary embodiments can express frequency relative to waves (breaths) per minute. In exemplary embodiments the wave frequency and heart rate may be rounded to the nearest integer.

Exemplary Methods of Real-Time Wave Pattern Identification

The present invention provides also provides methods of real-time RSA wave pattern identification. In certain embodiments such methods involve two primary interrupt driven processes.

The first process may be triggered each time a new pulse is detected by a PPG sensor. This process may provide for (1) converting received pulses into a pulse rate values (prv); (2) updating the wave display with the new prv; (3) confirming whether a new prv marks the beginning of a new wave (indicating that the previous wave has just been completed); (4) delineating the boundaries of the last wave (identifying the valley-peak-valley points); (5) assessing parasympathetic activity of the wave; (6) displaying an appropriate symbol under the wave; (7) updating the wave history; and (8) updating the score.

A second process may be responsible for detecting and marking drop points in real-time. This process may be driven by a clock interrupt. In preferred embodiments, this process may occur, for example, every 250 milliseconds. When the process detects the occurrence of a drop point, it may be marked with a drop point indicator, such as a triangle, for example.

Either of these processes may be implemented using standard polling methods. Alternatively, the second process may occur each time a pulse is detected. Exemplary embodiments use clock interrupts so that the drop point is detected more quickly. Reasonable results may be provided, however, by marking the drop point based on received pulse beats.

Preferred embodiments of the present invention also provide various methods for the precise characterization of RSA wave patterns in real time. Such methods include those that may be conveniently referred to as "wave phase" methods and "wave side" methods.

Methods of Determining Wave Phase

Figure 13:
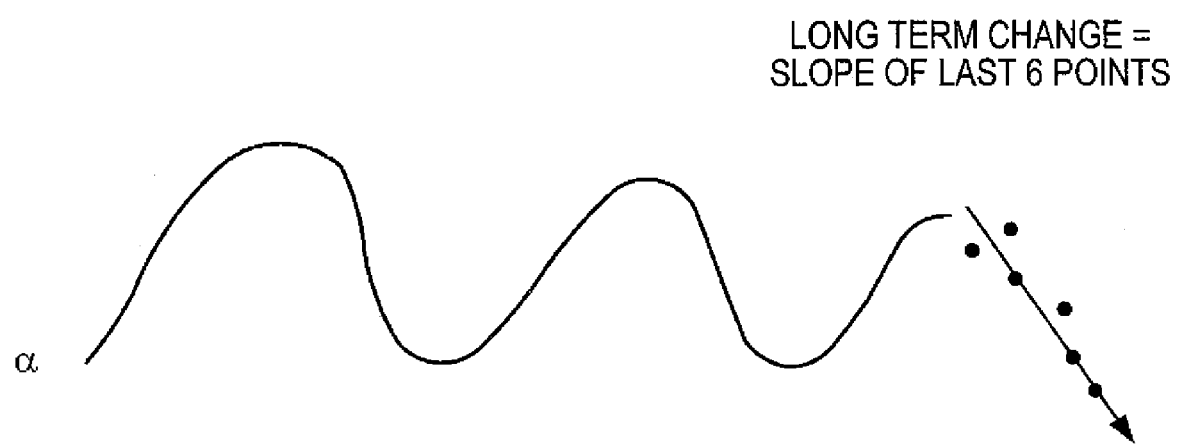
FIG. 13 illustrates an exemplary method for determining long term direction of RSA waves.

The present invention also provides methods of determining wave phase and devices which utilize such methods. In exemplary embodiments of the present invention, each time that a new pulse comes in, a long term wave direction can be assessed. This process is illustrated in FIG. 13. For example, the slope of the last six (6) pulse rate points can be used. The resulting value can, for example, be termed the "long slope". Alternatively, the slope of a time based sliding window of points, for example, can be used (such as, for example, the last 12 seconds, the last 5 seconds, etc.), or, for example, another general indicator of direction could be used.

Next, for example, the absolute amount of long term change can then be computed. This provides a degree of change value. In exemplary embodiments of the present invention the absolute value of the long slope can be used, which can be termed, for example, the "absolute long slope". Alternatively, for example, the absolute value or similar conversion of any of the long term wave assessments can be used.

Next, for example, the short term direction of the wave can be determined. In exemplary embodiments of the present invention the slope of the last three (3) pulse rate points can, for example, be used. This can be termed, for example, the "short slope". Alternatively, for example, any directional indicator on a smaller subset of points than the points chosen for the long term direction assessment can be used.

Then, for example, the short term direction indicator and the absolute long term indicator can be used to assess the actual direction of the wave itself. In exemplary embodiments of the present invention the short slope can be compared to the absolute long slope, for example. If the short slope is greater than, for example, 30% of the absolute long slope, then the wave direction can, for example, be considered as UP. If the short slope is less than (−1)*30% of the absolute long slope, then, for example, the direction can be considered as DOWN. If it fails both tests, then the direction can, for example, be considered to be FLAT.

In alternate exemplary embodiments of the present invention a different percentage can be chosen for these determinations. Percentages may be based on the degree of desired parasympathetic sensitivity. Higher percentages may be less sensitive to parasympathetic interruption, while lower percentages may be more sensitive. Around 30% is generally sensitive enough to detect major interruptions, yet forgiving enough to put the behavior within the control of the user.

In addition, in exemplary embodiments of the present invention, the percentage for determining an UP direction can be different from the percentage determining a DOWN direction. Alternatively, other mathematical comparisons of the short slope to absolute long slope can be used, for example, to determine the relative relationship between the two and thereby determine wave direction. Alternatively, other mathematical functions may be used in place of short slope and absolute long slope to assess, for example, the short term direction and the long term degree of change.

Figure 14:
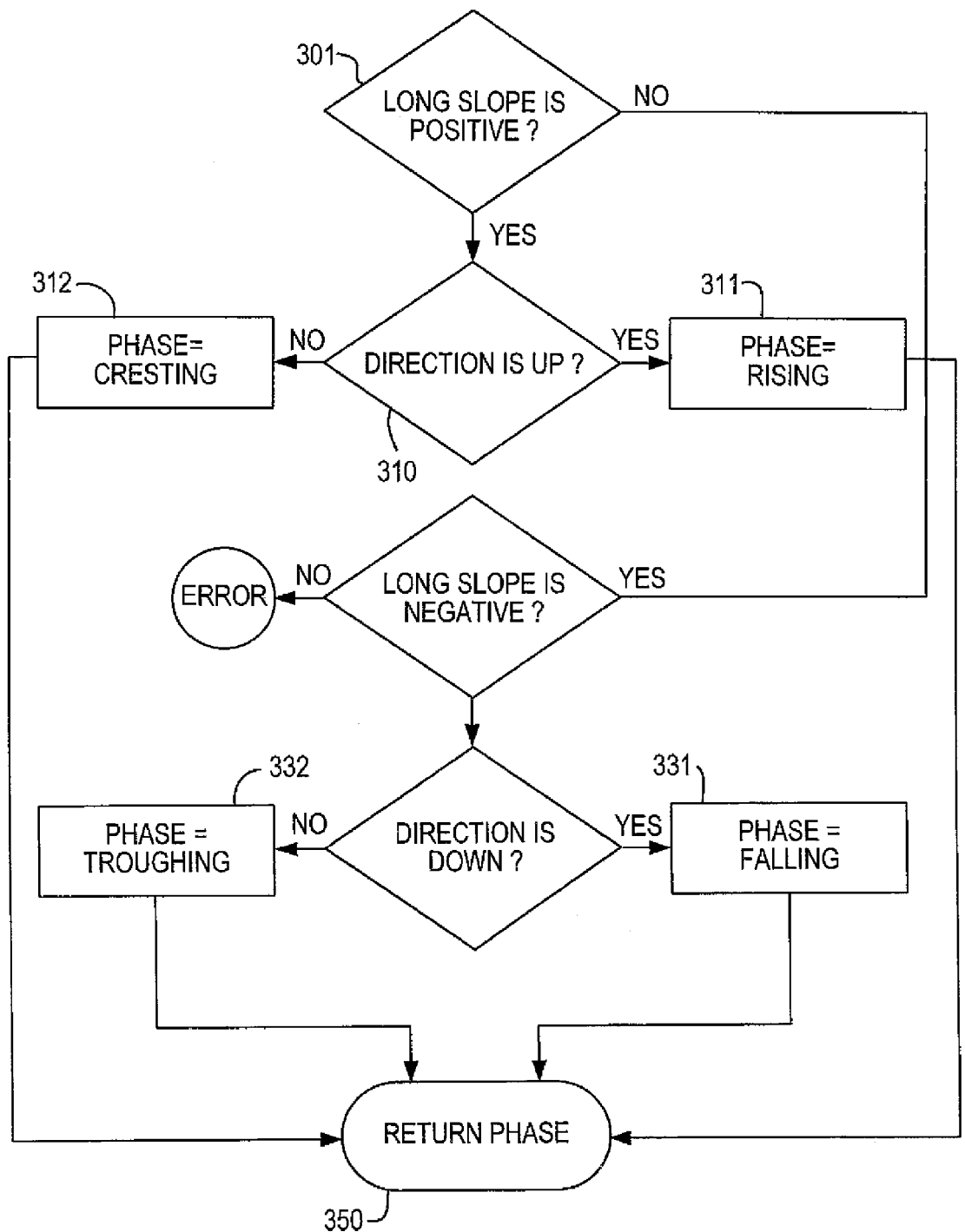
FIG. 14 illustrates an exemplary process flow for an exemplary procedure for determining wave phase.

Next, the wave direction and the long term direction can be used, for example, to determine the phase of the wave. In exemplary embodiments of the present invention the wave direction and the long slope can be examined in order to make this assessment, as is illustrated, for example, in the exemplary process flow diagram of FIG. 14. Process flow begins at 301, where the query "Long Slope is Positive?" is evaluated. If, for example, at 301 the long slope is positive, process flow moves to 310, where the query "Direction is Up?" is evaluated. If at 310 the direction is UP, then process flow proceeds to 311 and the phase is determined to be RISING. If, for example, at 301 the long slope is positive, but at 310 the direction is not UP, then process flow proceeds to 312 and the phase is determined as CRESTING. If, for example, at 301 the long slope is negative (i.e., a "No" is returned at 301 to the query "Long Slope is Positive?") which moves process flow to 320, and then at 320 a "Yes" is returned to the query "Direction is Up?", then process flow proceeds to 330. If at 330 the direction is DOWN, then process flow moves to 331 and the phase is determined to be FALLING. Alternatively, if at 320 the long slope is negative, but at 330 the direction is not DOWN, then process flow moves to 332 and the phase is determined to be TROUGHING. At each of 312, 311, 332 and 331 the result is passed to 350, where the phase as determined can be returned to another process for further processing or output.

Methods of Determining Wave Side

Figure 15:
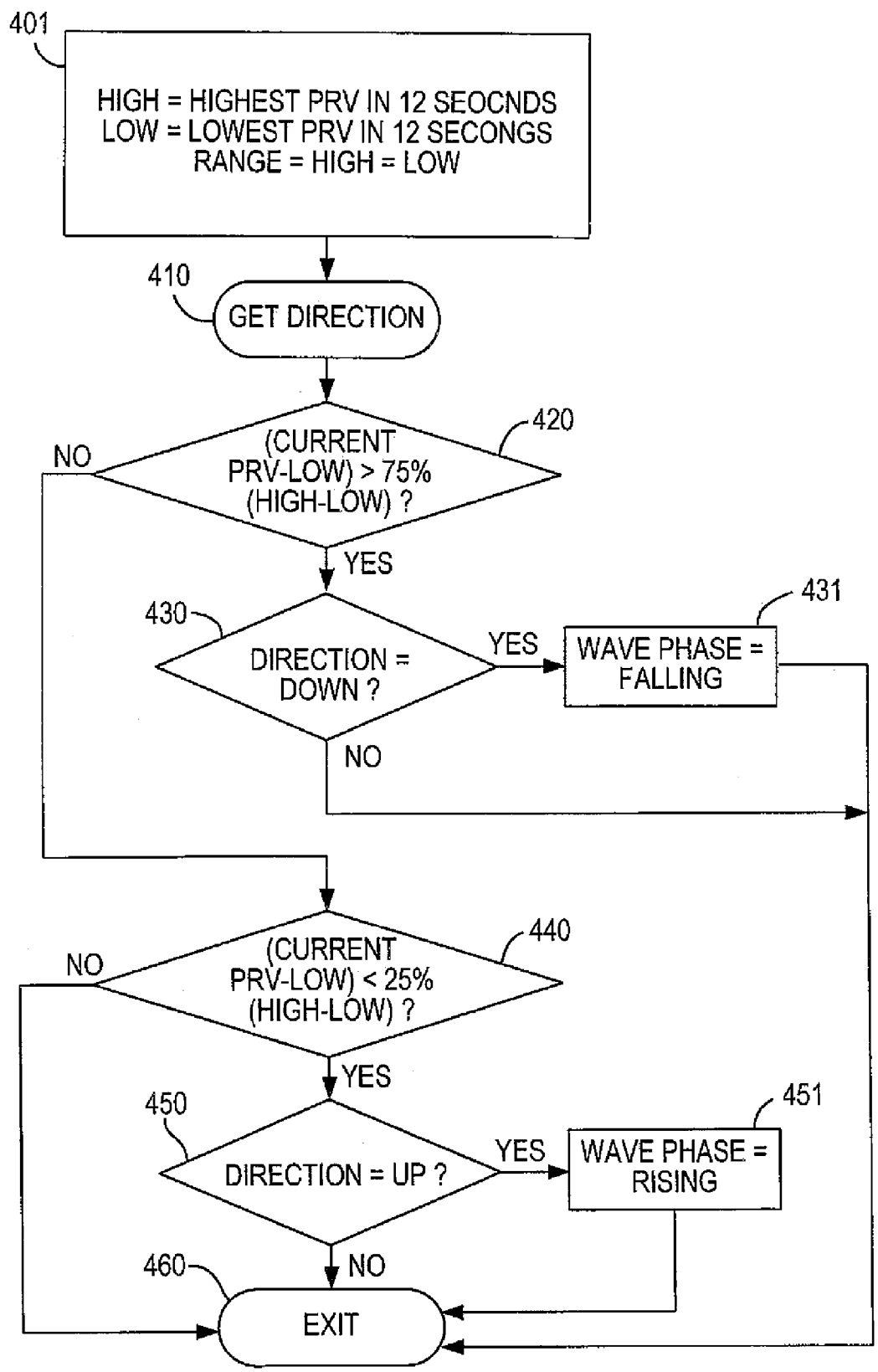
FIG. 15 illustrates an exemplary process flow for an exemplary procedure for determining wave side.

The present invention also provides methods of determining wave side and devices which utilize such methods. Thus, in exemplary embodiments of the present invention an alternative to determining all four phases of the wave can be implemented. This alternative method can, for example, just detect the RISING and FALLING phases of a wave using a combination of range and direction. An exemplary process flow for this method is illustrated in FIG. 15. Process flow begins at 401, where "High"—highest prv in a given interval, "Low"—lowest prv in a given interval, and "Range"—High—Low, values can, for example, be obtained. "High", "Low" and "Range" refer to assessing prv values in a sliding window (such as, for example, the last 12 points, the last 12 seconds, etc.). In exemplary embodiments of the present invention the prv range of the last 12 seconds can be used. At 410 Direction can be assessed, as described above.

Once Range and Direction are computed, Phase can be assessed. This can be done by looking at wave direction and current prv in relation to the range. If wave direction is up at the bottom of the range then wave phase has shifted to rising. Alternatively, if wave direction is down at the top of the range then wave phase has shifted to falling. Whether a wave is in the top or bottom of its range can be determined, for example, by choosing a fraction or percentage of total range, as shown in FIG. 15, where being within 25% of the top of the range is considered as near the top, and being no more than 25% above the bottom of the range is considered as near the bottom. In alternate exemplary embodiments other thresholding values can be used.

With reference to FIG. 15, for example, at 420 the current prv can be tested for being in the top 25% of the Range. If at 420 the last point is near the top of the range, i.e., "Yes" at 420, then process flow can proceed to 430 where wave direction is analyzed. If at 430 wave direction is DOWN, then process flow moves to 431 and the wave phase is determined to have shifted to FALLING, and the process is exited at 460.

However, if at 420 the current prv is not in the upper 25% of the range, then process flow moves to 440. At 440 the wave is tested for being in the bottom 25% of the range. If Yes, process flow moves to 450, where, for example, wave direction can be assessed. If, for example, at 450 wave direction is UP, then process flow moves to 451 where wave phase is determined to have shifted to RISING, and the process is exited at 460.

If at 420 the wave is not in the upper 25% of its range, and at 440 the wave is not in the bottom 25% of its range, then process flow moves to 460 and the process is exited. The process is also exited if at 450 the wave direction is not UP or if at 430 the wave direction is not DOWN.

Thus, in exemplary embodiments of the present invention either method, Wave Phase (FIG. 15) or Wave Side (FIG. 14), can be used to determine current phase. In many contexts Wave Side, for example, can be used inasmuch as the use of the range adds a degree of precision. However, in other embodiments where it is desirable to track all four phases, Wave Phase, for example, may be used inasmuch as it also identifies TROUGHING and CRESTING.

Methods of Determining Wave Completion

Figure 16A:
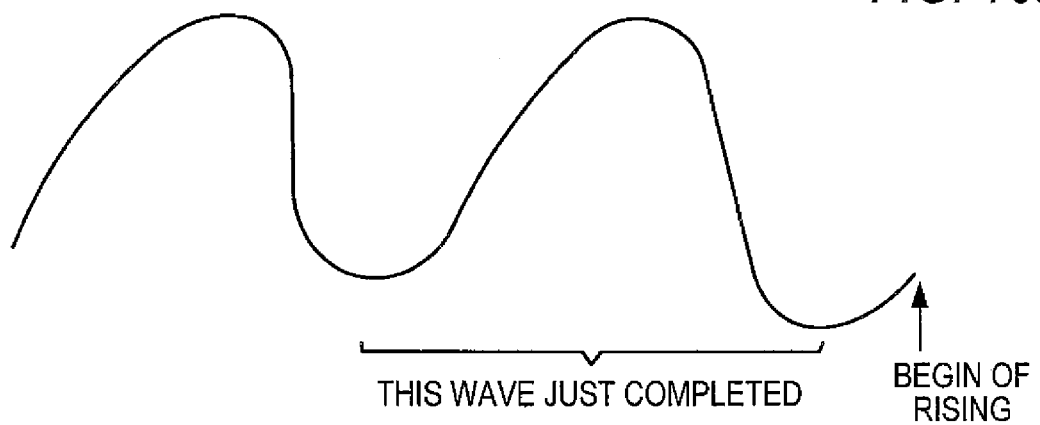
FIGS. 16(a)-(b) illustrate exemplary methods for determining wave completion.
Figure 16B:
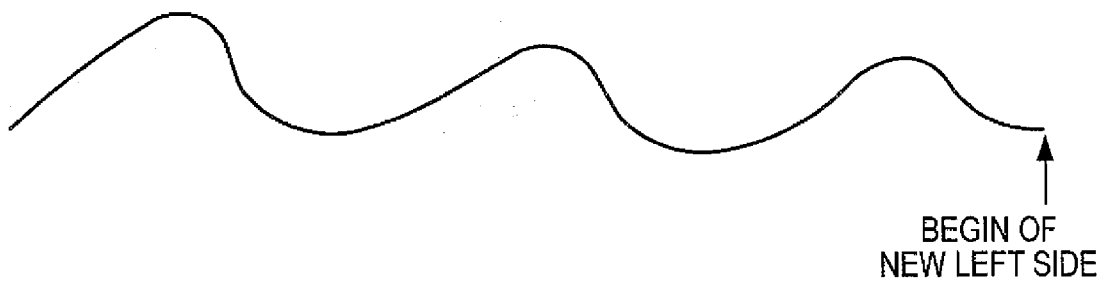

The present invention also provides methods of determining wave completion and devices which utilize such methods. In exemplary embodiments of the present invention, to determine when a new wave has been completed, the current phase can be tracked on a beat-to-beat basis, using, for example, the phase determination method as described above. When the current phase shifts to RISING, it is known that a wave has recently finished, as shown, for example, in FIG. 16a. Alternatively, for example, the wave side can be tracked on a beat-to-beat basis. When the wave side shifts to LEFT, then it is known that a new wave has been completed, as shown, for example, in FIG. 16b.

Methods of Delineating Wave Boundaries

Figure 17:
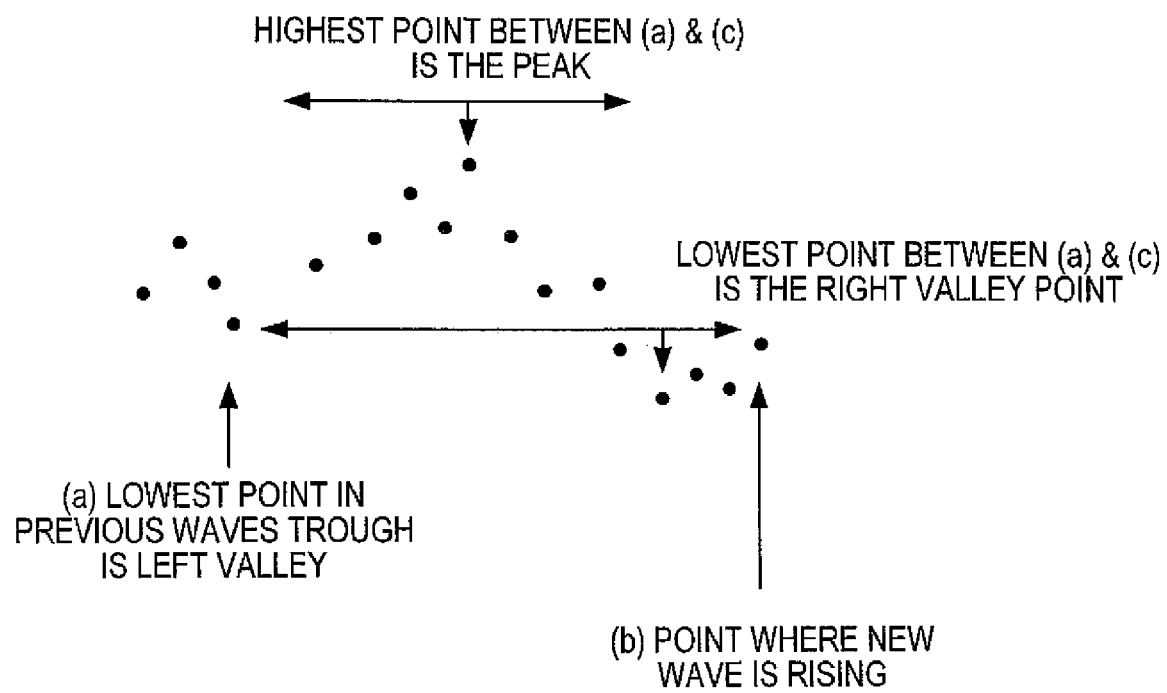
FIG. 17 illustrates an exemplary method for delineating wave boundaries.

The present invention also provides methods of delineating wave boundaries and devices utilizing such methods. Thus, once it has been determined that a new wave has finished, the points between the beginning of the previous wave trough and the point where the new wave is rising may be obtained, as shown, for example, in FIG. 17. The lowest point in the previous wave trough may be referred to as the left-valley point. The lowest point between the left-valley and the new rising point may be referred to as the right-valley point. The highest point between the left-valley point and the right-valley point may be referred to as the peak.

Alternatively, a wave side analysis could be performed using, for example, the points from the previous wave's right side up to the end of the newly formed wave's right side. The lowest point in the previous wave's right side may be referred to as the left-valley point. The lowest point between the left-valley point and the new waves right side may be referred to as the right-valley point. The highest point between the left-valley point and the right-valley point may be referred to as the peak.

Methods of Assessing Parasympathetic Activity

The present invention also provides methods of assessing parasympathetic activity and devices which utilize such methods. In exemplary embodiments wave boundaries may be used in the assessment of parasympathetic activity. In certain embodiments of the present invention, two parasympathetic parameters may be measured for the resulting wave: the intensity of the parasympathetic response and the continuity of parasympathetic activity.

In one embodiment, the intensity of parasympathetic response may be determined, for example, by the wavelength (timestamp of the right-valley point minus the timestamp of the left-valley point). If the wavelength is less than, for example, 6 seconds, the intensity may be considered LOW. If the wavelength is greater than, for example, 6 seconds and less than, for example, 9.5 seconds, the intensity may be considered MEDIUM. If the wavelength is greater than or equal to, for example, 9.5 seconds, the wavelength may be considered HIGH.

In alternative embodiments the parasympathetic activity level also may be assessed using traditional RSA measurements such as, for example, consecutive heart period, standard deviation, mean deviation and the like.

Figure 18:
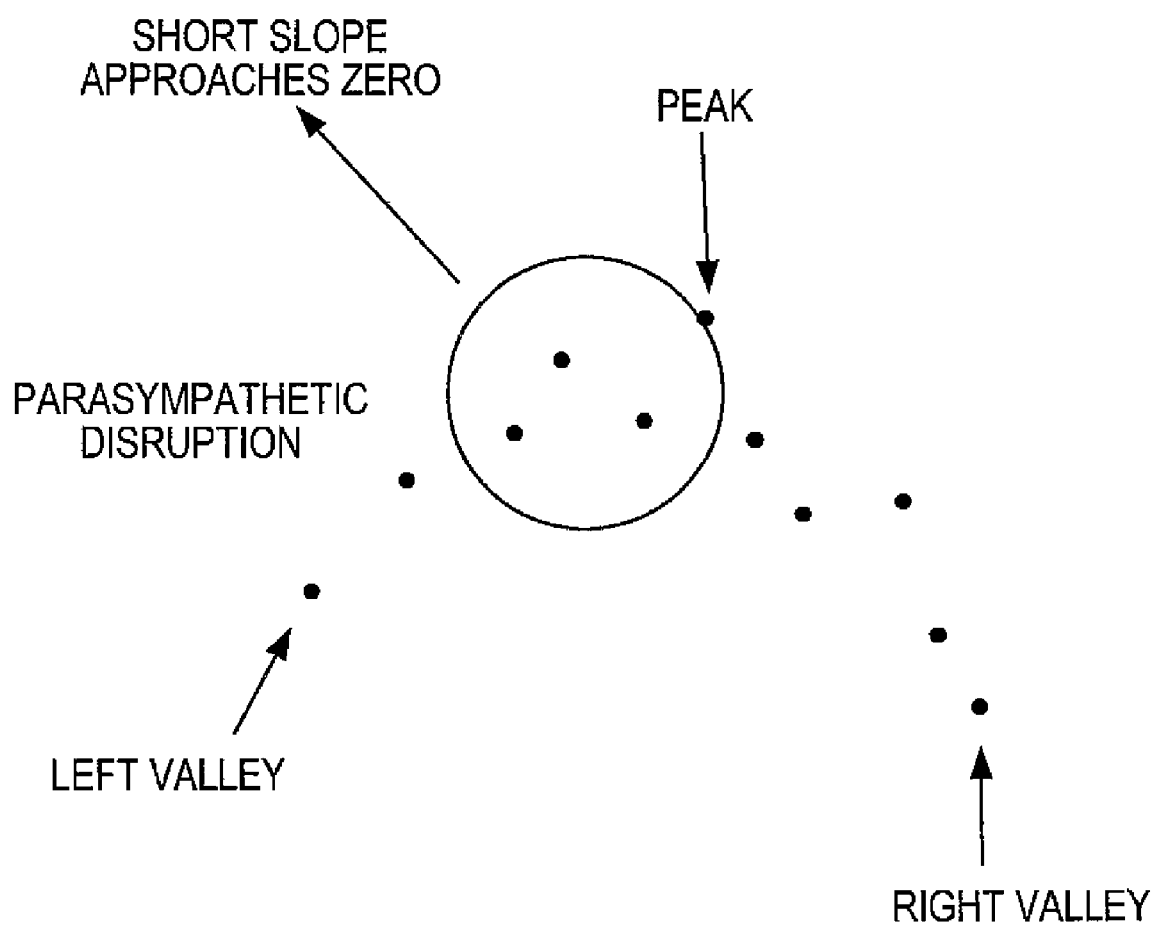
FIG. 18 illustrates an exemplary method for assessing continuity parasympathetic activity
Figure 19:
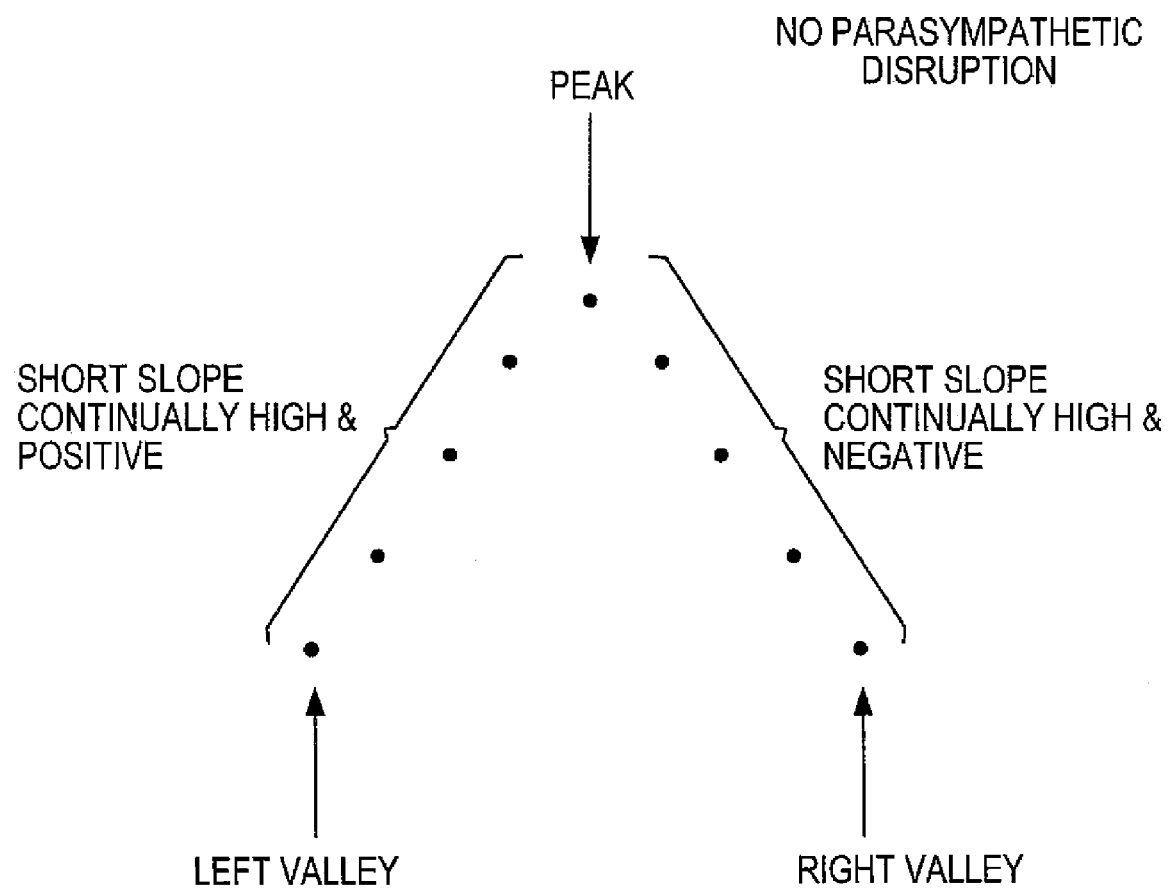
FIG. 19 illustrates an exemplary method for assessing continuity of parasympathetic activity.

The continuity of parasympathetic response may be assessed in two parts. First, the slope of every three consecutive points may be computed, for example, by starting from the left-valley point to the peak. If any of the slopes approach zero or become negative, for example, then the parasympathetic outflow was interrupted during the rising of the wave (FIG. 18). Likewise, the slope of every three consecutive points may be computed, for example, by starting from the peak to the right-valley point. If any of the slopes approach zero or become positive, for example, then the parasympathetic outflow was interrupted during the falling of the wave. If the short term slope on the left side of the wave remains high and positive, for example, and the short term slope on the right side of the wave remains high and negative, for example, then parasympathetic outflow is deemed to have been continuous, without interruption (FIG. 19).

In exemplary embodiments, the threshold for the short term slopes may be variable. Exemplary devices may keep track of the highest positive slope over the last 5 seconds, for example. Such devices may keep track of the absolute value of the highest negative slope of the last 5 seconds, for example. If the absolute value of the highest negative slope is greater than the highest positive slope, for example, that value may be used to represent the "fastest change". Otherwise, the highest positive slope may be used to represent the "fastest change".

In certain embodiments, when examining the rising of the wave, if any of the three point slopes are less than 30%, for example, of the fastest change, then parasympathetic interruption is presumed. Likewise, during the falling of the wave, if any of the three point slopes is greater than 30% of $(-1) \times$ (fastest change), for example, then parasympathetic interruption is presumed.

It should be appreciated that other algorithms may be used in accordance with the present invention to assess whether the short term slope was interrupted during the rise or fall of the wave.

Methods of Detecting Drop Points

The present invention also provides methods of detecting drop points and devices which utilize such methods. In exemplary embodiments, the drop point detection routine may run, for example, every 250 ms. Each time the, for example, 250 ms clock interrupt triggers, the device may insert a phantom value into a set of received pulse beats. In exemplary devices, phantom values are perceived, for example, as a newly received pulse the moment the interrupt was triggered. The routine then may apply a phase determination method with this phantom value in the data set. If such phase determination method assesses that the phase shifts to FALLING with this phantom value, then the drop point has been detected, because the next actual pulse will occur after the drop point. When the drop point is detected a symbol, such as a triangle, may be displayed immediately by the interrupt routine. If the test is false, no symbol is displayed. Methods utilizing such interrupt routines allow the detection and marking of drop points in real-time.

Exemplary Devices

The description below relates to exemplary embodiments of the present invention in the form of devices which may be used to evaluate and treat stress in humans. In these embodiments, RSA waves may be identified and characterized in any of the ways described above and may be used to provide biofeedback to a user. Such exemplary devices include those that provide information to users in real-time to promote the production of uninterrupted high parasympathetic output over a substantial period of time. In addition to the particular embodiments described below, it should be appreciated that other methods and devices are intended to be within the scope of the present invention. Where alternative embodiments are not explicitly described, it is not the intention of applicants to limit the present invention to the exact description provided in this section. In particular, it should be appreciated that various combinations of features described below may be incorporated into a single device and that such device will fall within the scope of the invention disclosed herein. Naturally, the full scope of the invention is based on the disclosure in the specification as a whole.

Figure 20:
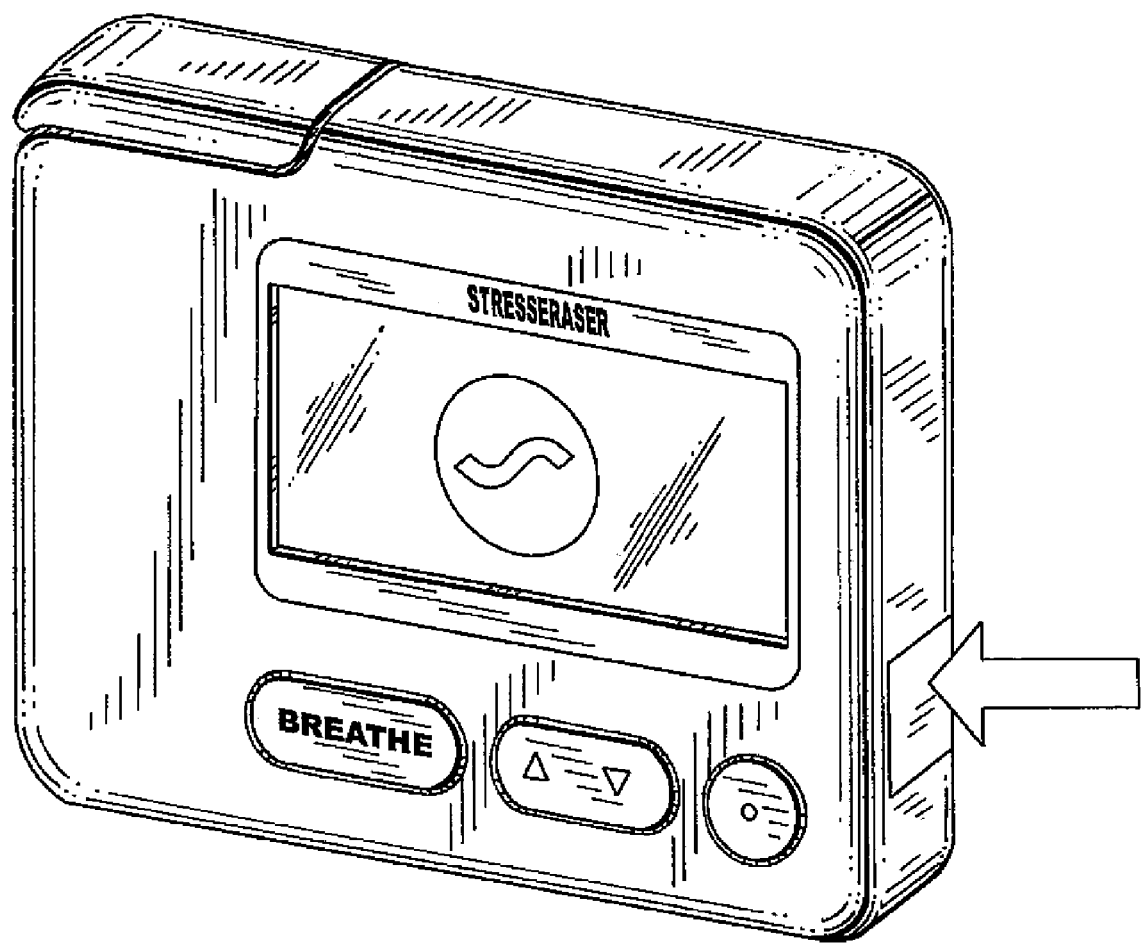
FIG. 20 illustrates an exemplary embodiment of a device in accordance with the present invention and identifies a potential location for a power switch.
Figure 21:
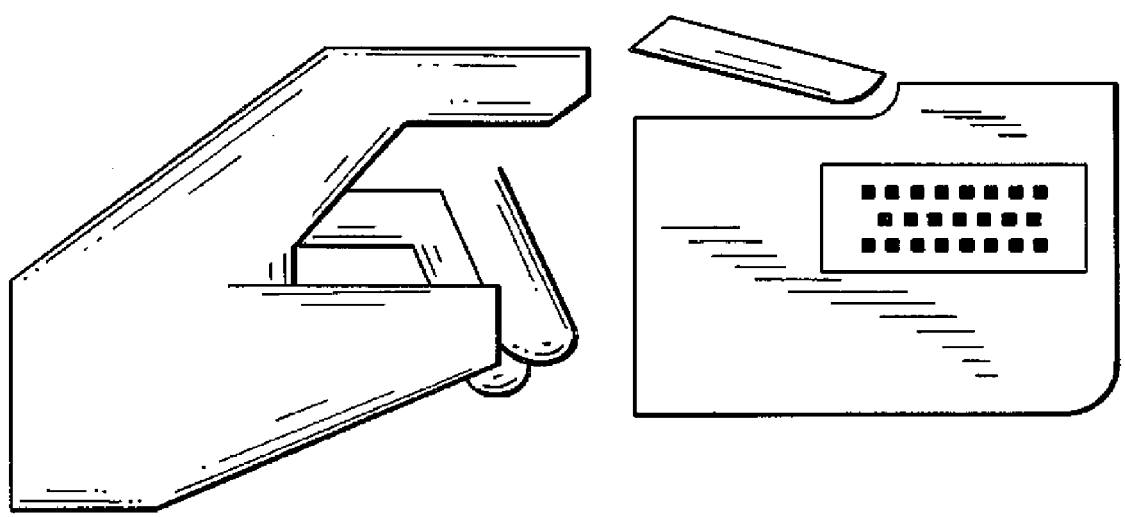
FIG. 21 illustrates a representative location for a PPG sensor which can collect data from a subject's finger.
Figure 22A:
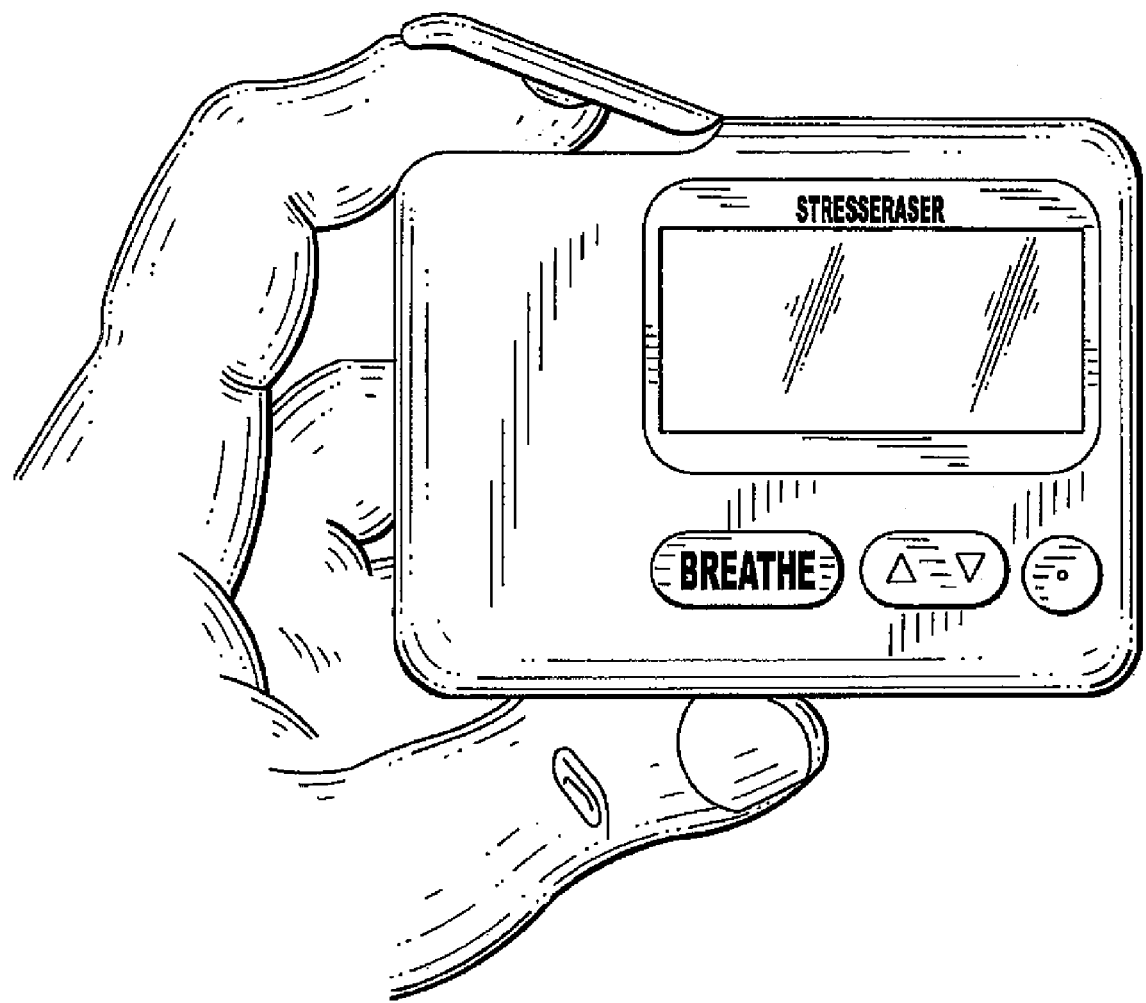
FIGS. 22(a)-(b) illustrate alternate methods for a subject to hold an exemplary device while the subject's finger is in the PPG sensor.
Figure 22B:
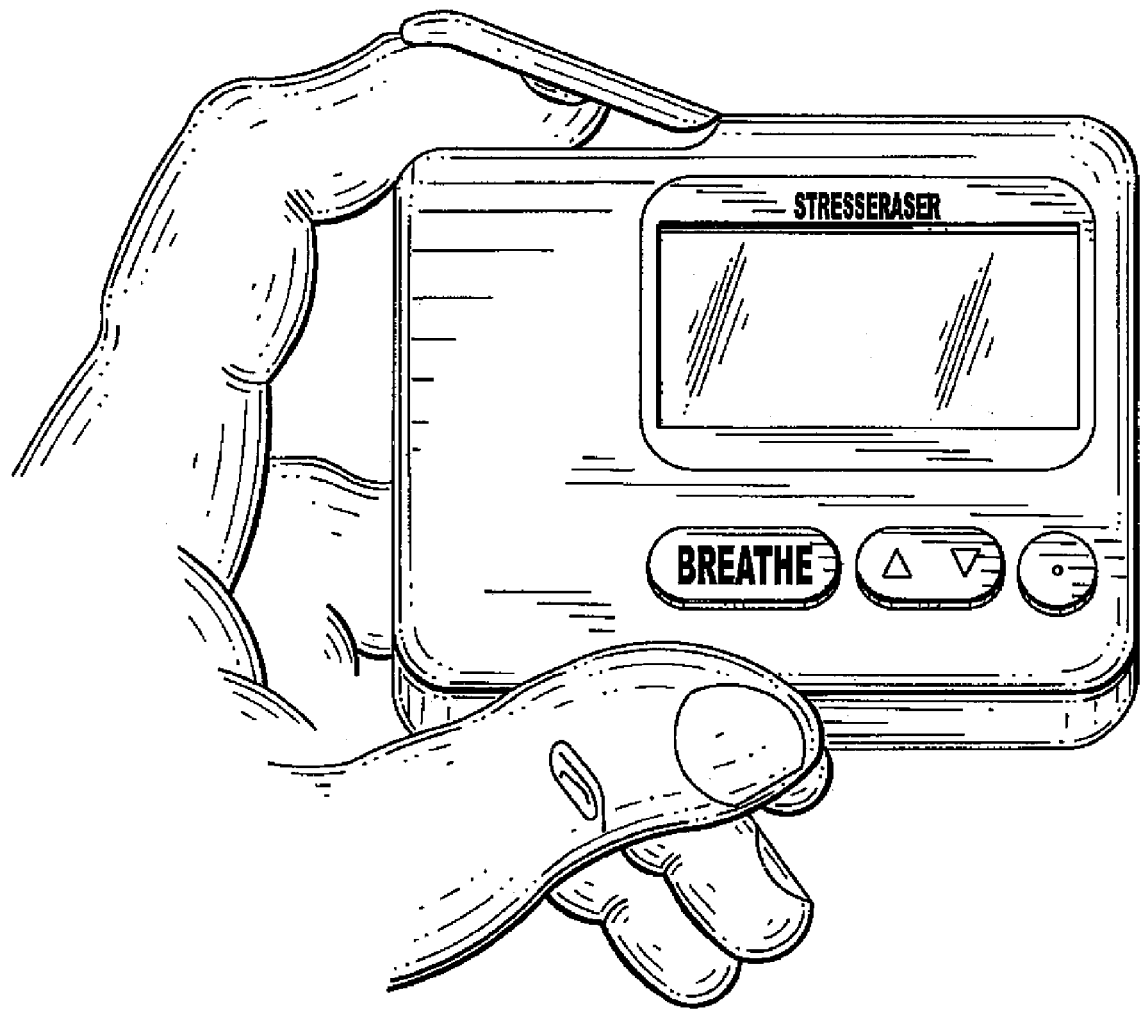

The present invention provides, for example, battery powered handheld portable devices which may include a PPG sensor, a display screen, control buttons, and a power button (FIG. 20). The user may turn on such devices by pressing a power button. If the devices are used in a dark room, the user may turn on backlighting by pressing the power button a second time and keeping it pressed for a few seconds. Soon after the device is powered on, it may prompt the user to insert a finger into the finger sensor (FIG. 21). The user then may gently hold the device with a finger resting on top of the sensor throughout the entire session. The device may be comfortably held vertically, resting on the thumb (FIG. 22a) or at an angle, resting on the curled fingers of the hand holding it (FIG. 22b).

Figure 23:
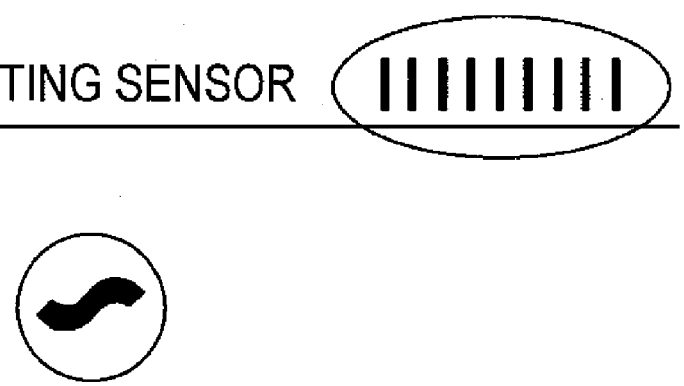
FIG. 23 illustrates an exemplary display of a countdown meter.
Figure 24:
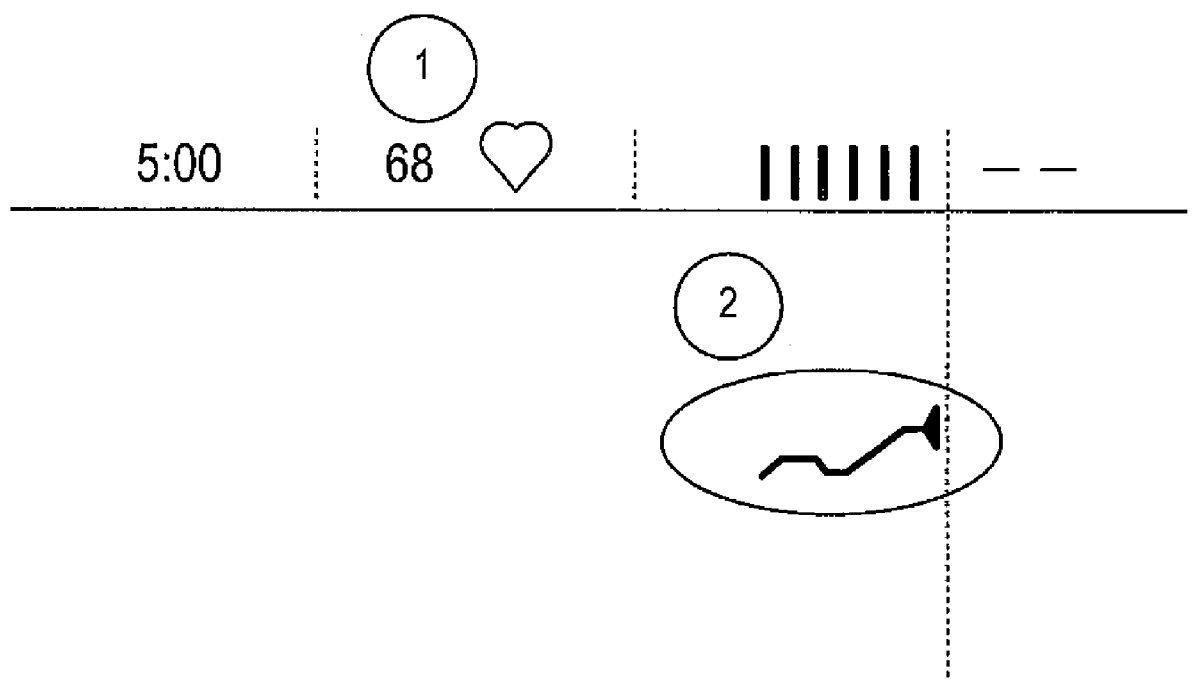
FIG. 24 illustrates an exemplary display of a representative average pulse rate as well as a pulse rate over time.

Once the finger has been inserted into the finger sensor, the device may then begin to calibrate the PPG sensor. A countdown meter may mark the amount of time required for the calibration (FIG. 23). After the PPG sensor is calibrated, the device may use the PPG sensor to detect each pulse of blood in the finger. The resulting pulse rate (60,000/number of milliseconds between two consecutive pulse peaks) then may be plotted on the screen on a pulse by pulse basis (FIG. 24(2)). The display also shows the user his average pulse rate (FIG. 24(1)).

Figure 25:
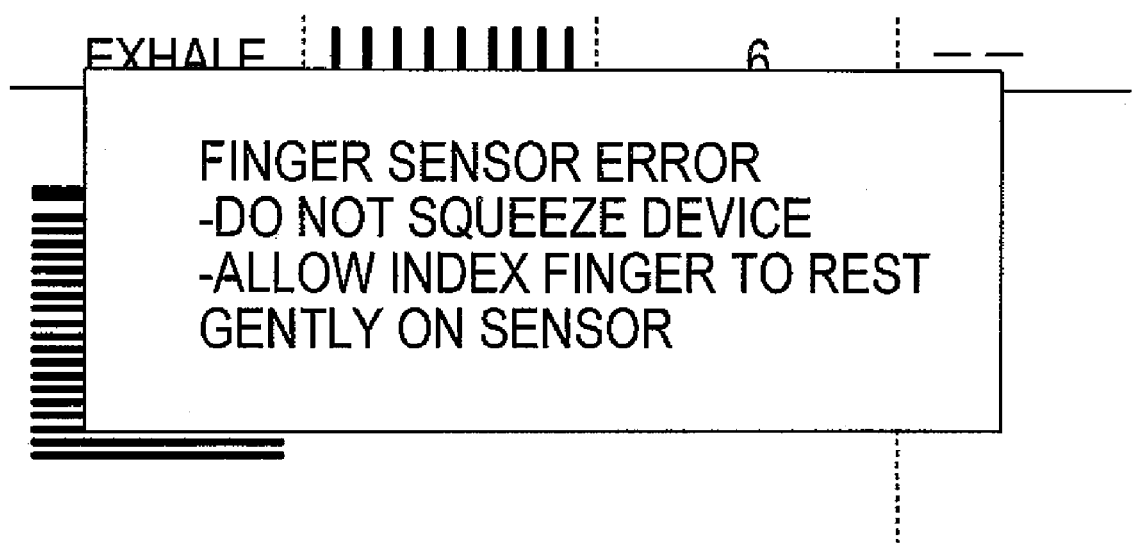
FIG. 25 illustrates an exemplary display of an error message.

PPG sensors can be very sensitive to finger pressure. That is, if the user squeezes the device, the resulting finger pressure may prevent the device from gathering accurate pulse rate information. Whenever the user applies too much pressure, the device may display an error message alerting the user to stop squeezing the device and start to relax his or her finger (FIG. 25). As soon as the user has successfully relaxed his finger, he or she then may return attention to the pulse rate display screen.

When the device identifies a new RSA wave, it may use the wave information to determine and display one or more of the following: the frequency of the last wave, the average pulse rate of all the pulse points in the wave, the session score, the remaining session time and the stress index—how much mental stress the user is currently experiencing.

The device may update the session countdown clock after every RSA wave has been identified. Devices may include a session countdown clock that decrements on a regular basis (e.g., once per second, once every fifteen seconds, etc.). In such embodiments, the device may update after each RSA wave to avoid unconscious associations being made between the clock and the desired behavior. In other words, if the clock counts down on a per second basis, the user could consciously or unconsciously use the seconds as a guide to breathing at the rate of 6 breaths per minute. Such an association may prevent the user from unconsciously learning how to breathe at 6 breaths per minute whenever becoming stressed. If the user consciously (or even unconsciously) uses the clock, he or she may always be dependent on the device. However, by updating the clock based upon every wave, such a potential situation is not only avoided, but the clock can reinforce the learning. The user will see the exact number of seconds of each breath by the amount that the clock decrements. If the clock were to decrement more slowly (e.g., once every 30 seconds), the potential for unconscious associations between time and desired behavior would be avoided. However, in such an alternative implementation, the clock would not be reinforcing the learning.

Figure 26:
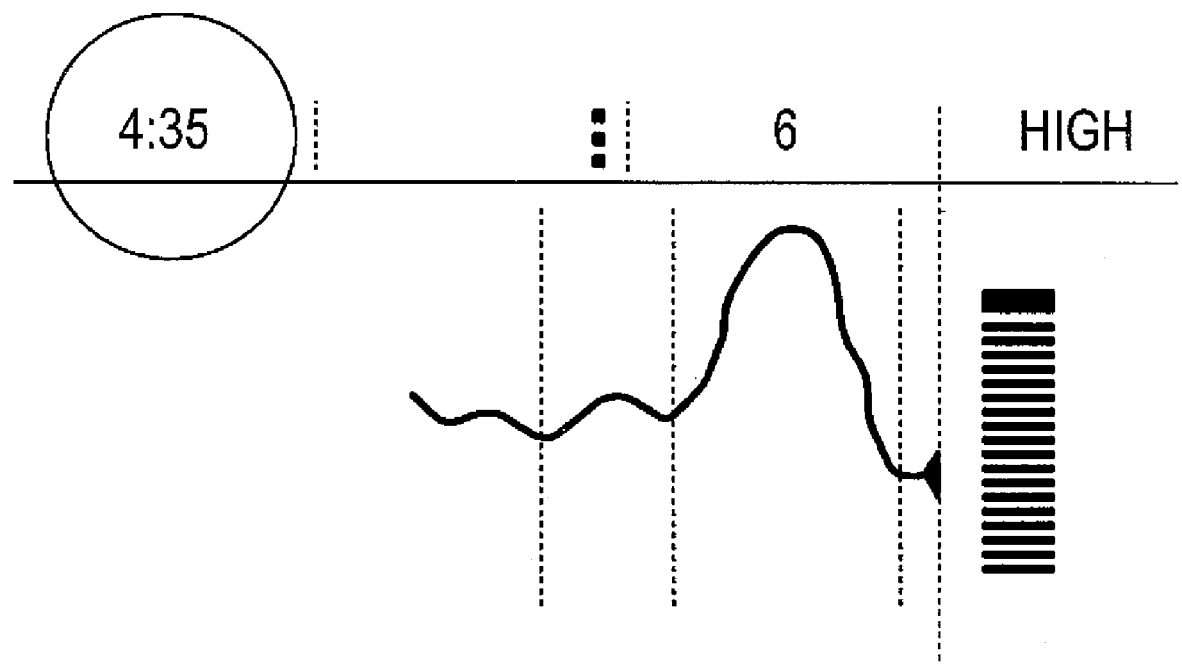
FIG. 26 illustrates an exemplary embodiment of a countdown timer.

In exemplary embodiments, the session countdown timer may begin to decrement once the first wave is identified and data is displayed (FIG. 26). However, other embodiments may begin decrementing the counter when the user begins to breathe rhythmically, or only when good waves are achieved (e.g., waves with a frequency less than six), or only while the user is practicing rhythmic breathing. Another alternative is to not decrement the counter when the breathe button is being used and guidance is being provided.

Figure 27:
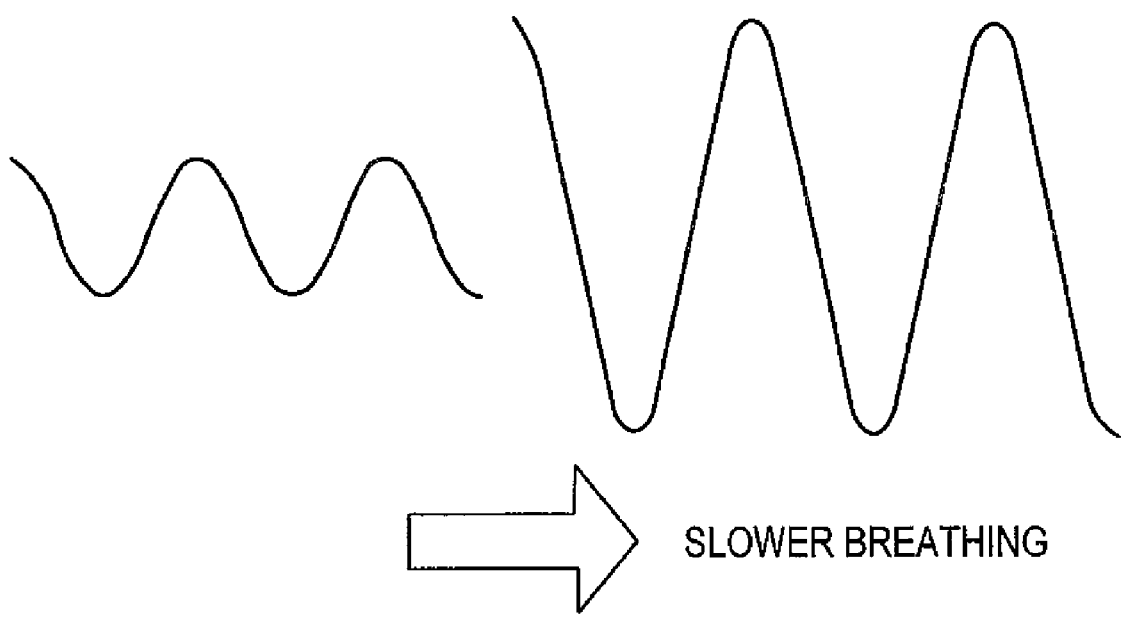
FIG. 27 provides a representative illustration of RSA waves of a subject whose breathing has slowed over time.
Figure 28:
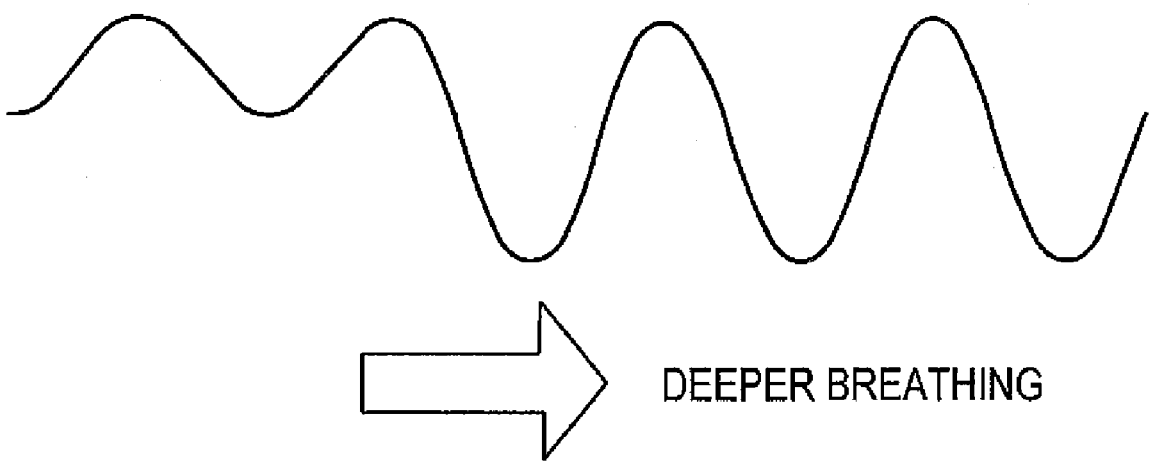
FIG. 28 provides a representative illustration of RSA waves of a subject who has taken deeper breaths over time.
Figure 29:
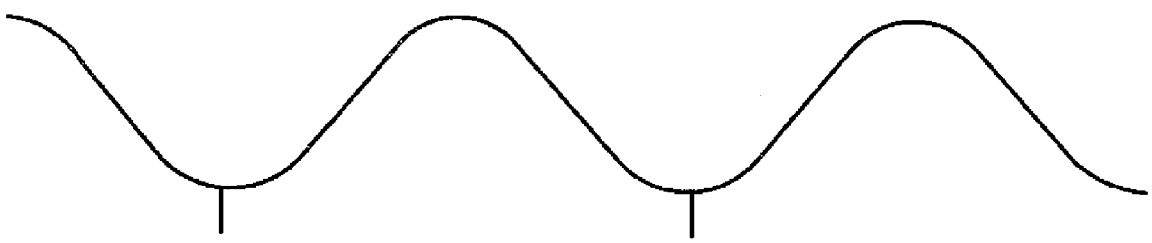
FIG. 29 illustrates a representative RSA pattern consistent with rhythmic breathing.

Users may alter the behavior of the waves, and therefore their calculated stress level, by changing their breathing pattern. As the user slows down his or her rate of breathing, the wavelengths increase and the amplitude of the waves increases as well (FIG. 27). When a person breathes more deeply, the amplitude of the waves becomes even larger (FIG. 28). When a person breathes rhythmically at a steady rate, the wavelengths entrain on the breathing rate (FIG. 29).

Figure 30:
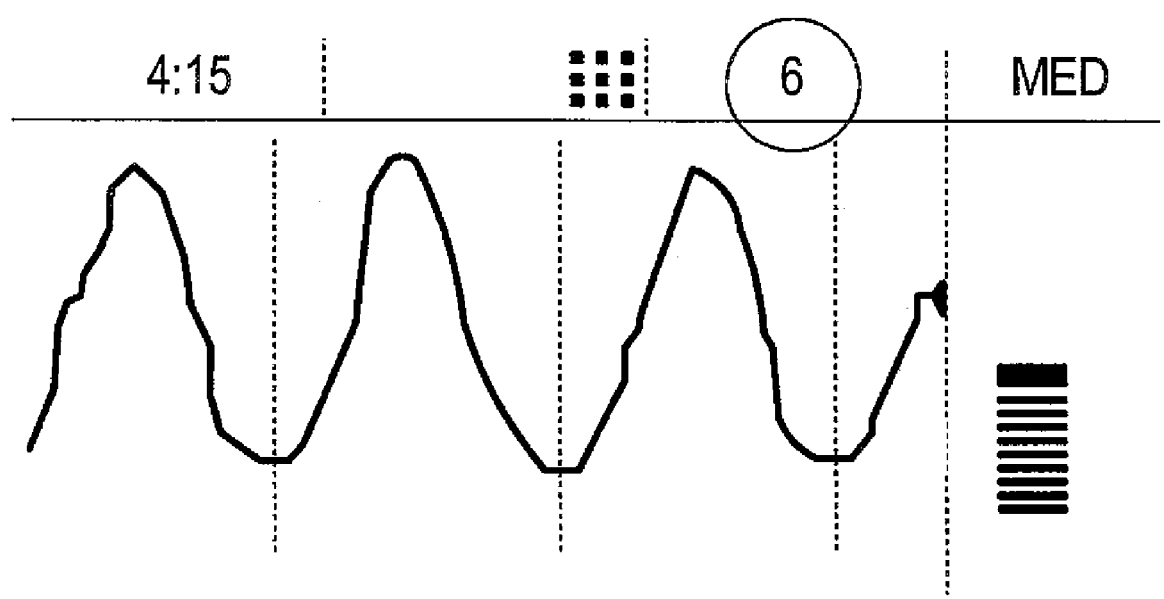
FIG. 30 provides a representative display of a subject with a wave frequency of six.

To initiate relaxation the user may begin by inhaling deeply and then slowly, letting the air out and extending exhalation. This will cause the wave lengths to become longer and therefore the frequency of the waves to decrease. The user may continue to inhale deeply and to slow exhalation even more until the wave frequency drops to about 6 (FIG. 30). If the wave frequency drops below six, then the user may breathe a little faster—that is, not exhale quite as long next time.

Figure 31:
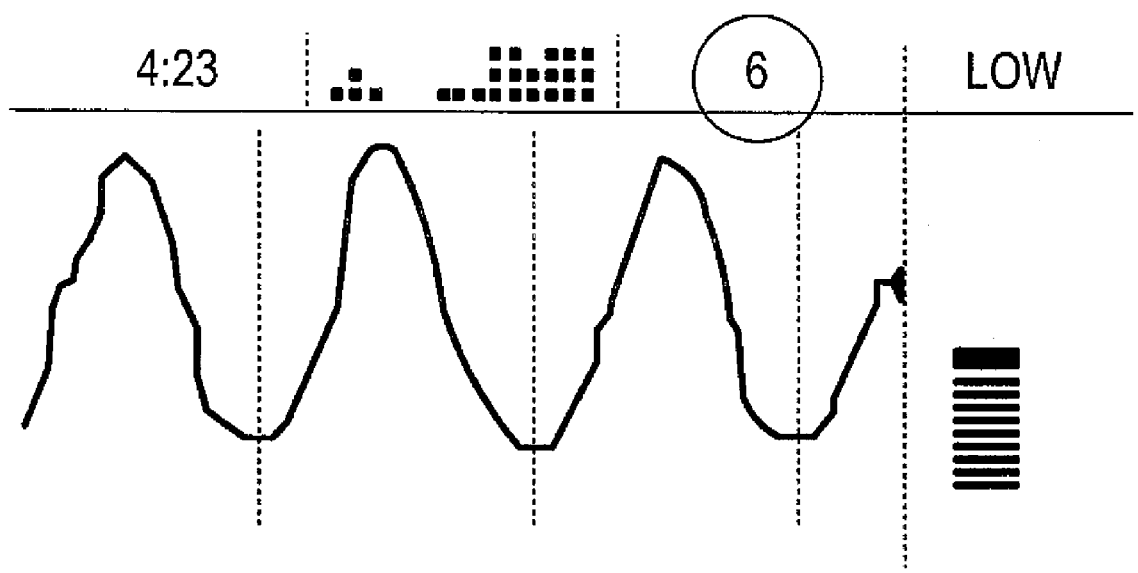
FIG. 31 provides another representative display of a subject with a wave frequency of six.

In certain embodiments, once the user has reduced the wave frequency to about 6, he or she may continue breathing at the same rate and rhythm that produced a frequency of about 6. If the user's breathing rate increases, the frequency will increase, indicating that the next breath should have a longer exhalation. If the user's breathing rate becomes too slow, the frequency will drop below about 6, indicating that the exhalation of the next breath should be a little faster. By paying attention to the wave frequency number, a user may quickly fill the screen with rhythmic waves that are about 10 seconds in length (FIG. 31) corresponding to a frequency of about 6 respiration cycles per minute.

Figure 32:
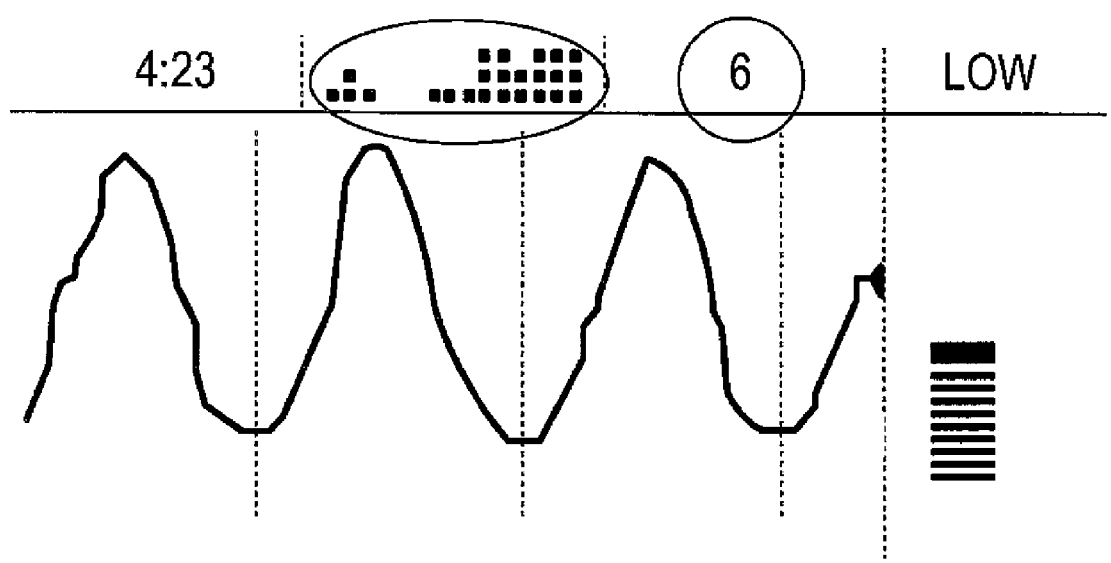
FIG. 32 illustrates an exemplary display of a subject's RSA wave history.

The session score may be calculated and displayed after each RSA wave is identified. The score may be based upon how close the user is to achieving the desired behavior. The user may accumulate score points and various methods for scoring the session may be used. In certain embodiments, the user may receive, for example, 3 points if the waves have a frequency of 6 or less. The user may receive two points for wave frequencies of 7 or 8, one point for wave frequencies of 9 or 10 and no points for frequencies greater than 10. The accumulated session score may be displayed numerically. Alternatively, each individual score may be displayed. Yet another alternative is to show the current score along side a set of the previous scores (either numerically or graphically). Certain preferred embodiments may display graphically the current score and a set of the previous scores (FIG. 32). In this way, the user can tell when he or she is breathing rhythmically. When the score display is uniform, the user is breathing rhythmically.

Figure 33:
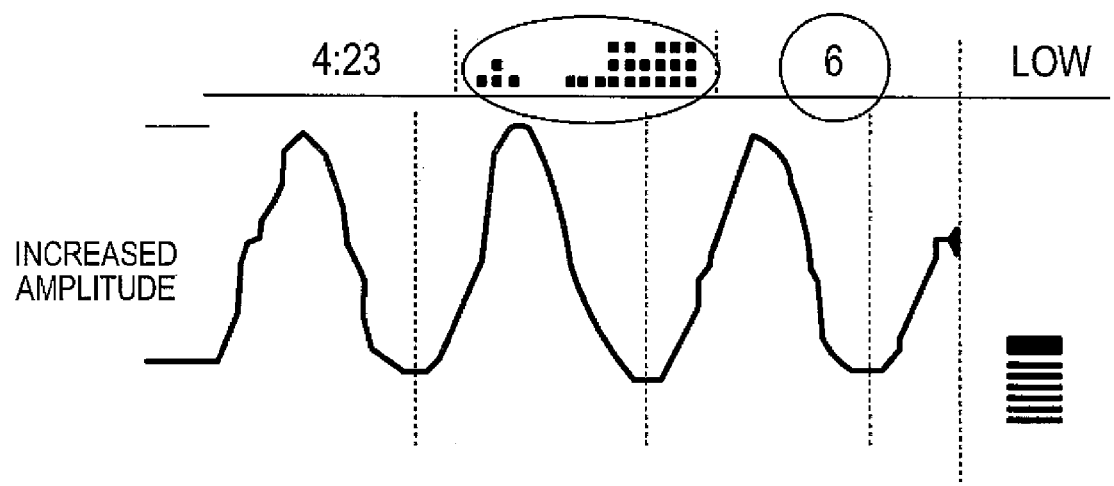
FIG. 33 illustrates an exemplary display of a subject whose depth of breathing has increased and is generated relatively large waves with a duration of about 10 seconds each.

Once the user has filled the screen with rhythmic waves, he or she may focus on inhaling a little more deeply, and exhaling a little more fully. That is, the user may attempt to inhale and exhale a greater volume of air (called "tidal volume"). As the user gently increases the depth of his or her breathing, the size of the waves will increase (FIG. 33). The user may continue to fill the screen with large waves having wavelengths of about 10 seconds each until the session timer runs out. The user then may find that he or she has achieved a very deep and profound state of relaxation.

Figure 34:
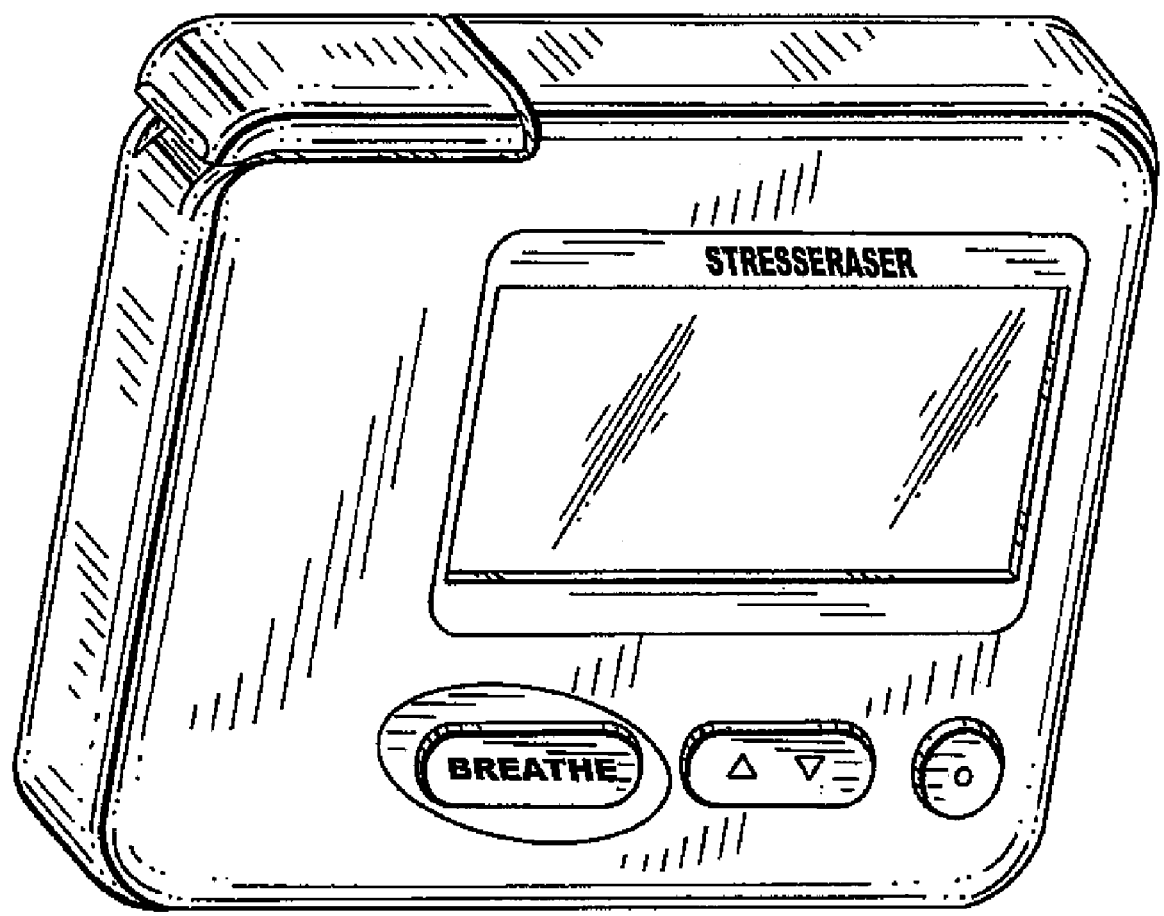
FIG. 34 illustrates a representative location for a guided breathing switch for activating a guided breathing function in exemplary devices of the present invention.
Figure 35A:
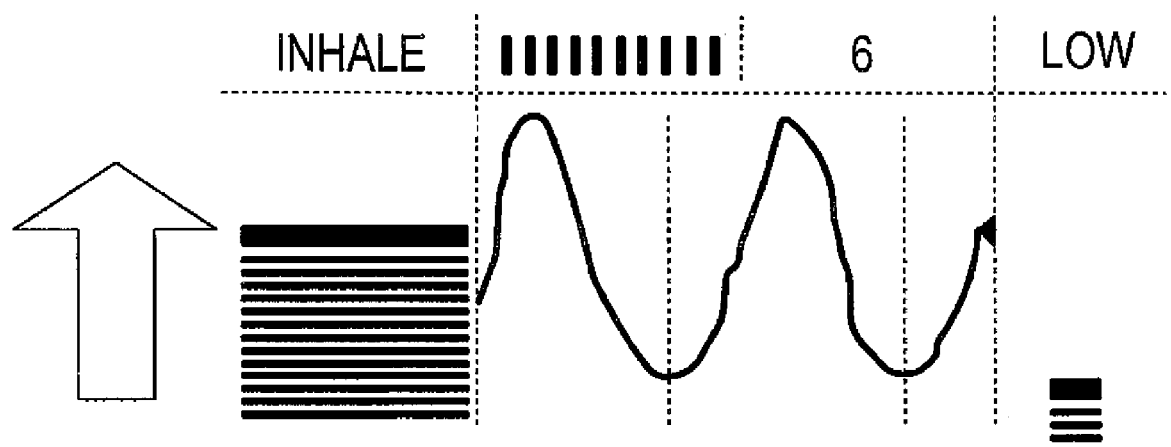
FIGS. 35(a)-(b) illustrate an exemplary display for guided breathing with a breathing bar that increases to guide inhalation and decreases to guide exhalation.
Figure 35B:
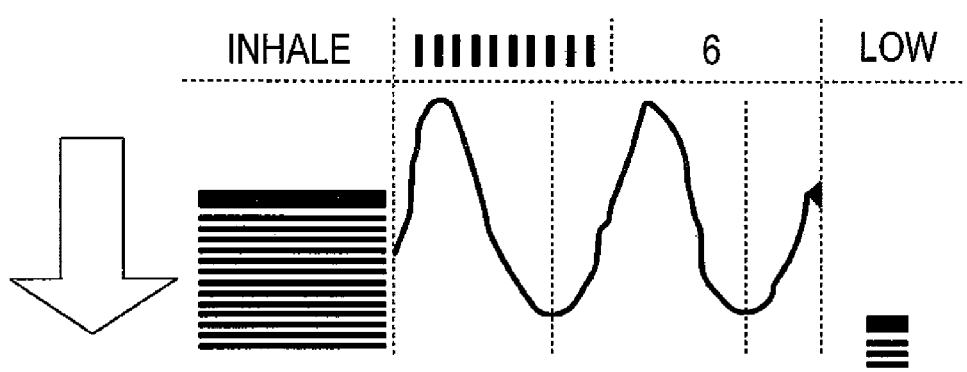

In certain embodiments, if a user has difficulty breathing deeply and rhythmically at a rate of about 6 breaths per minute he or she may obtain guidance by activating a breathing guide function. (FIG. 34). In such embodiments, as soon as a user presses the breathe button, a breathing guide may appear on the display. The user may be instructed to inhale as the breathing bar rises (FIG. 35a) and to exhale as the breathing bar descends (FIG. 35b). In exemplary embodiments, the breathing guide paces the user's breathing to about 6 breaths per minute with, for example, a 1:2 inhale to exhale ration. In alternative embodiments, the breathing guide may be programmed to provide other ratios (e.g., 1:3) at a rate of about 6 breaths per minute (e.g., 4-8/minute). The breathing guide may remain active, for example, for about one minute and then, automatically shut off thereafter. By having a temporary, rather than constant, breathing guide, the user is encouraged to use the biofeedback protocol to achieve a respiration pattern of about 6 breaths per minute. If the user were to rely solely on the breathing guide, it may be more difficult to learn how to achieve the pattern on his or her own. Thus, by weaning the user off the breathing guide, the user is able to use biofeedback to create unconscious learning. Alternative embodiments prompt the user to turn off the breathing pattern after a period of time has occurred. Other breathing rates and rhythms may be used as well.

Devices according to the present invention may return the user to the regular display after the breathing guide has been completed. The user then may adjust his or her breathing in the manner previously described to reduce the wave frequency to about 6, maintain rhythmic breathing, and increase the size of the waves by breathing more deeply. The user may continue this process until the session timer reaches 0:00, at which time the session summary screen may be displayed (FIG. 36).

Exemplary embodiments also include devices which allow the user to use up/down arrows to select the number of large waves he or she wishes to produce during a session. For example, a user may choose to generate 10 large waves during a session. The credit area may increase or decrease to accommodate the number of selected session waves.

Devices according to the present invention may continually identify individual RSA waves one at a time. The moment a new wave is identified, it may be categorized, for example, as "small," "medium" or "large." If the wave is small, a single dot may be displayed, for example, to mark it as a small wave. If the wave is of medium size, then two dots may be displayed, for example, to mark it as a medium sized wave. If the wave is large, then three dots may be displayed, for example, to mark it as a large wave. A user may be given one credit, for example, in the credit area each time a large wave is identified, and half a credit, for example, in the credit area each time a medium sized wave is identified. Of course, other values may be assigned for waves of different sizes as long as the user is provided with information about the nature of the waves he or she is producing.

In certain exemplary embodiments, at the beginning of the crest (peak) of each wave, a sound beep may indicate the size of the previous waves. If the previous wave was small, a high pitch beep may be generated, for example. If the previous wave was of medium size, then a mid-level pitch tone may be generated, for example. Otherwise, a low pitch tone may be generated, for example. The sound may be controlled by a switch such as an "(o)" button. Such a button may toggle the sound from, for example, low volume, high volume and off. A breathe feature may temporarily activate a breathing metronome to show the user one way in which he or he may breathe to generate large waves.

In some embodiments, once the user has accumulated enough credit points, the session may be considered complete and the session summary screen may be displayed. Also, a new tracking entry may be added into a tracking system.

Figure 37:
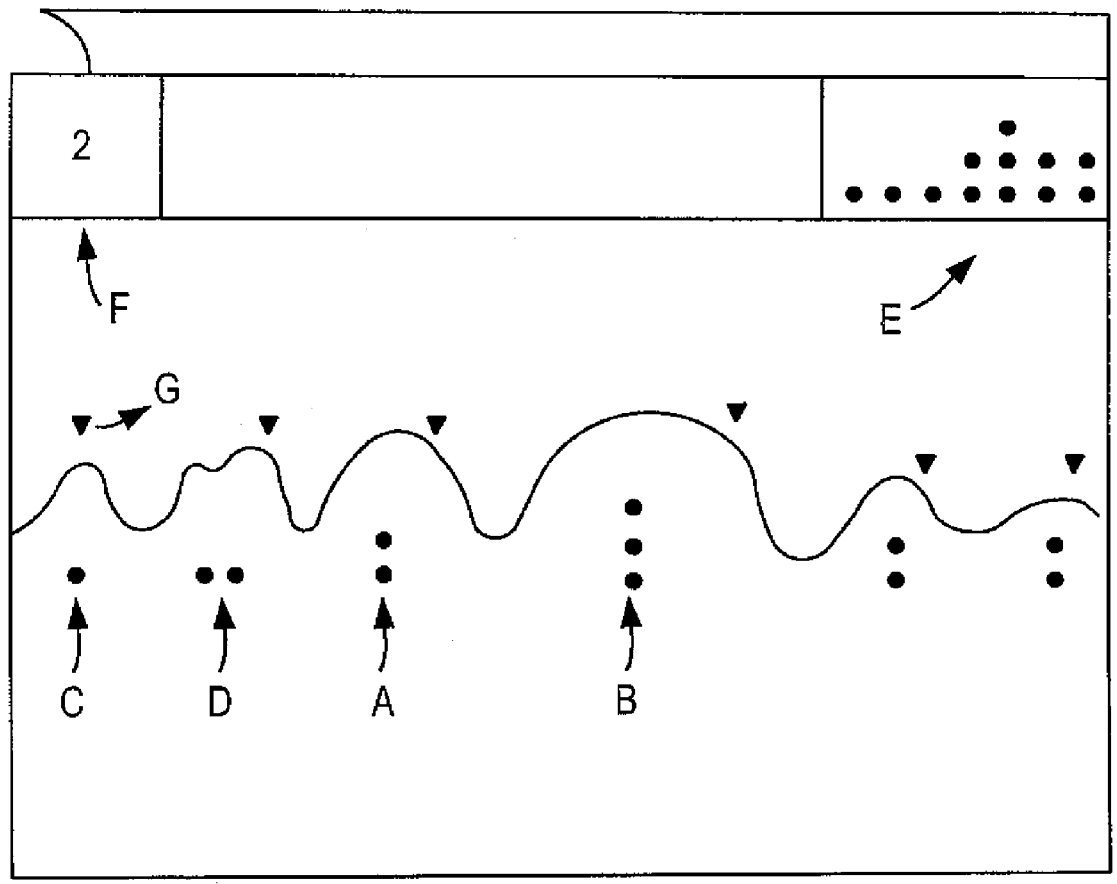
FIG. 37 illustrates an exemplary display of various types of RSA information which may be shown by representative devices according to the present invention.

In a certain embodiments of the present invention described below, biofeedback credit is based upon achieving two equally important objectives: a high level of parasympathetic intensity and a sustained parasympathetic outflow. The present invention may detect each wave of parasympathetic activity in real-time. When a new wave is complete, the device may assess both the intensity and continuity of the parasympathetic output that produced that wave. As shown in FIG. 37, if the wave was produced by a continual level of moderately strong parasympathetic activity, a two-dot symbol (FIG. 37a), for example, may be placed underneath the wave. If the wave was produced by a continual, very strong level of parasympathetic activity, then a three-dot symbol (FIG. 37b), for example, may be placed underneath the wave. If the wave was either interrupted and/or weak, a one-dot symbol (FIG. 37c), for example, may be placed underneath the wave. Two squares side-by-side may represent, for example, a broken wave (FIG. 37d). These symbols may reflect the activity of the person's parasympathetic nervous system (the stress recovery system) at the time the wave was made: very active (long wave), active (medium wave), not active (short wave) and interrupted (broken wave). These representations may be displayed in real time and provide information on the last several preceding waves (FIG. 37e). For example, the display may show representations of the last twenty waves or a number much greater or significantly less. Exemplary embodiments also may recall and display representations of waves from much earlier in the breathing session or from previous sessions.

The display also may show a cumulative total score for a specific amount of time (e.g., 24 hours) (FIG. 37f). A cumulative total score may be generated, for example, by assigning a single point for a long wave, a half point for a medium wave and no points for a short wave. The display may continue to update the cumulative total until, for example, a predetermined goal is reached, a preset time period elapses or the cumulative total score is reset. A subject may try to achieve a goal of reaching, for example, 100 points per day.

Particularly preferred embodiments of the present invention also provide novel forms of biofeedback information that can be used to induce the desired physiological state through unique breathing exercises. Such embodiments avoid drawbacks of techniques which create one or more interruptions of the parasympathetic branch on a per breath basis. For example, such breathing techniques involve extending exhalation for a very long time. In general, a longer exhale is beneficial; but when it is extended for a long period of time, long exhalations can interrupt the parasympathetic response immediately after the trough of the wave. Waiting to inhale for too long may cause an interruption right before the crest of the wave. Likewise, holding the breath for too long or inhalation that is either too long or too short, for example, can each strain the parasympathetic nervous system, causing a temporary inhibition of parasympathetic outflow.

Embodiments of the present invention overcome the above-described shortcomings by, for example, guiding the user in finding a breathing rate and rhythm that produces an intense level of sustained parasympathetic outflow. Feedback provided by methods and devices according to the present invention allows a user to maintain a substantially continual state of parasympathetic outflow, thereby suppressing sympathetic activity.

Preferred embodiments of the present invention also may indicate to the user the point at which an RSA wave transitions from cresting to descending. Such drop points may be identified, for example, by marking such point with a marker that is easily visible by a user. Such visible indicators may be in the form of a triangle, for example (FIG. 37g). Visible indicators also may be other shapes. The drop point is an ideal time to begin an extended exhale. Indicators alternatively may be audible.

By combining the feedback of the drop point with the composite parasympathetic measurement, a user may quickly learn to extend the exhale to an appropriate length to create, the highest scoring waves (e.g. a three dot wave). The user may also receive guidance to indicate when exhalation has extended too long, as the wave will break resulting in a low scoring wave (e.g., a one dot wave). Thus, methods and devices according to certain embodiments of the invention enable users to find their unique window of exhale lengths which produce a sustained outflow of intense parasympathetic activity. In use, a person simply exhales each time a new indicator appears, such as a visible triangle, and then inhales until the next indicator appears. By adjusting the length of the exhale users learn to generate perfects waves which appear during a physiological state of sustained intense parasympathetic activity.

In another exemplary embodiment, the display may provide Exhale Numbers corresponding to a number that the user may count to while exhaling. Once a breathing session begins, the subject may inhale until, for example, a drop point is indicated and then exhale while counting (preferably calmly and silently) to the Exhale Number. A timer bar may descend in an Exhale Number column for a fixed amount of time (e.g., 30 seconds, 60 seconds, etc.). The Exhale Number column may display a score from, for example, 1 to 9 corresponding to the effectiveness of the subject's breathing at that Exhale Number for the fixed length of time. A longer wave indicates more effective breathing than a shorter wave and thus may receive a higher score. The score may be based on a single wave, from all waves, or a subset of the waves. The display also may allow for the selection of alternate Exhale Numbers allowing the subject to experiment with different Exhale Numbers to find one or more which provides the best scores. As discussed above, in an exemplary embodiment the best scores are produced by the longest waves.

In certain embodiments handheld, portable devices according to the present invention may be used as follows: a subject turns a device on by pressing a power button; when prompted a subject inserts, for example, his or her left index finger into a pulse detection portion of the device; while the subject gets comfortable (e.g., subject sits upright with feet flat on floor), the sensor adjusts to the pulse rate of the user; the subject selects a target number of large waves (e.g., 5 to 100 depending on the level of stress perceived by the subject); the subject observes the pulse rate wave on the device's display as he or she breathes at a pace that is natural and effortless; while breathing slowly and deeply, preferably through the nose, the subject may observe the affect of respiration depth and frequency on the wave patterns; the subject creates long waves by exhaling slowly and for a duration approximately twice that of inhalation; long waves are tallied on the device's display, while waves that are not long are not tallied; beginners may press a breathe button on the device to help pace the subject to create long waves (e.g., a pacer can appear for a certain number of breathes which may or may not be tallied); an intermediate user may view the drop point indicator in the monitor and exhale at the drop point and inhale during the rise of the next wave; advanced users may press a sound button and use the device with eyes closed, exhaling each time the device makes a certain sound at the drop point, while the pitch of the sound may further indicate whether the previous wave was credited an added to the tally.

Several aspects of the present invention can be combined together to create a number of alternative exemplary embodiments. For example, the device can feature a meter that could be used as an amplitude feedback meter rather than a stress meter. The meter could further have a target bar. Thus, the device could graphically display how deeply a person is breathing so he could learn to take deeper breaths. If a target bar is used, users could try to breathe deeply enough with each breath to cause the meter to rise above the target bar. Any numerical or graphical feedback (visual or otherwise) of amplitude would be within the scope of this alternative embodiment.

Other alternative embodiments may use wave information (e.g., wavelength, amplitude, and peak placement) to determine and provide feedback regarding the degree to which a user is following a prescribed breathing protocol (e.g., 6 breaths per minute with an inhale:exhale ratio of 1:3). Alternatively, the user could be given a breathing guide while being provided simultaneous auditory or visual feedback on how closely they are conforming to the guided breathing pattern. Furthermore, a target level could be displayed such that a user would be considered compliant if he were above the target level and non-compliant with the breathing protocol if he or she were below the level.

Alternative embodiments also may use the variance of one or more wave parameters to detect rhythmic breathing. Then, the degree of rhythmic breathing may be visually displayed numerically, graphically, or in some other manner. Optionally, audible feedback may be provided. For example, in an exemplary embodiment a tone can increase as the breathing becomes more arrhythmic and decrease as it became more rhythmic. Alternatively, a single beep can indicate rhythmic breathing, a double beep can indicate near rhythmic breathing, and a triple beep could indicate arrhythmic breathing. Naturally, any of the previously mentioned feedback techniques or derivatives of these techniques could be used independently, in combination with each other, in combination with other techniques, or in combination with both each other and other techniques. Such an implementation may be used, for example, to practice yoga style rhythmic breathing patterns. For example, if the yoga student were practicing rhythmic breathing at an inhale:hold:exhale ratio of 1:1:1, he or she could use the device to ensure that rhythmic breathing was being maintained.

In other embodiments of the present invention, a pre-programmed breathing guide can be provided on the device so the user could follow the breathing guide while receiving visual and/or auditory feedback on the rhythmicity of his breathing. Furthermore, the breathing guide could be programmable. Optionally, feedback can be provided not only on the rhythm of the breathing, but rate as well. For example, if the user wanted to practice breathing at a 1:1:1 ratio at 5 breaths per second, visual and/or auditory feedback can indicate the degree to which a user is breathing rhythmically at five breaths per minute. Breathing at another frequency and/or arrhythmically would reduce the score.

Another exemplary embodiment provides feedback on the depth of breathing. During rhythmic breathing, a measurable phenomenon using aforementioned methods, the primary difference in wave amplitudes is the tidal volume (the depth of breathing). Thus amplitude measurements could be used for visual and/or auditory feedback to indicate the depth of a person's breathing. As stated previously, deep breathing is a useful way of relieving stress. Exemplary embodiments can provide feedback on a user's depth of breathing to assist teaching the user how to breathe deeply and to thereby relieve stress.

In short, exemplary embodiments of the present invention can provide auditory and/or visual feedback for the following: rate of breathing, rhythmicity of breathing, depth of breathing, breathing conformance to a prescribed rate/rhythm, transition points from cresting to descending (e.g., drop points) and the like. An assessment can be made of each of these, alone or in any combination. Feedback can be provided on one or more of such assessments. Any implementation that identifies two or more RSA waves and derives rate, rhythm, depth, and/or conformance is within the scope of the present invention.

Exemplary Form Factors

Exemplary embodiments of the present invention incorporate a number of features in addition to those described above. One such feature is the design of the device form factor. Prior to the present invention, biofeedback programs used finger PPG sensors, ear PPG sensors, and/or heart rate ECG sensors that attached to a computer via a wire. Although PPG sensors are sensitive to movement and finger pressure, prior devices did not have to deal with the many artifacts created by movement or excessive pressure because they used finger PPG sensors which were often placed on tables or desks. In this situation, users could rest their hands and fingers on the desk which stabilized the hand and finger, thereby preventing excessive movement and finger pressure.

Since external wires are generally socially (and otherwise) unacceptable, exemplary embodiments of the present invention integrate a PPG sensor directly into portable devices and eliminates external wires. As a result, devices according to exemplary embodiments of the present invention may be used comfortably in a public setting. Integrating a PPG sensor into a portable device, however, requires innovative form factors. For example, since session times may range from 5-15 minutes or may, users of the device will be holding the device, without a stabilizing structure like a desk, for an extended period of time. Accordingly, the present invention provides devices which may be gripped comfortably, while simultaneously allowing the user to gently rest his finger on the finger sensor.

Figure 38:
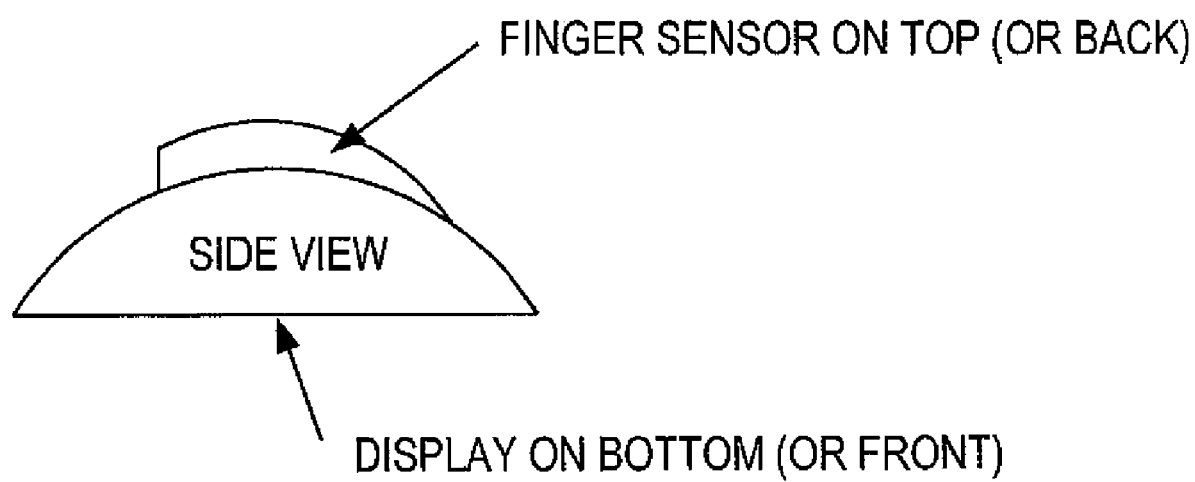
FIG. 38 illustrates an alternate form factor for exemplary devices of the present invention.

The present invention also provides form factors that provide comfort while minimizing artifacts caused by movement and pressure over extended periods of time (e.g., 10-15 minutes). Two exemplary form factors accomplish these objectives. In the first, the finger sensor may be on the top of the device near one of the edges. Ergonomically, the height from the bottom of the device to the top may be between about 1.5 inches and about 3.5 inches and is preferably around 2.5 inches. This allows the device to be supported either by the thumb when held vertically (FIG. 22*a*), or supported by the curled fingers when tilted (FIG. 22*b*). In the second, the finger sensor is located on the rounded back of the device with the display on the front, allowing the device to rest, for example, in the palm of the hand during use (FIG. 38). The particularly preferred form factor is the first-described above which allows for the design of products with a scientific and medical look and feel.

Methods of Error Detection and Correction

The present invention also provides methods for detecting and correcting errors in devices described above and devices which utilize such methods. While either of the above-described form factors minimizes artifacts, the hardware form factor may not eliminate every possible artifact. Because there is no supporting structure such as a table or desk, the hand and finger will move at different times throughout the session. Remaining artifacts may be addressed by software in exemplary embodiments of the present invention which may not only detect when an error has occurred, but may correct it as well.

Figure 39A:
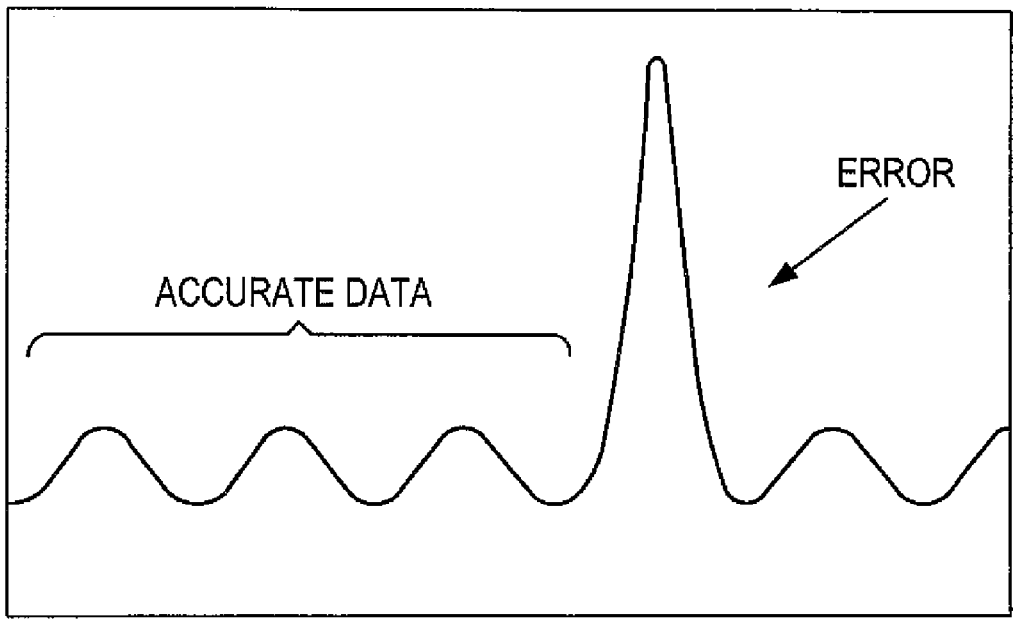
FIG. 39(a)-(b) illustrate, respectively, a display having sufficient size to show both accurate data and erroneous data and a display of a small, portable device in which only the erroneous data is discernible.
Figure 39B:
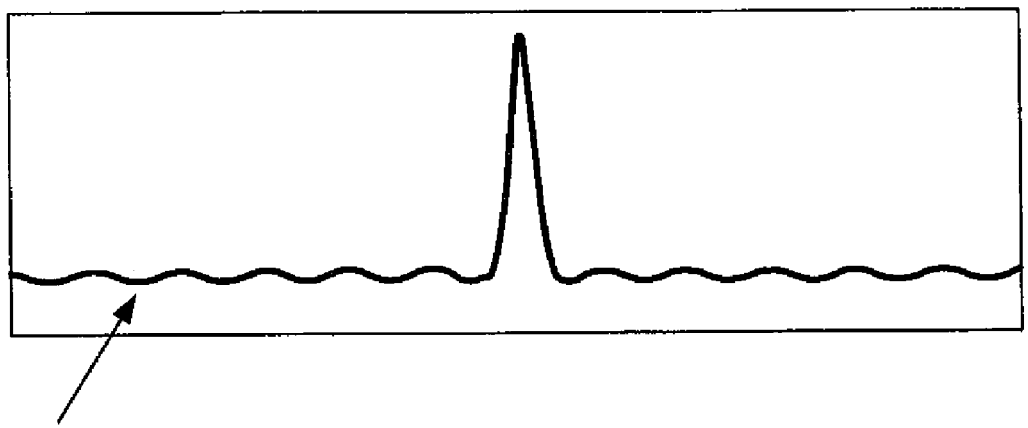

In general, displays on small portable devices are much more sensitive to errors because such displays are very small compared to that of a desktop computer, for example. When an error occurs on a desktop computer, the display has enough resolution to show both the accurate data and the error (FIG. 39*a*). On a small, portable device, however, one error can cause all the correct data to become indiscernible due to its low resolution (FIG. 39*b*).

Numerous statistical methods for detecting errors in a data stream exist in the state of the art. However, these methods require a large sampling of data before they provide a high degree of accuracy. As mentioned above, devices having small displays can be adversely affected by even a single error. Thus, errors should be detected quickly and accurately and then corrected. Devices according to an exemplary embodiment of the present invention implement a novel method of error detection and correction that requires only a small amount of data (approximately 10 seconds) before it becomes highly accurate.

Figure 40:
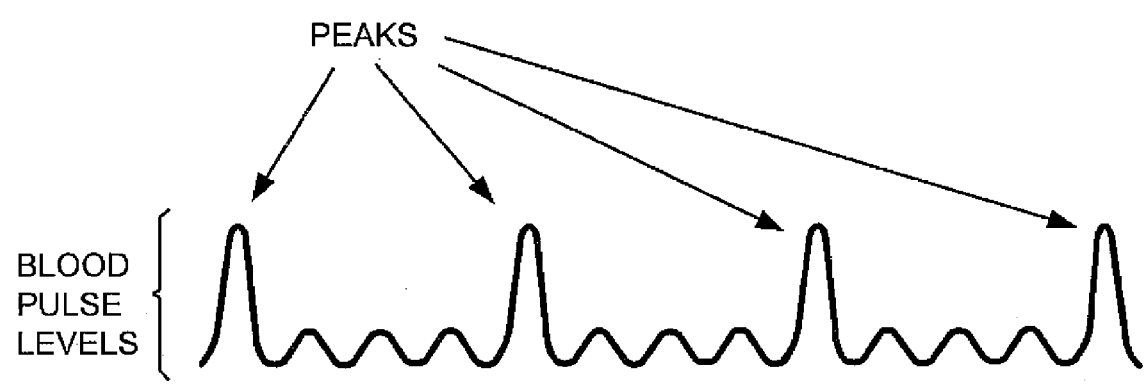
FIG. 40 illustrates a series of representative pulse peaks.

To facilitate further understanding of the error detection and correction methods of the present invention a brief explanation of how PPG sensors are used to obtain pulse information in ideal, error-free conditions is provided. PPG sensors detect the amount of blood pressure in the finger on a continual basis. Each time the heart beats, the corresponding pulse of blood results in a rapid increase in blood pressure in the finger, which then quickly subsides. The PPG sensor continually seeks to identify the time when the blood pressure peaks (FIG. 40). This is the pulse peak. As discussed previously, the amount of time (in milliseconds) between two consecutive pulse peaks is called the pp interval (pp). Devices according to the present invention can record each successive pp interval. The pulse rate of each recorded pp interval (60,000/pp) can be displayed on the screen each time a new pulse peak is encountered. The absolute time difference between successive pp intervals (absolute (pp[n]-pp[n−1])) is called the interbeat interval time or IBI.

Figure 41A:
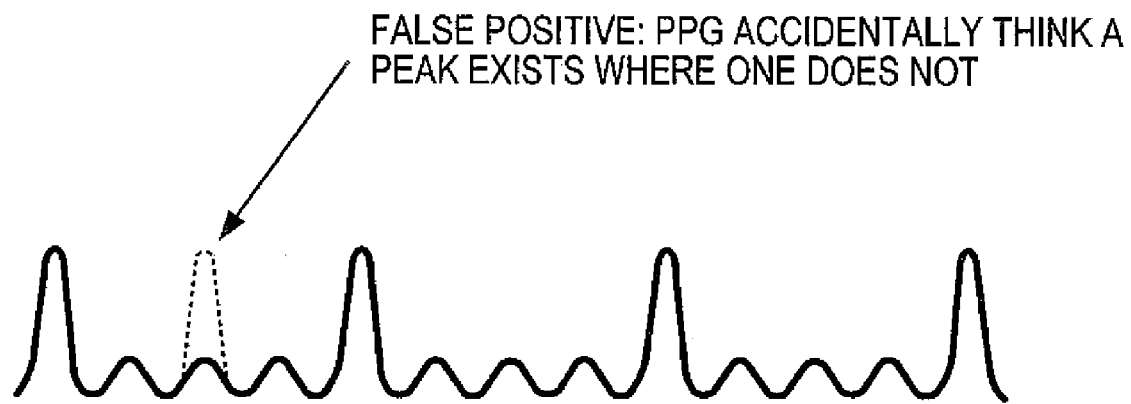
FIG. 41(a)-(b) illustrate, respectively, a representative false positive pulse peak and a representative false negative pulse peak.
Figure 41B:
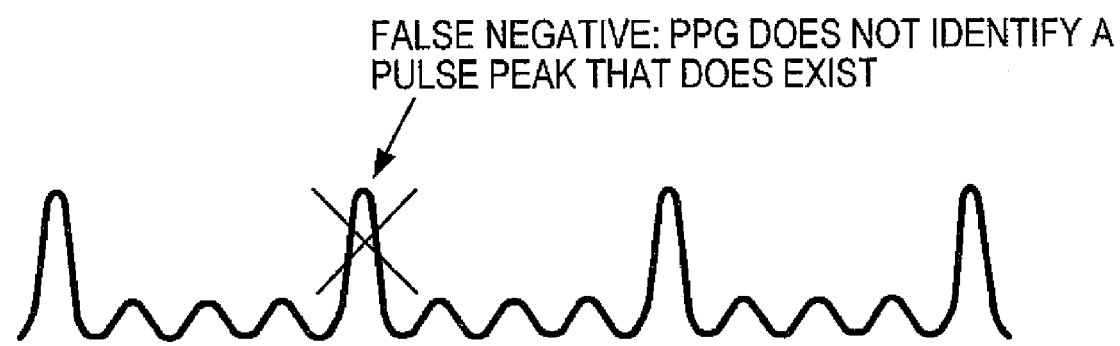

Two types of errors occur when the PPG sensor is attempting to correctly identify the next pulse peak. (FIG. 41) One type of error can occur when the PPG sensor incorrectly identifies an artifact as a pulse peak. That is, the PPG sensor determines that a pulse peak occurs where one does not actually exist (FIG. 41*a*). This type of error is called a false positive error. The second type of error occurs when the PPG sensor does not identify a pulse peak that does exist (FIG. 41*b*). This is called a false negative error. Both false negatives and false positives result in large IBIs. Error free data may or may not result in large IBIs. However, erroneous data always produces a large IBI. Thus, wherever there is an extended amount of consecutive data that does not contain a large IBI, one can safely assume that this data is free of errors. Where large IBIs occur, it may be due to an error or may be good data; the device will need to determine which is the case.

According to preferred exemplary embodiments of the present invention, the first step in the error detection strategy is to wait for a certain number of heart rate related intervals (e.g., 10 pp intervals) where every IBI time is less than 200 ms. These data points are considered to be error free. The number of consecutive intervals can be less than 10 but needs to be at least 2, preferably at least 3 and even more preferably at least 5. Another alternative is to wait for a set of consecutive data points where every IBI time is less than ⅓ of the lowest heart rate related interval, such as a pp interval, in the consecutive data set (e.g., 5 consecutive pp intervals). The range of these data points can be computed. As used herein, "range" can refer to the absolute range (i.e., min pp to max pp), a derivation of the range (e.g. ((min pp−10%)-(max pp+10%)), or as a computed variation (e.g. mean deviation, standard deviation, etc.). Any appropriate mathematical description of the range can be used. Preferred embodiments according to the present invention use min pp−((max pp-min pp)×25%) as the bottom of the range. The preferred embodiment uses max pp+((max pp-min pp)×25%) as the top of the range. The range may be derived from the entire data set or a subset of the data set.

Once the range has been established, each new p-p is tested to determine if it is "in range". In exemplary embodiments, a new pp value is considered "in range" if it is greater than the bottom value and less than the top value. However, "in range" also can refer to any mathematical determination of close proximity of the current p-p to the range as determined by the selected range calculation. For example, if the range was calculated using the standard deviation, "in range" could refer to the statistical determination that the current p-p has an 80% or higher probability of being within the computed variation.

As new pp intervals arrive, the new IBI also may be computed (absolute new pp-previous pp). The new IBI may be tested to determine if it is "large". In preferred embodiments, the device tests whether the IBI is greater than one half the bottom value of the range. If it is greater, the IBI is considered to be large. In other exemplary embodiments, the IBI time of the new pp interval minus the previous interval can be computed. Other IBI times could be used instead, such as the IBI of the new p-p compared to the average p-p of the last n number of pp intervals. Also, different implementations can use a different threshold for distinguishing large IBIs from non-large IBIs. According to embodiments of the present invention, any implementation can be used that uses the difference of pp intervals or the difference of a derivative of pp intervals (such as the average) in order to detect an error.

To summarize the above, when the device according to exemplary embodiments of the present invention begins, it may not enter error detection mode until 10 consecutive pp intervals are located where all the IBI times are less than 200 ms. Then, the device can calculate the range of these pp intervals and initiates an error detection mode. In the error detection mode, the device can test each new pp to determine if it is "in range" and the device tests each new IBI to determine if it is "large". Any other suitable method of determining either or both of these two properties for use in error detection also is within the scope of the present invention.

If the next p-p is "in range" and the IBI is not "large", then the new p-p can be considered to be error-free. If the p-p is not "in range" and the IBI is not "large", the new p-p can be considered to be error-free and the range is recalculated to include the newly found pp value. If the new p-p is "in range" but the IBI is "large", the new p-p can be considered to be error-free. However, when the new p-p is "out of range" and the IBI is "large", then the new p-p can be considered to be the result of an error. Once an error has been detected, it should be corrected. Therefore, each time that an error is detected in error detection mode, the device changes to error correction mode. The device can remain in error correction mode until erroneous condition has been resolved.

Figure 42:
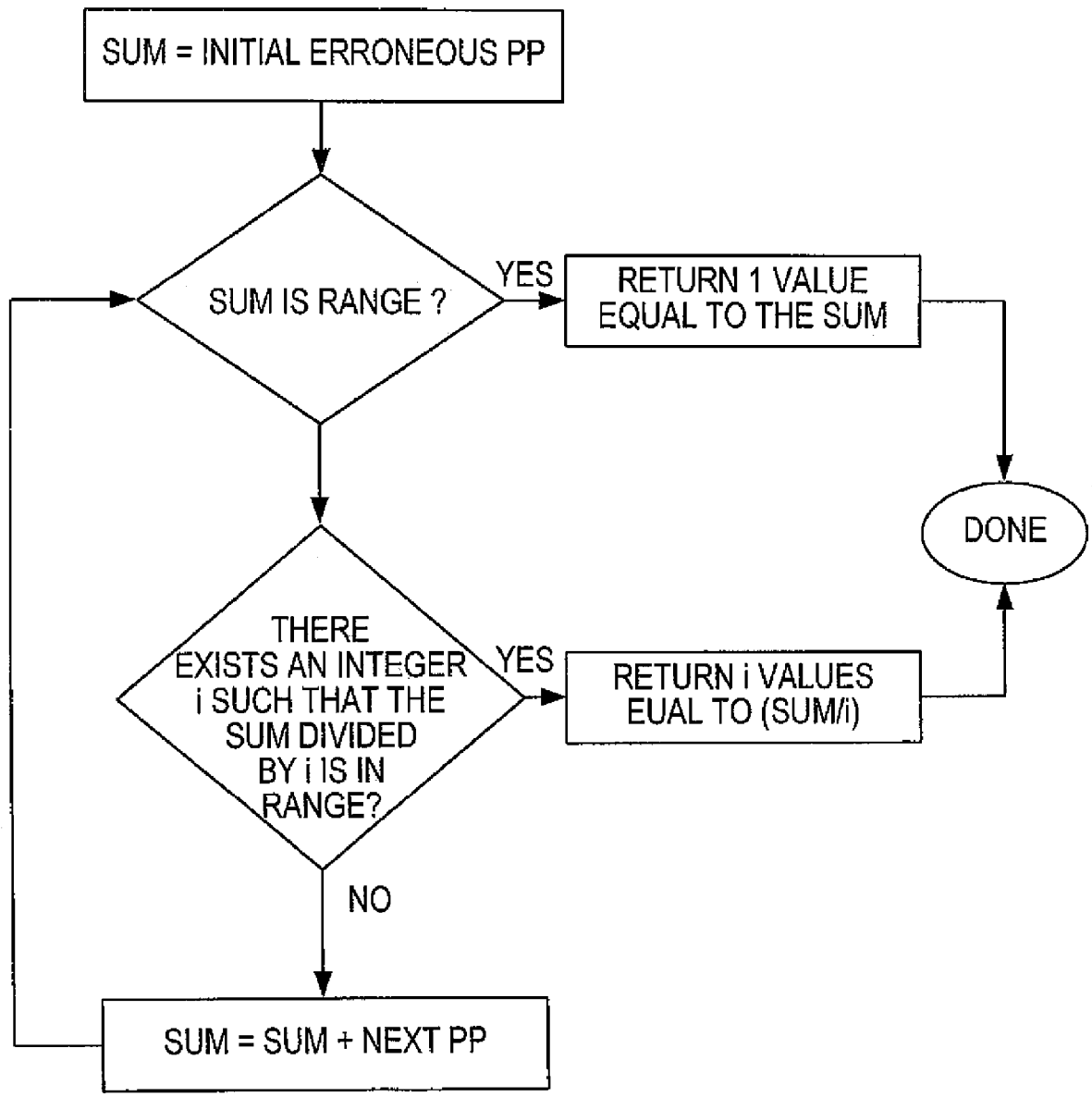
FIG. 42 depicts an exemplary process flow for an exemplary error correction method employed during a representative error correction mode.

FIG. 42 provides a flowchart showing an exemplary error correction methodology employed during an error correction mode. Error correction includes summing together each successive pp interval as it is identified until either the sum of the pp intervals is "in range" or the sum can be divided by an integer such that the result of the division is "in range". When the sum itself is "in range", all the pp intervals forming the sum can be combined together into a single value equal to the sum. When the sum divided by an integer is in range, the erroneous values can be replaced with n (where n=the integer denominator) number of values equal to the result of the division.

The following discussion provides examples of how errors may be corrected according to an exemplary embodiment of the present invention. For example, if the range is 600 ms-1,000 ms, and the erroneous pp interval time is 200 ms. The next pp interval is 100 ms. The sum is now 300 ms. It is not "in range". The next pp interval is 400 ms. Therefore the sum is now 700 ms. It is "in range" and therefore 700 ms is the corrected value. The three pp intervals (200 ms, 100 ms, and 400 ms) will be combined into one value of 700 ms. The device then returns to error detection mode.

As another example, if the range is 700 ms-1,000 ms, and the erroneous pp interval is 1,300 ms. There are no integers which one can divide 1,300 ms by that will result in a value "in range". Therefore, the next pp interval (300 ms) is summed together to produce 1,600 ms. At this time, there is an integer which can be used in a division to produce a value "in range". The integer 2 results in a value that is "in range" (1600/2=800 ms). Therefore, the two erroneous values (1,300 ms and 300 ms) will be replaced with two (the integer number) values of 800 ms (the result of the division).

In exemplary embodiments, devices according to the present invention will be able to generate corrected values within one or two additional pp intervals. However, it is possible that a device may enter error correction mode indefinitely. Therefore, the present invention can include a safety mechanism to resolve this situation if it should occur. For example, if the device remains in error correction mode for too long, then the device recalculates the range by applying a statistical method to all original data points encountered. That is, every unprocessed pp interval received from the PPG sensor is used. The range is then computed with a statistical based range calculation, for example, a standard deviation formula. In exemplary embodiments, the median pp interval is determined from all unprocessed pp intervals encountered (whether authentic or erroneous). The range is defined as 15 beats per minute below the median up to 15 beats per minute above the median. The pp intervals in the error queue are reprocessed according to the new range. Note that the range could also be computed with a subset of the unprocessed data points (e.g., the last 50 data points). The present invention also can include any method of recalculating the range to resolve an extended error condition.

As stated previously, PPG sensors are sensitive to movement and finger pressure. They are also sensitive to bright light and cold fingers. Therefore, there are a number of factors that can cause multiple errors. In certain embodiments of the present invention, whenever the signal to noise ratio over ten seconds drops below 25%, the device may cycle a display of error messages (such as that shown in FIG. 18) until the device exits from error correction mode. Thus, the user will be provided information on changes can be made to assist the device in gathering accurate pulse information.

The present invention also provides alternative methods for detecting and correcting errors in a heart rate interval data set. For example, there are a number of implementations that would permit the range and/or IBI thresholds to dynamically change as new heart rate interval values were detected. Such implementations may provide a marginal increase in accuracy in certain circumstances.

For example, the range may be continually assessed using a rolling window. The range may be initialized after receiving the first 10 seconds of pp intervals such that each consecutive IBI is less than 200 ms. After this point, the range could be continually reassessed using a rolling window of the last 10 seconds of reliable data. The last 10 seconds of reliable data may or may not be consecutive. For example, the top of the range (r_top) could be the highest p-p in the last 10 seconds of reliable data and the bottom of the range (r_bottom) could be the lowest p-p in the last 10 seconds of reliable data.

Another alternative is to dampen the rate in which the range can dynamically expand and contract. For example, each time a new pp value is detected, the range could be updated in three steps. First the data set top (ds_top) and the data set bottom (ds_bottom) are identified from the last 10 seconds of reliable data. Second, the ds_top and ds$_{13}$bottom are adjusted in a manner such that they do not change significantly from the previous ds_top (p_ds_top) and the previous ds_bottom (p_ds_bottom). For example, if the p_ds_top is greater than ds_top, then ds_top could be reset to p_ds_top−((p_ds_top−_ds_top)/25+1). If p_ds_top less than ds_top then ds_top could be reset to p_ds_top+((ds_top−p_ds_top)/4+1). If p_ds_bottom is greater than ds_bottom then ds_bottom could be reset to p_ds_bottom−((p_ds_bottom-ds_bottom)/2+1). If p_ds_bottom is less than ds_bottom then ds_bottom can be reset to ((ds_bottom-p_ds_bottom)/25+1). Thus, r_top would be equal to the adjusted ds_top and r_bottom would be equal to the adjusted ds_bottom. A p-p would be considered "in range" if it is between r_bottom and r_top.

The above-described methodology can accomplish three objectives. First, it allows the range to dynamically increase and decrease. Secondly, the range can expand faster than it contracts. Third, the bottom of the range can expand faster than the top of the range. There are a number of ways to implement these methods and any implementation that accomplishes any of these three objectives is intended to be within the scope of the present invention.

Yet another alternative includes converting the computed pp range to a range of pulse rate values (prv) and comparing each newly detected prv (60,000/pp) to the pulse rate range. "In range" could be determined by whether or not the new prv was less than the maximum prv (max_prv) and greater than the minimum prv (min_prv). Or, "in range" could refer to whether or not the new prv was sufficiently close to the range of prv values. For example, the range top and range bottom could be expanded by a determined number of beats (i.e. max_prv=max_prv+9 and min_prv=min_prv−9). Thus, any new prv that is within 9 bpm of the data set range could be considered 'in range'.

As with pp ranges, prv range calculations can also be dynamic. That is, as new prv's arrive, the range could be recalculated if the new prv is considered to be reliable (e.g., IBI is not too large).

Another method for increasing error detection capabilities is to use two threshold values for determining how close a new IBI is from the previous IBI. For example, if the new IBI is less than the low threshold, it can be considered a "small jump". If the new IBI is between the two thresholds, it can be considered a "significant jump". And if the new IBI is higher then the second threshold, it can be considered a "large jump". Thus, as new values come in, they could be assessed as to whether the new value is "in range" or "out of range", and whether the new IBI is a small jump, significant jump, or large jump. Decisions on whether to display the value, use the value for updating the range, and/or whether to correct the value may be based upon such assessments.

Any heart rate related interval may be used for determining the significance of IBI levels. For example, the inter-beat interval difference of two prv's (the prv IBI) could be used when assessing the proximity of the new pulse value to the previous pulse values. Thus, IBI's can be computed and assessed for pp intervals, prv values, rr intervals, hr values and the like.

Still another alternative includes using the direction of the IBI change to determine whether the jump is small, significant, or large. When a person is physically still, pulse rates can rise or fall at different rates. Thus, different thresholds could be used depending on the direction of the change. For example, a prv IBI that's greater than the previous prv IBI could be considered to be a small jump up if it is less than 8 bpm, a significant jump up if it is between 8-15 bpm, and a large jump up if it is greater than 15 bpm. And a prv IBI that's smaller than the previous prv IBI could be considered a small jump if it is less than 8 bpm, a significant jump if it is between 8-12 bpm, and a large jump if it is greater than 12 bpm.

Yet another exemplary embodiment includes basing the prv IBI thresholds on the location of the previous prv in the range. If the previous prv is already toward the top of the range, the threshold could be set smaller, since in theory, one would not want the next prv to jump too far outside the range. Likewise, if the previous prv is already toward the bottom of the range, the prv thresholds for jumping down could be decreased. Thus, examples of prv IBI thresholds based on the location of the previous prv in the range could include: ((r_top-prev _prv)(⅓))+10 for a small jump up, ((r_top-prev_pr)(⅔))+15 for a large jump up, ((prev_prv-r_bottom)(½))+10 for a small jump down, and ((prev_prv-r_bottom)(⅔))+15 for a large jump down.

Yet another exemplary embodiment is to add a third test such as direction when determining if a new heart rate interval point needs to be corrected. For example, if the point fails the IBI and the range tests, but is closer to the range then the previous heart rate interval point, then it could still be considered acceptable.

In certain circumstances and implementations, a marginal improvement may be obtainable by combining the dynamic range method, the double IBI threshold method with different thresholds based upon direction, and the heart rate interval direction method. An example of such a combination is as follows. As each new prv is calculated (60,000/pp), it can first be assessed whether or not it is 'immediately displayable'. If the prv is a small jump up or small jump down (using appropriate thresholds) it is 'immediately displayable' and therefore is immediately displayed. If it is a significant jump but is 'in range' then it is 'immediately displayable' and therefore is immediately displayed. Otherwise, it could be re-evaluated by direction to see if it is displayable. If the current prv is closer to the range than the previous prv, then it is still displayed. Otherwise, it is not displayed and must be corrected.

Combinations of the above-described methods also may be used to determine when a value was 'reliable' or not. That is, these methods may be used to determine whether a new prv should be used in recalculating the dynamic range. For example, if the new prv is a small jump, it could be considered 'reliable'. If the new prv is a significant jump, but is 'in range' then it could be considered 'reliable'. And if the new prv is a significant jump and 'out of range' but is closer to the range than the previous prv, then it can be considered 'reliable'.

In deciding which methods to employ to detect and correct errors in a data set, one should consider the hardware stability, use environment, and other factors to determine if the degree of potential statistical advantage of complex combinatorial methods offers a greater practical utility over the basic IBI/range methodology. In most situations the basic IBI/range strategy is quite sufficient. If, however, significant movement, sunlight, pressure and similar factors are expected to be present, the additional statistical methodology described above may be implemented to provide even greater accuracy in detection and correction of errors in a data set.

Resolution of Scaling Problems and Identification of Rhythmic Breathing

Methods and devices described above also may use RSA wave information to innovatively scale the area of the display where the waves are shown.

The amplitude of RSA waves can vary significantly from person to person. As described earlier, RSA amplitude depends on the individual'age, sex, fitness level, breathing pattern, and more. While large display screens can accommodate large waves or small waves, small display screens on portable devices require sophisticated scaling. Thus, if the scale on a small display is too small, then large waves will not fit on the display. If the scale is too large, then the shape and size of small waves will become indiscernible. And if the scale is too dynamic and adjusts too frequently, then large waves and small waves will appear to be the same size, and the user will not be able to discern whether or when his breathing pattern has changed.

Devices according to the exemplary embodiments of the present invention can solve the scaling issue by adjusting the display scaling differently during two stages. The first stage lasts from the time the device is powered on until the user begins to breathe rhythmically. The second stage lasts from the time the device detects rhythmic breathing until the device is turned off. During stage 1, a very basic scaling technique can be implemented. During stage 2, an innovative approach can be employed so the user can accurately assess when his breathing has become more shallow (less deep).

For example, when the device is first turned on, the scaling is preferably zoomed in to a small, preset value. Then, the device zooms out whenever a pulse rate point is encountered that is greater than highest value or lesser than the lowest value that can be plotted using the current zoom level. The scale is zoomed out such that the new pulse point is plotted at the edge of the device display area. To give the user an idea of scale, the device only zooms out, not in, at the beginning. The display also zooms back in after large waves have exited the screen, so that the full height of the display is used from top to bottom. The display continually zooms in and out such that the data points being shown consume the full range of the display at all times until the user begins rhythmic breathing.

Once the user begins to breathe rhythmically, the device seeks to encourage him to breathe deeply. If the device continued to automatically zoom in when small waves appear, then the small waves produced by shallow breathing will appear the same size as the large waves produced by deep breathing. This will not allow a user to visually discern his depth of breathing from the size of the waves.

Figure 43:
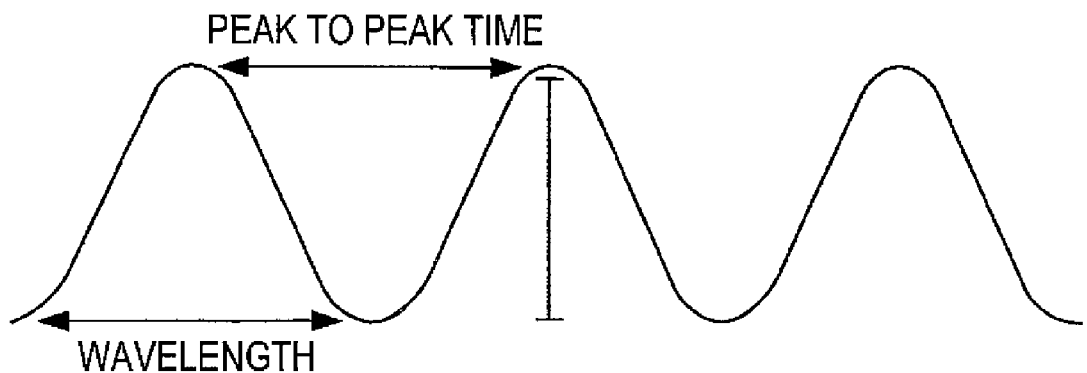
FIG. 43 illustrates representative wave features which may be used to determine when a subject has achieved rhythmic breathing.

Devices according to exemplary embodiments of the present invention use the wave information to detect rhythmic breathing. Rhythmic breaths produce waves with uniform wavelengths, frequencies, amplitudes, peak to peak times, and peak placement times (FIG. 43). By measuring the variance of one or more of these wave feature parameters, rhythmic breathing can be identified. Exemplary embodiments calculate the variation of the wavelengths and amplitudes of the last three waves. When both of these variations are low, then rhythmic breathing is considered to have begun.

One method of determining variance, and thus establishing when a variance is small, can be based on the percent relative deviation. This method is useful when comparing the variation of two or more values (e.g., peak-to-peak times, wavelengths, frequencies, etc.). This may be done as described below. First the mean (average) of the values can be determined. Then the sum of the difference (sum_dif) of each value from the average can be computed. The sum can be divided by the average x number of values. For example, consider four wavelengths: 10, 8, 10, 8 seconds. The average is 9. The sum of the differences from the mean is 4 (10 is 1 away, plus 8 is 1 away, plus 10 is 1 away, plus 8 is 1 away). Thus 4 is divided by the mean x number of values (4/(9×4)). Thus the percent relative mean deviation is 11.1%. Consider four amplitudes: 30, 28, 30, 28 bpm. Although the deviation is also 4 as in the previous example, the percent relative mean deviation is only 3.4%. Thus, percent relative mean deviation automatically scales itself to the range of the values being analyzed.

The variance of any of the wave features can be analyzed alone or in combination using numerous methods. The preferred embodiment employees percent relative mean deviation. The greater the resulting percentage, the greater the variance. A variance threshold could be set to determine if rhythmic breathing has commenced. For example, if three or more waves have a variation in a wave feature less than 20%, one may conclude that rhythmic breathing has commenced. In a preferred embodiment, rhythmic breathing is considered to have commenced when the variation of the wavelength and amplitude of the last three waves is less than 10% each.

Once rhythmic breathing has begun, the can keep track of the largest amplitude (maximum amplitude) formed by the resulting rhythmic waves. The device continues to determine if the user is still breathing rhythmically with, for example, each and every wave. As long as the user continues to breathe rhythmically, the device will continue to look for the largest amplitude (maximum amplitude). If a newly formed rhythmic wave has a higher amplitude than the current maximum amplitude, then the maximum amplitude can be readjusted to be equal to the new amplitude. In general, the display does not zoom in more than the maximum amplitude. That is, the display scale can be set such that a wave with an amplitude equal to the max amplitude would fully consume the screen from top to bottom. The zoom level can be set to not exceed this set point. As a result, the device can zoom out, but it may not zoom in beyond the set point determined by the maximum amplitude. In this way, users will notice when they are breathing shallowly, because they will see the relatively smaller waves (relative to the maximum amplitude) on the screen.

Sometimes an erroneous wave (a wave with corrected errors that is incorrectly reconstructed) can have the largest amplitude. This large amplitude may be erroneously high. Also, a person's largest possible amplitude can degrade with time until their lungs become used to rhythmic breathing. That is, as their lungs become tired, they will not be able to reproduce waves with amplitudes equal to the maximum amplitude. Since the device should not frustrate the user, but rather encourage him to produce the largest waves that he comfortably can, the device can decrease the maximum amplitude value over time if a successive series of waves do not come sufficiently close to the maximum amplitude. In preferred embodiments, if three consecutive rhythmic waves have amplitudes less than 80% of the max amplitude, the maximum amplitude may be readjusted using the following formula: (largest amplitude of the last three waves)×(100/85). Another alternative is to continually decrease the maximum amplitude until the waves are sufficiently close to occupying the display from top to bottom. For example, the maximum amplitude could be decremented by 5% every time a newly formed rhythmic wave has an amplitude less than 80% of the current max amplitude. Another way to use amplitudes would be to take the highest average amplitude. For example, the average amplitude of the last three waves could be calculated every time a new wave is encountered. The highest average amplitude can be used as the minimum set point.

The use of high amplitudes which occur in rhythmic breathing to establish set points is a novel and useful component of the disclosed invention. Any scaling based upon amplitude, range, variance, or deviation is intended to be within the scope of this invention. For example, the standard deviation of the data set, or subset of the data, could be determined. The maximum zoom level could be set such that values with a certain probability relative to the deviation consume the screen. For example, all values that have an 80% probability of being within the standard deviation would fill the screen from top to bottom.

Additional Exemplary System and Software Processes

Figure 44:
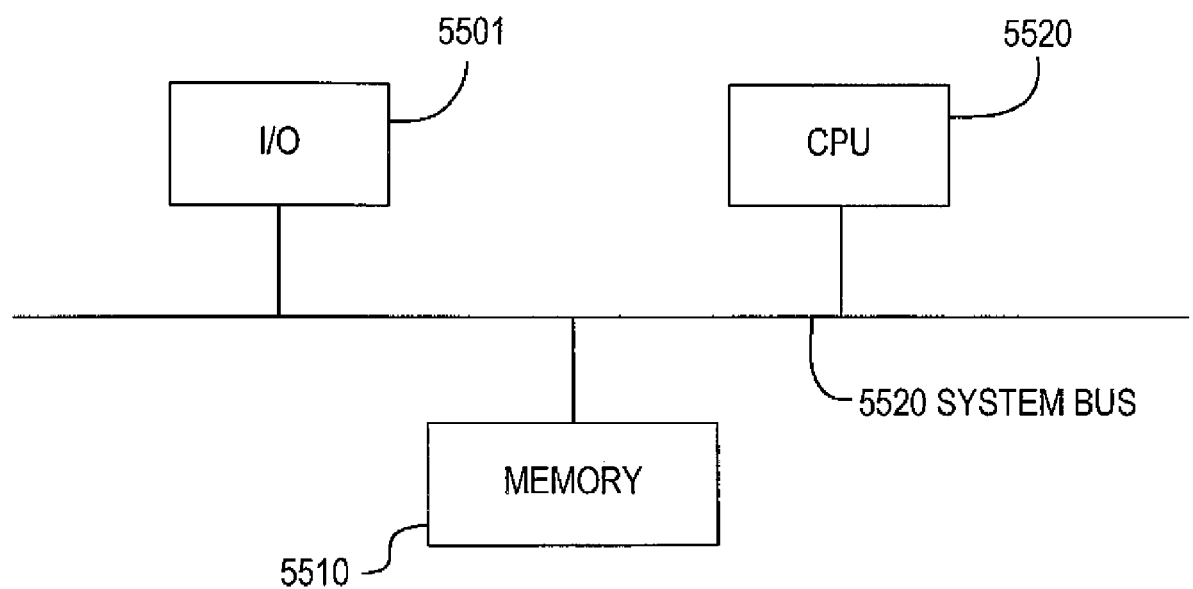
FIG. 44 depicts an exemplary system in which a software process can be implemented according to an exemplary embodiment of the present invention.

Methods and devices described above may be implemented, for example, as a process stored in a memory of a data processing device, such as, for example, a computer. Such a process, can, for example, be in the form of software, and can, for example, be executed by a data processor or CPU and the results displayed on a display, such as, for example, a CRT, plasma or other computer display as is known in the art. Thus, for example, such software can be implemented on a system comprising a CPU, a memory, and a display, all connected by one or more busses or data pathways. FIG. 44 depicts such an exemplary system.

With reference thereto, there is provided an I/O or input/output interface 5501, a CPU 5505 and a memory 5510. The three components of the exemplary system are communicably connected via a system bus 5520. As noted, system bus 5520 is a logical component, and in any given embodiment, can comprise a plurality of interconnections between system elements. Given such an exemplary system, a software process can be loaded in memory 5510 and executed in CPU 5505. Moreover a user can provide input to the process via the I/O 5501, and output to user by way of visual, auditory, tactile, or other means can be provided to a user also using the I/O. Such I/O can comprise a physical interface device, comprising one or more sensors, or can, for example, comprise one or more of a microphone and one or more speakers, a keyboard, mouse and visual display, and a tactile input and output mechanism.

Additionally, such a software process can, for example, be expressed using any appropriate computer language or combination of languages using known techniques, and can be, for example, implemented as an embedded system or a conventionally stored program of instructions using known techniques. Such a software process can be implemented, for example, on a device which can be used to evaluate stress in humans, as described above.

Such an exemplary software process can have, for example, a top level process that interacts with a user by displaying messages to a user and by, for example, continually looking for and responding to various user actions, such as, for example, a user pressing a breathing guidance button or a pulse emanating from a user's finger. Such an exemplary software process is depicted in FIGS. 45-63, as next described. It is noted that FIGS. 8(a)-(b), described above, integrate with this exemplary software process, and thus the "process_waves" subroutine, described below in connection with FIG. 58, calls the subroutine "get_waves" depicted in FIGS. 8(a)-(b).

Figure 45:
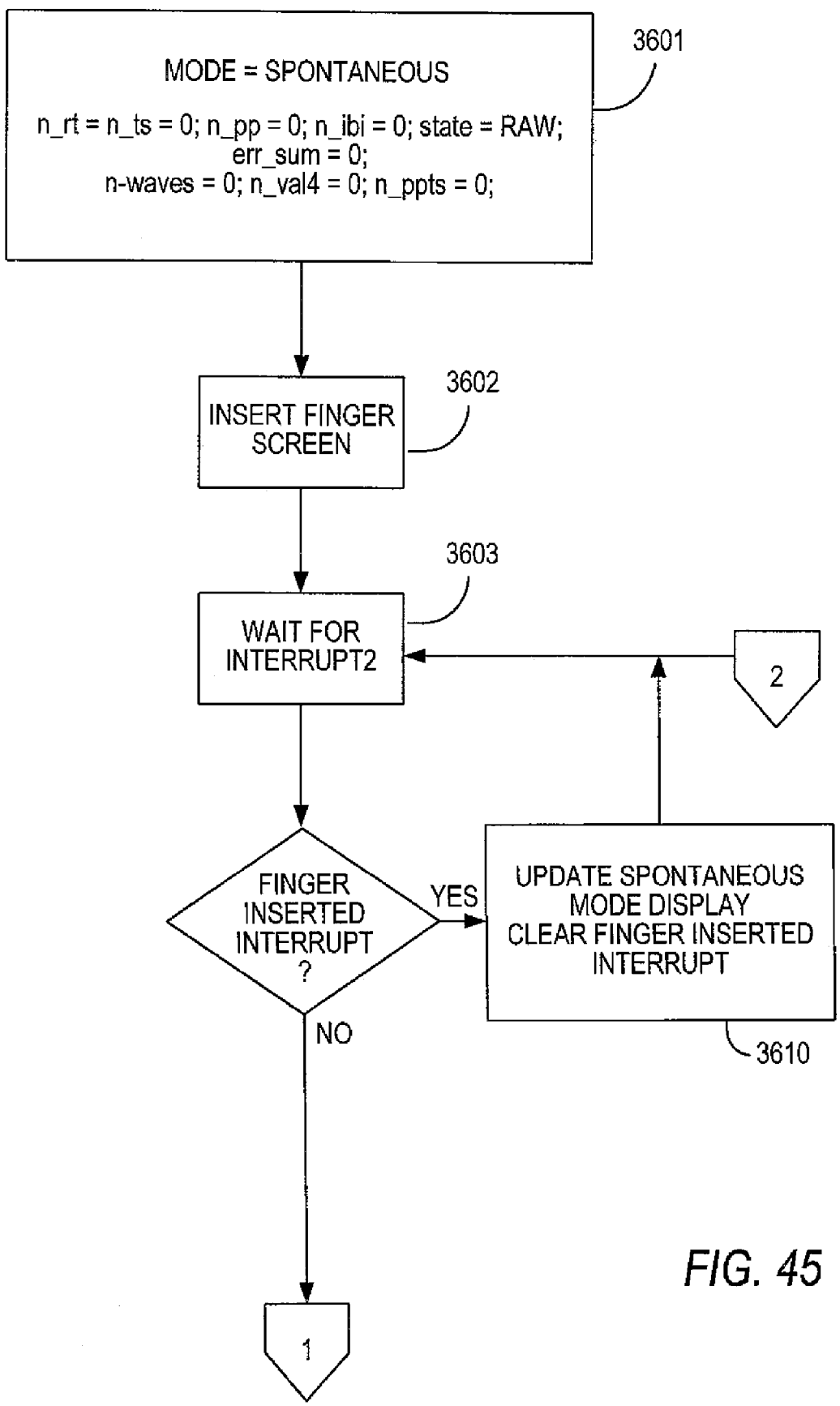
FIGS. 45-46 depict an exemplary process flow for an exemplary top level procedure for interacting with a user according to an exemplary embodiment of the present invention.
Figure 46:
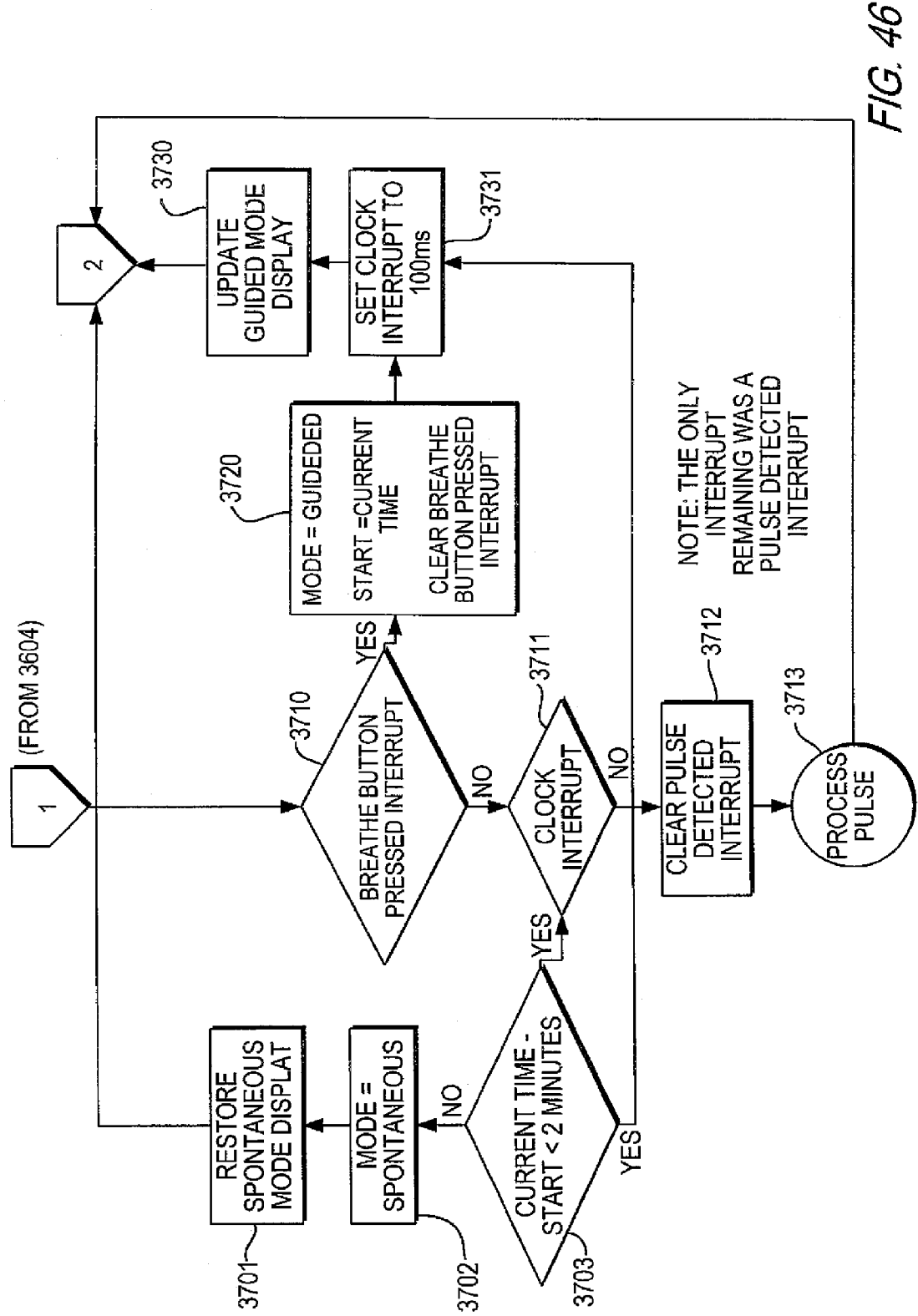

FIGS. 45-46 depict an exemplary top level process, which can control what is displayed to a user and can, for example, respond to user actions. This top level process essentially initializes variables and then waits for interrupts to which it responds. With reference to FIG. 45, at 3601 variables can be initialized. This initialization can include, for example, setting the device mode to "Spontaneous" and setting the values for the following variables to zero: number of raw timesteps, number of timesteps, number of pp intervals, number of interbeat intervals, error_sum, number of waves, number of pp intervals and number of pp interval timesteps, as well as setting the variable state to RAW. This initialization can, for example, be implemented according to the following pseudocode: n_rt=0; n_ts=0; n_pp=0; n_ibi=0; state=RAW; err_sum=0; n_waves=0; n_val4=0; n_ppts=0.

Continuing with reference to FIG. 45, at 3602, for example, an "Insert Finger" message can be displayed to a user. At 3603, the process waits for an interrupt, taking no further action until one occurs. At 3604, if a finger is inserted by a user then at 3610, for example, the device begins calibration, the display message is updated and the interrupt cleared, returning to 3602.

Process flow for this exemplary top level process continues as depicted in FIG. 37. With reference to FIG. 46, at 3710, if a user presses the breathe button, as described above, this can trigger a Breathe Button Pressed Interrupt. Process flow then moves to 3720, for example, where the device mode is set to "Guided", the variable Start set to be the current time and the interrupt cleared. Process flow can then move to 3721, where a clock interrupt can be, for example, set to 100 milliseconds. Process flow can then move to 3730, where the Guided Mode display can be presented to the user. Process flow then returns through breakpoint 2 in FIG. 37 back to 3603 of FIG. 45, where the top level process again waits for another interrupt to occur. This brings process flow back to FIG. 46 through breakpoint 1 where, at 3711, for example, if a clock interrupt occurs, process flow moves to 3703, and tests whether less than two minutes have elapsed from the time the user pressed the Breathe Button at 3710 and entered Guided Mode. If it is still less than two minutes, process flow can move through 3731 to 3730 where the Guided Mode display can be, for example, updated. If at 3703, for example, it has been longer than two minutes since the user pressed the Breathe Button, then process flow can move to 3702, the Mode variable is reset to "Spontaneous", and process flow moves to 3701 where, for example, the Spontaneous Mode display is restored.

Figure 58:
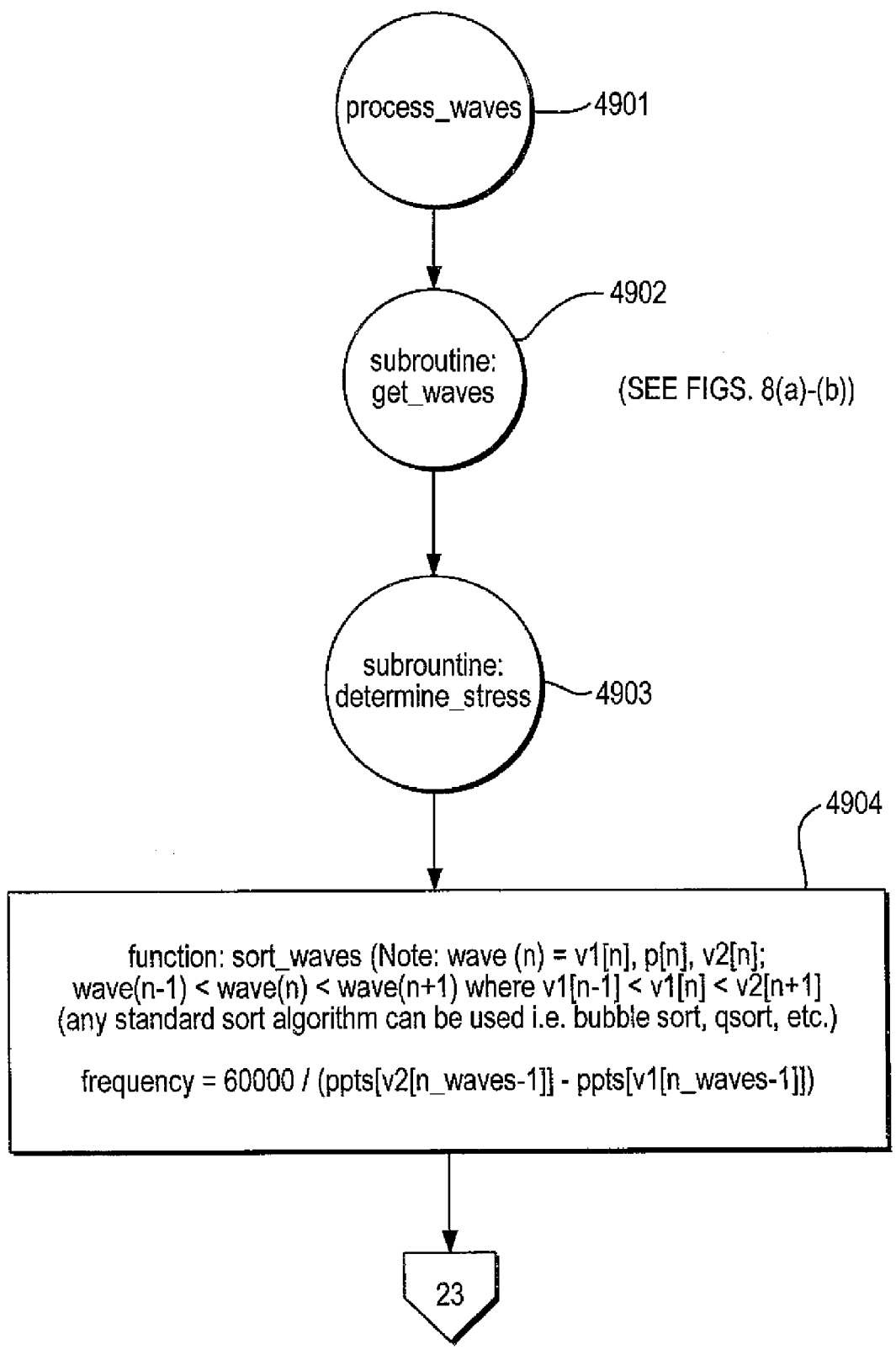
FIGS. 58-59 depict an exemplary process flow for an exemplary procedure for processing RSA waves within a sequence of detected pulses according to an exemplary embodiment of the present invention.
Figure 59:
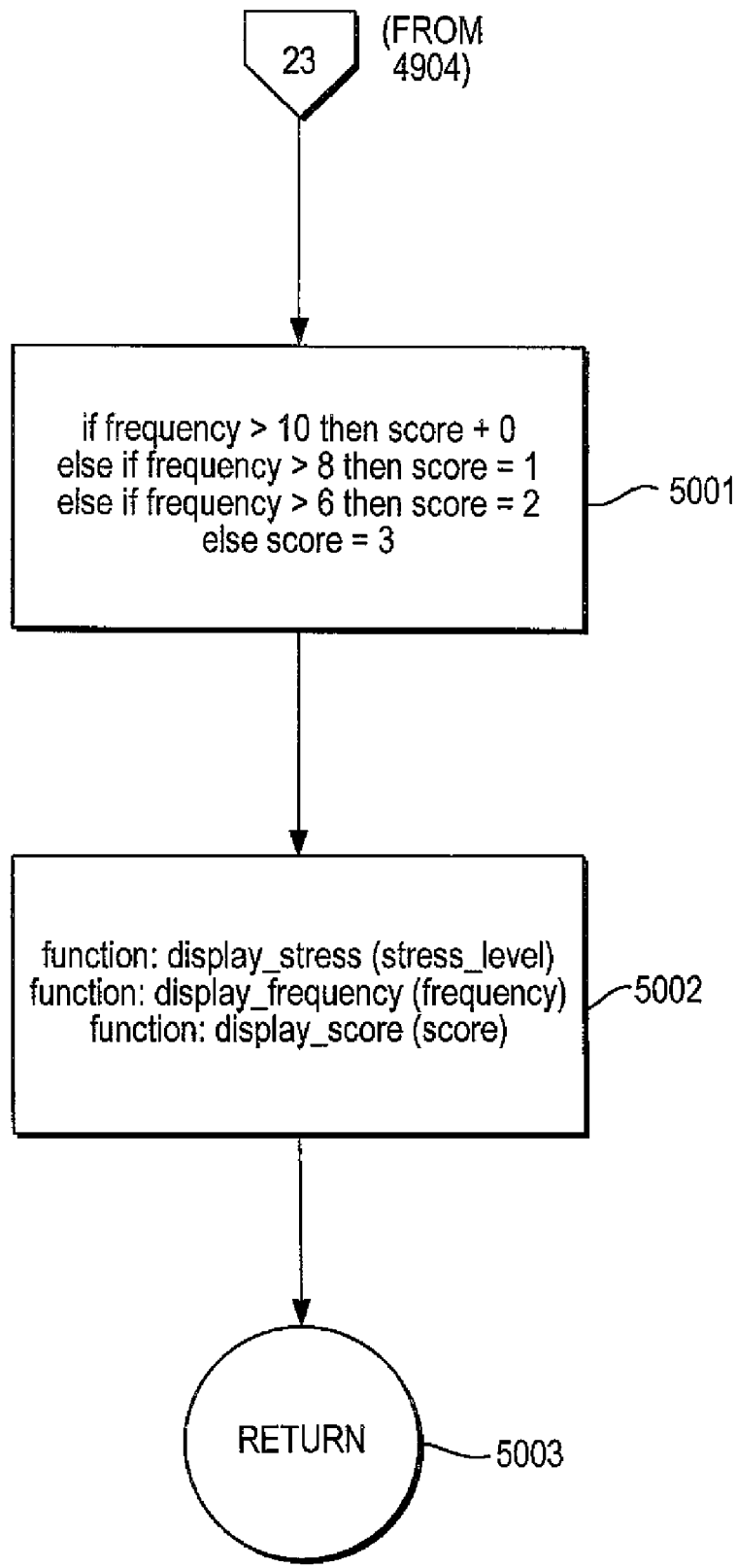
Figure 60:
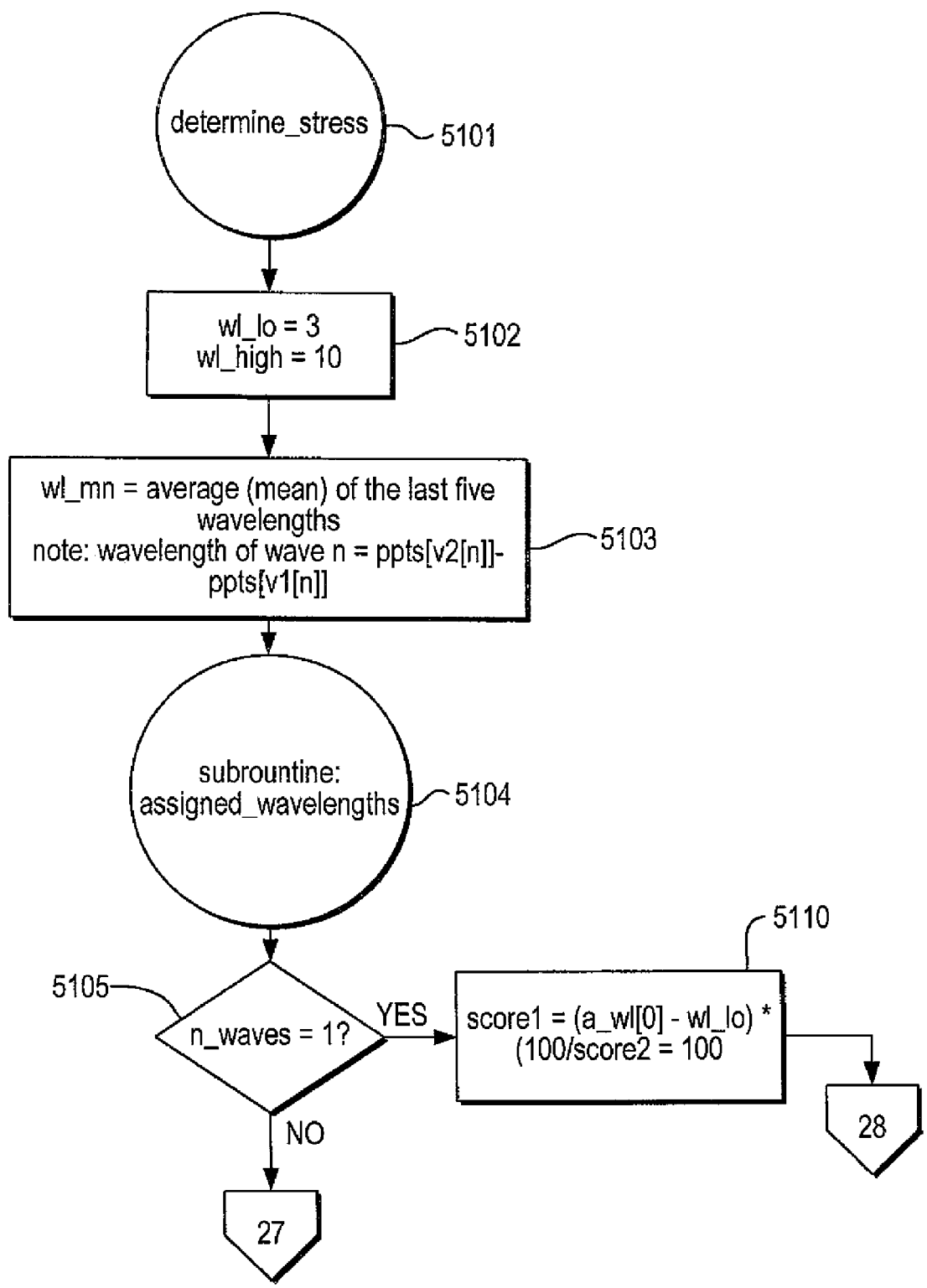
FIGS. 60-62 depict an exemplary process flow for an exemplary procedure for processing RSA wavelengths within a sequence of detected pulses to determine a stress level for a user according to an exemplary embodiment of the present invention.
Figure 61:
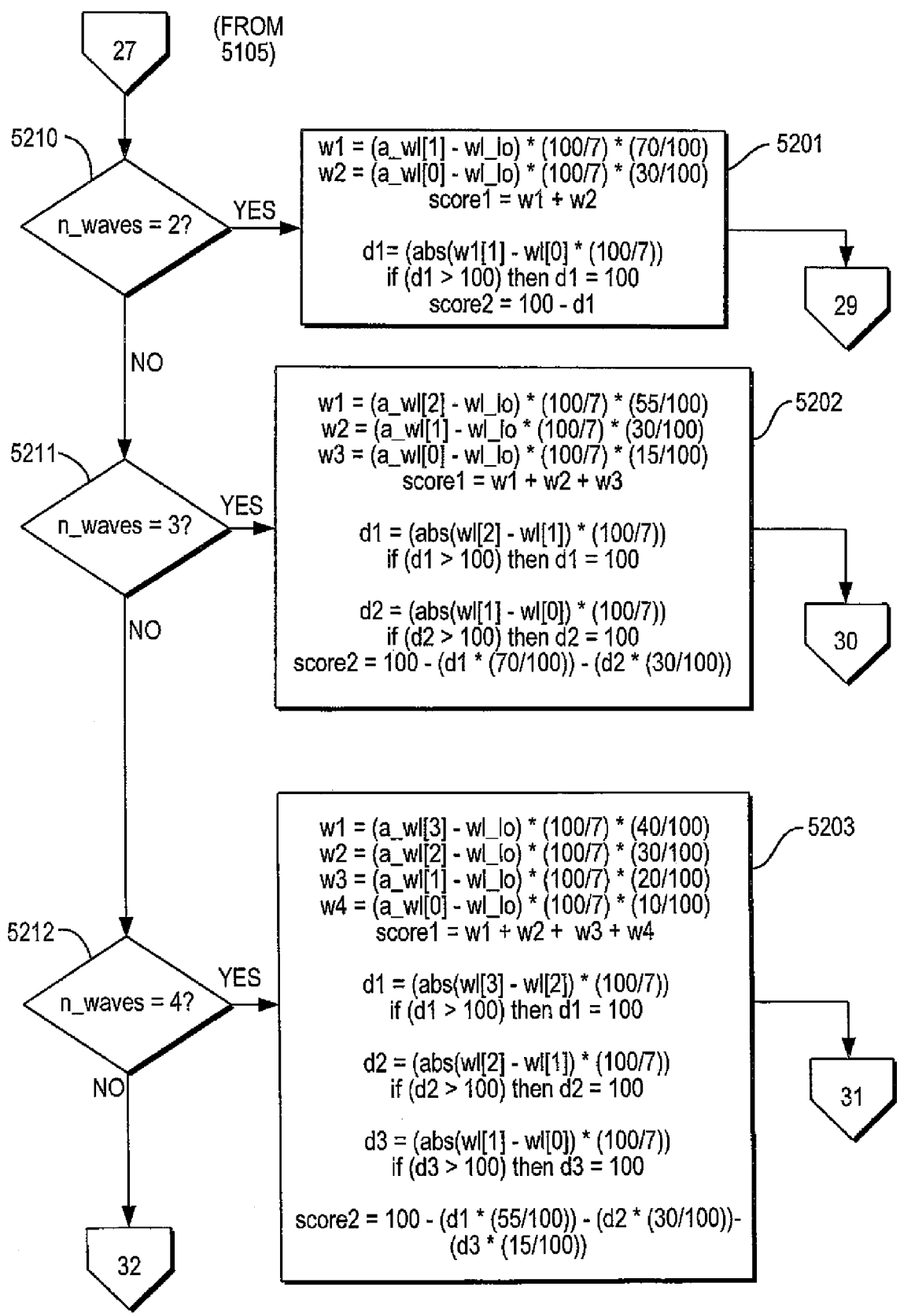
Figure 62:
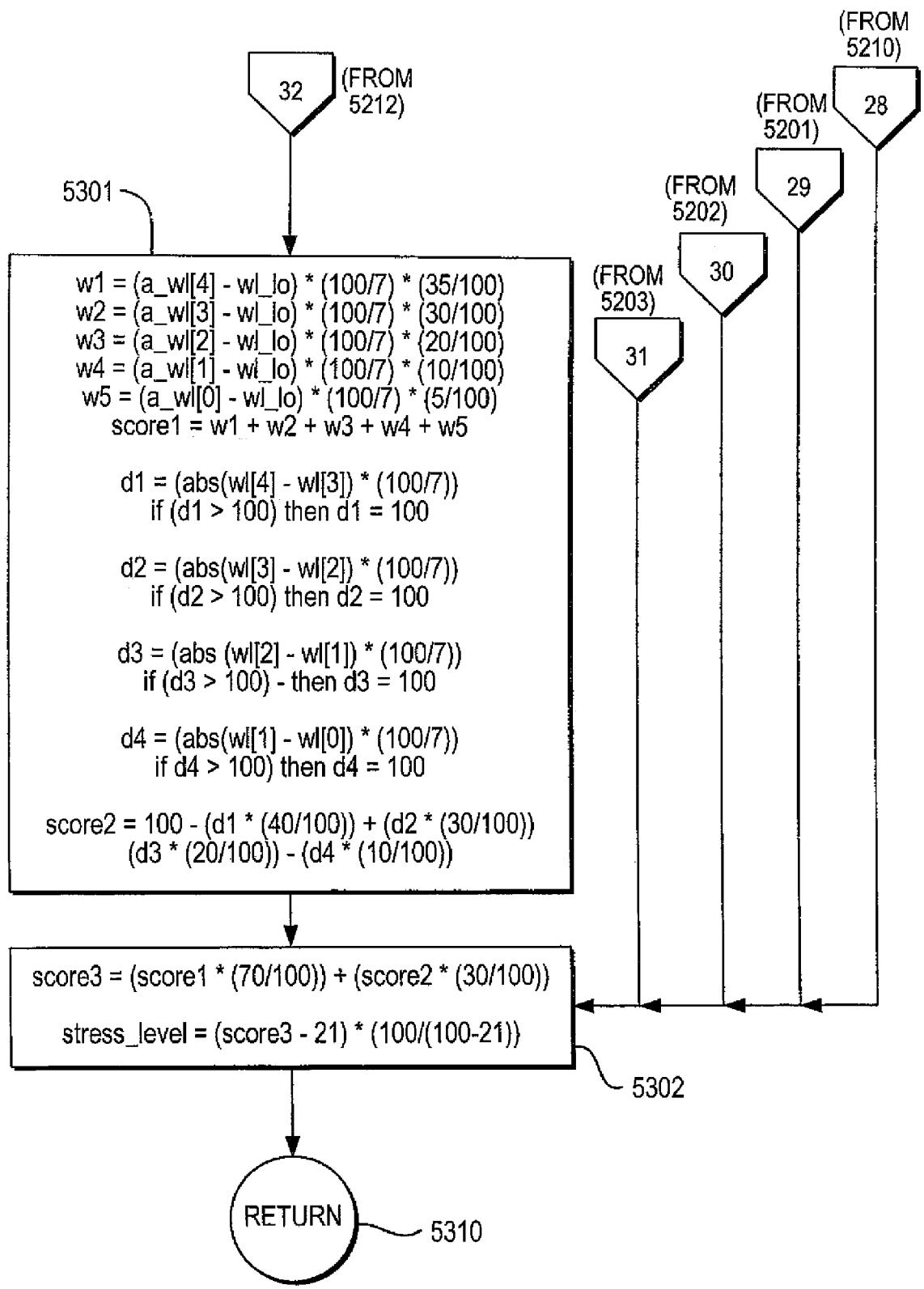

Finally, with respect to FIG. 46, at 3712, if a pulse is detected, a Pulse Detected Interrupt occurs, and process flow moves, for example, to 3713, where the Process Pulse subroutine is called. This ends the exemplary top-level process depicted in FIGS. 45 and 46. FIGS. 47-51 depict process flow of an exemplary main routine according to an exemplary embodiment of the present invention, entitled Process Pulse. Process Pulse calls the subroutines error_correction (FIGS. 52-54), error_detection (FIGS. 55-56), initialize_range (FIG. 57) and process_waves (FIGS. 58-59). In turn, process_waves calls subroutines get_waves (FIGS. 8(a)-(b)) and determine_stress (FIGS. 60-62). Thus all of the subroutines are called, directly or indirectly, by Process Pulse.

Figure 47:
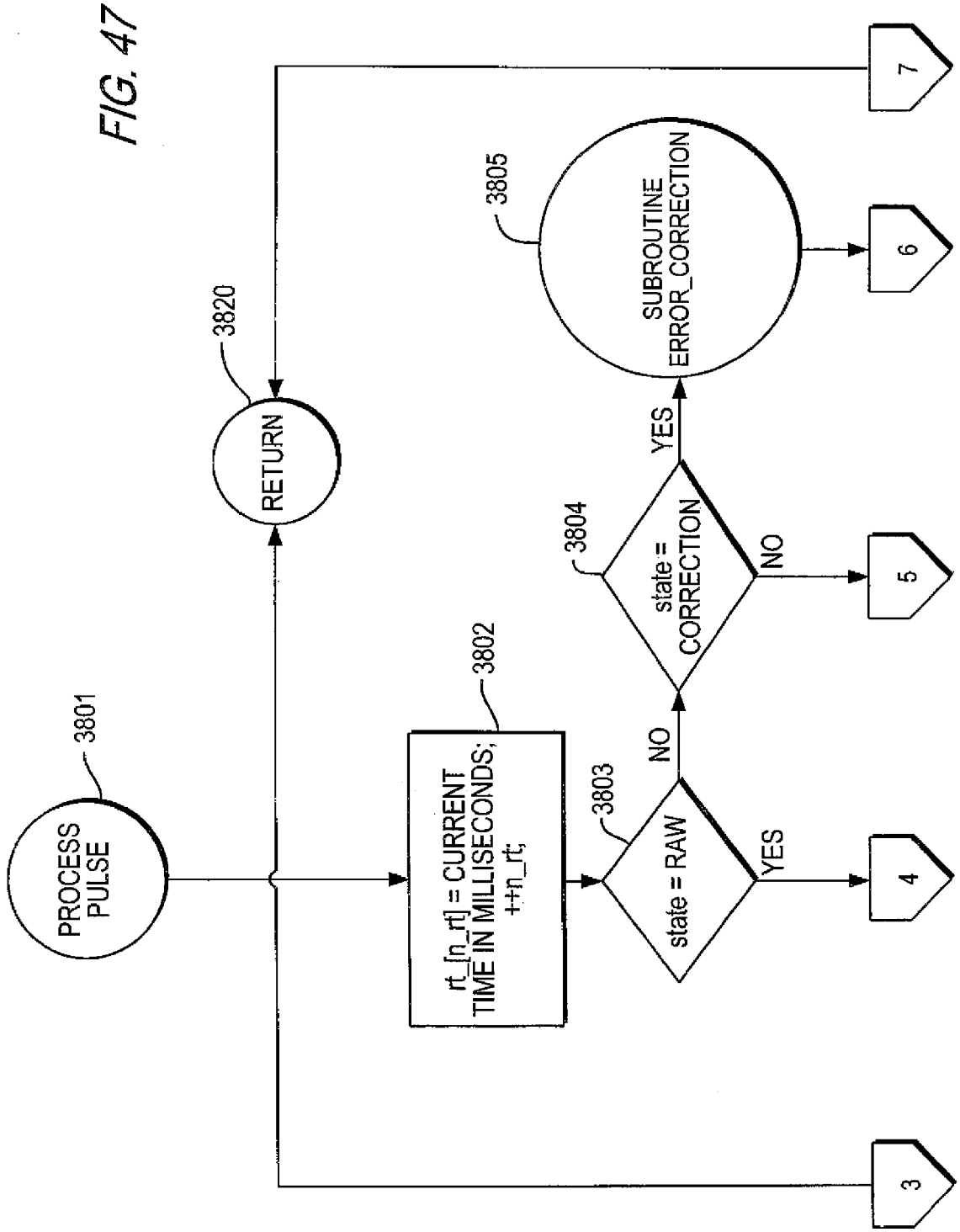
FIGS. 47-51 depict an exemplary process flow for an exemplary procedure for processing a detected pulse according to an exemplary embodiment of the present invention.
Figure 48:
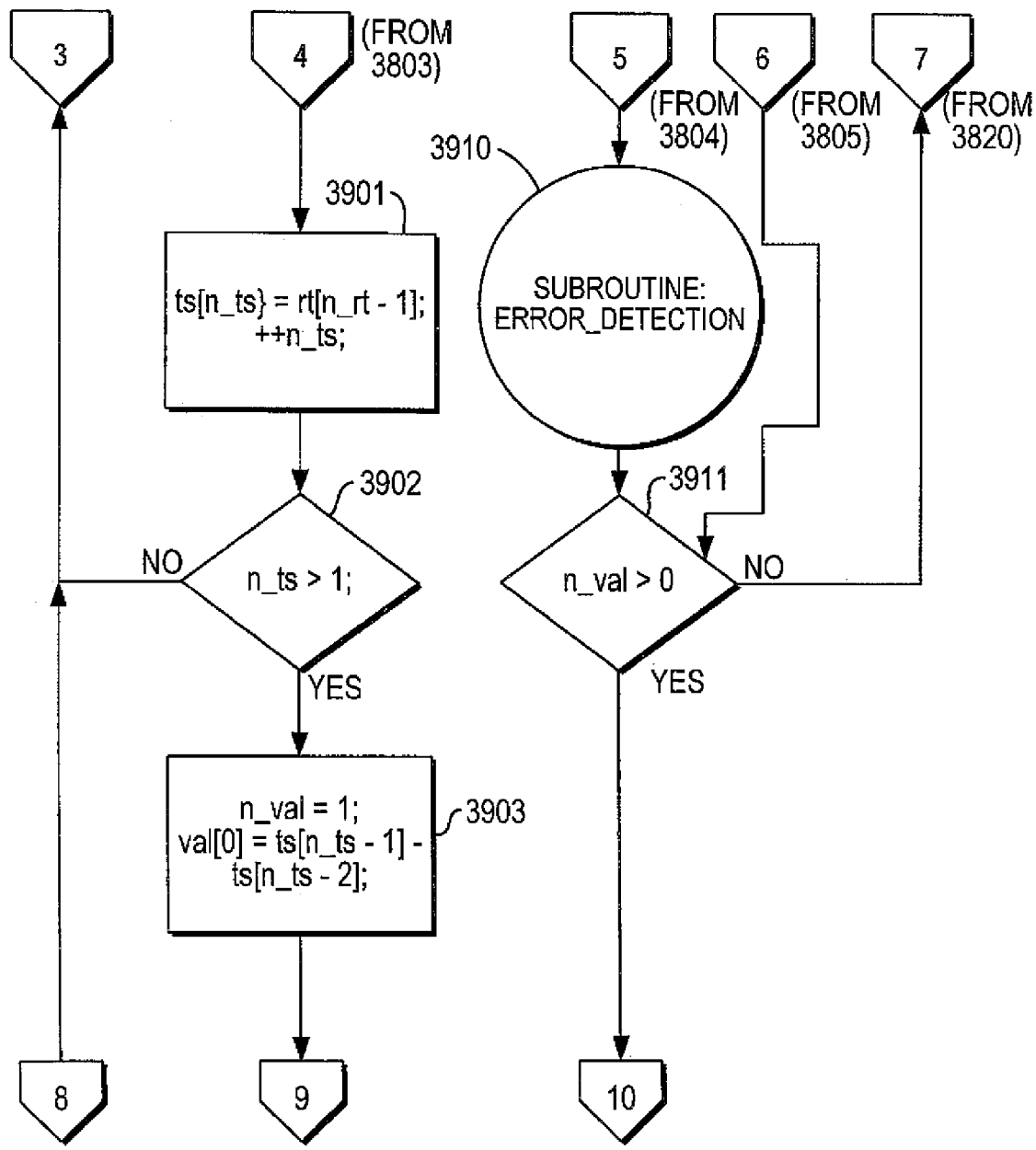
Figure 49:
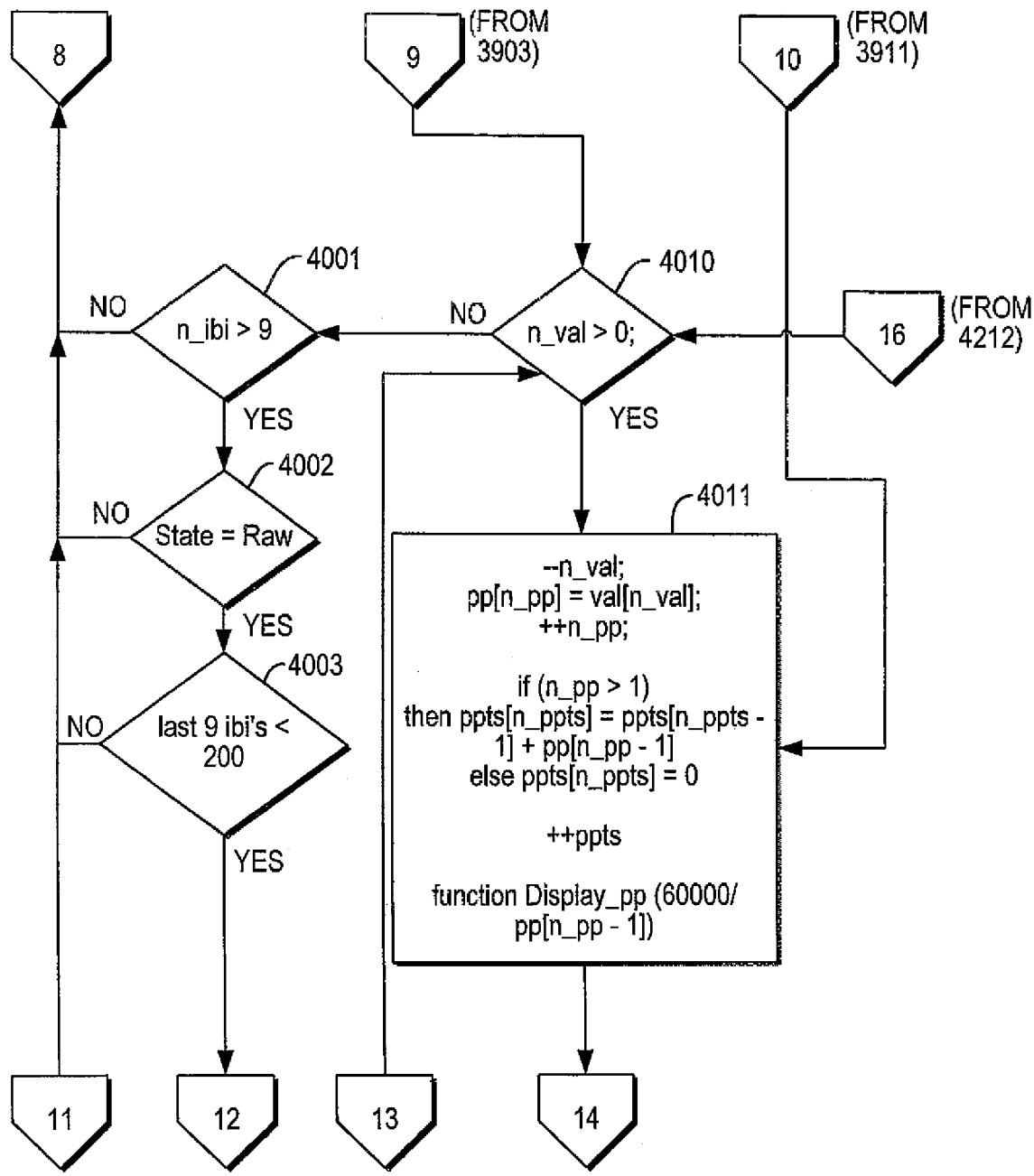
Figure 50:
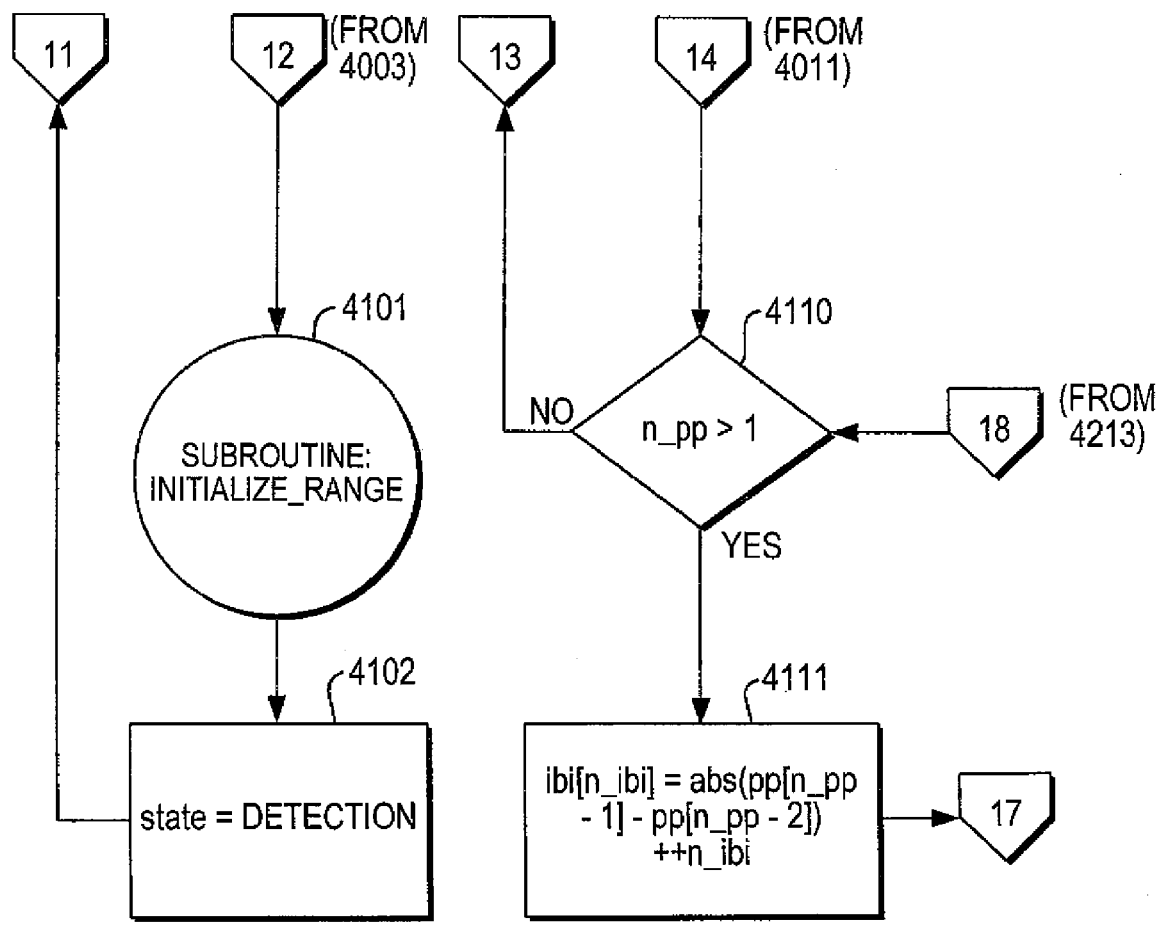
Figure 51:
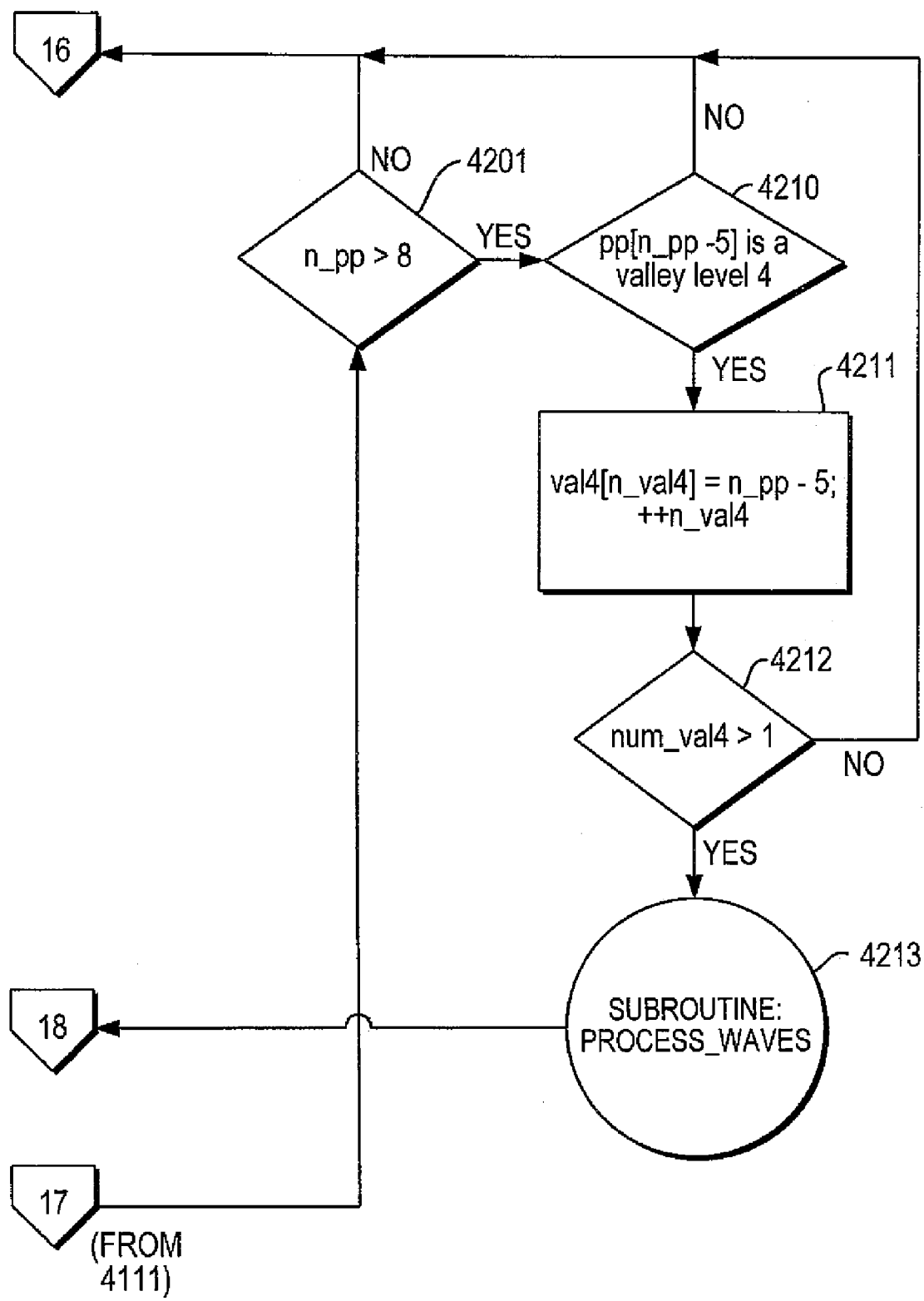

With reference to FIG. 47, at 3802, the raw timestep rt[n_rt], which is rt[0], given the initialization at 3601 of FIG. 45, is set to the current time in milliseconds, and n_rt, or the number of raw timesteps, is pre-incremented. Then, for example, at 3803, 3804 and 3805, the variable state can be tested for being RAW, DETECTION or CORRECTION to determine whether the data is assumed to be error-free, suspect or erroneous, and accordingly along which path process flow will continue. If state =CORRECTION the data path beginning at 3805 will be taken, calling an error_correction subroutine at 3805. If state=DETECTION, the data path beginning at 3804 will be taken, ultimately calling an error-_detection subroutine at 3910 of FIG. 48. These two data pathways ultimately arrive at 4011 of FIG. 49. If state=RAW, process flow can continue directly to 3901 of FIG. 48 where timing variables are initialized, including pre-incrementing n_ts, a variable that tracks the number of timesteps, and through 3902 where n_ts is verified to be greater than one. If that is the case, at 3903, for example, n_val, the number of pp intervals to be assigned, can, for example, be set equal to 1, and process flow can continue, through breakpoint 9, to 4010 of FIG. 49, and through to 4011. When process flow reaches 4011 there are one or more pp values needing to be assigned. Thus, at 4011, each pp value is assigned a value and if there are more than one pp values (i.e., n_val>1) then the actual time steps can be generated, and the instantaneous pulse rate is displayed, which is the frequency of the current pp interval determined by (60000/pp[n_pp-1]). From 4011 process flow continues to 4110, where if there are more than one pp values, calculation of interbeat intervals (IBI's) is possible. This at 4110 the process tests for this condition, and if yes, IBI values can, for example, be calculated at 4111. If not, process flow can loop back to 4010. At 4111, once IBI values are calculated, process flow moves to 4201 to test how many pp values there are. If there are more than 8, i.e., at least 9, then there is sufficient data to identify a level 4 valley. Once there is are at least two level 4 valley points, i.e., num_val4>1 at 4212 the exemplary process can look for RSA waves, as described above. Thus, a yes at 4212 can, for example, cause the process flow to call a process_waves subroutine at 4213.

Figure 52:
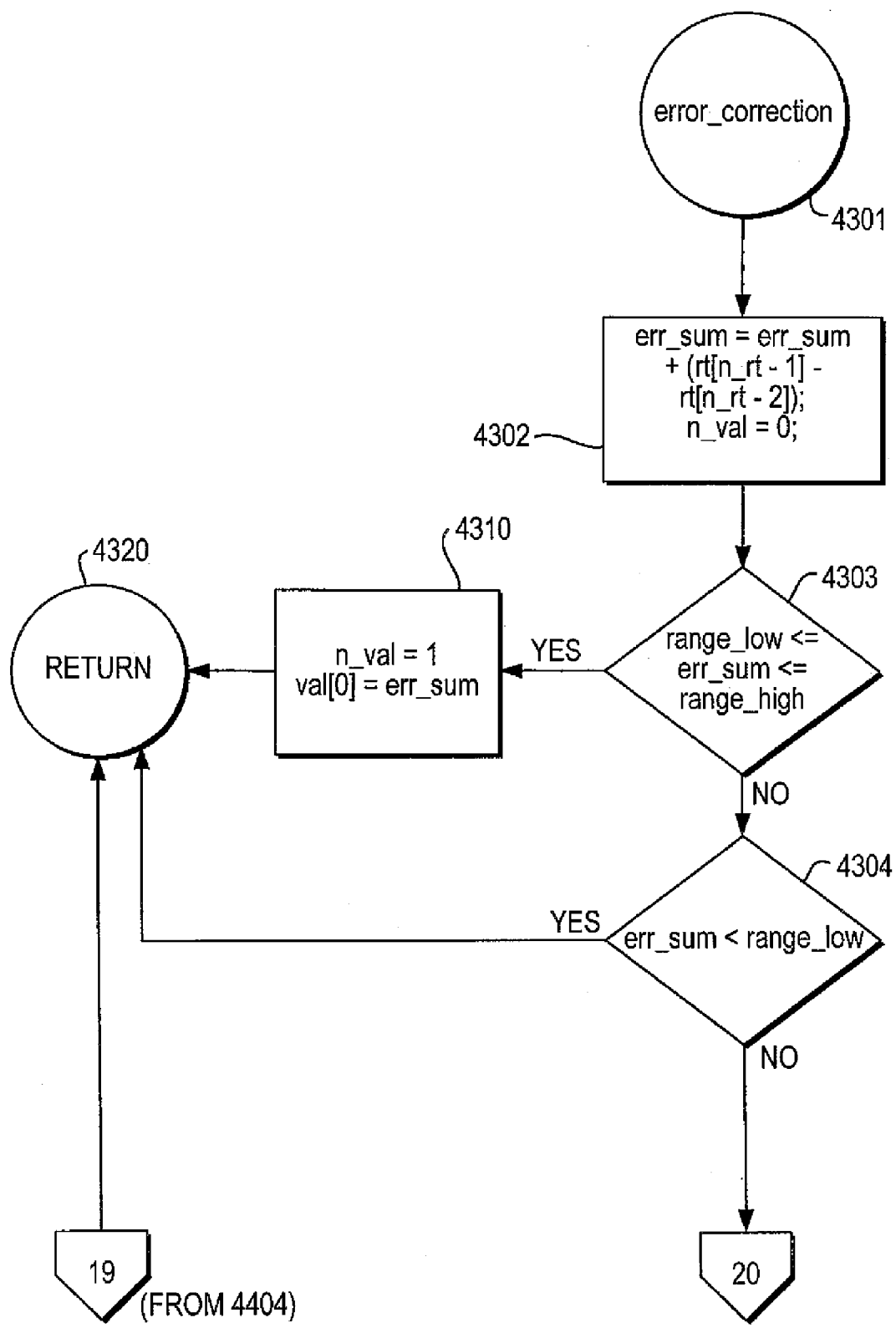
FIGS. 52-54 depict an exemplary process flow for an exemplary procedure for error correction for a sequence of detected pulses according to an exemplary embodiment of the present invention.
Figure 53:
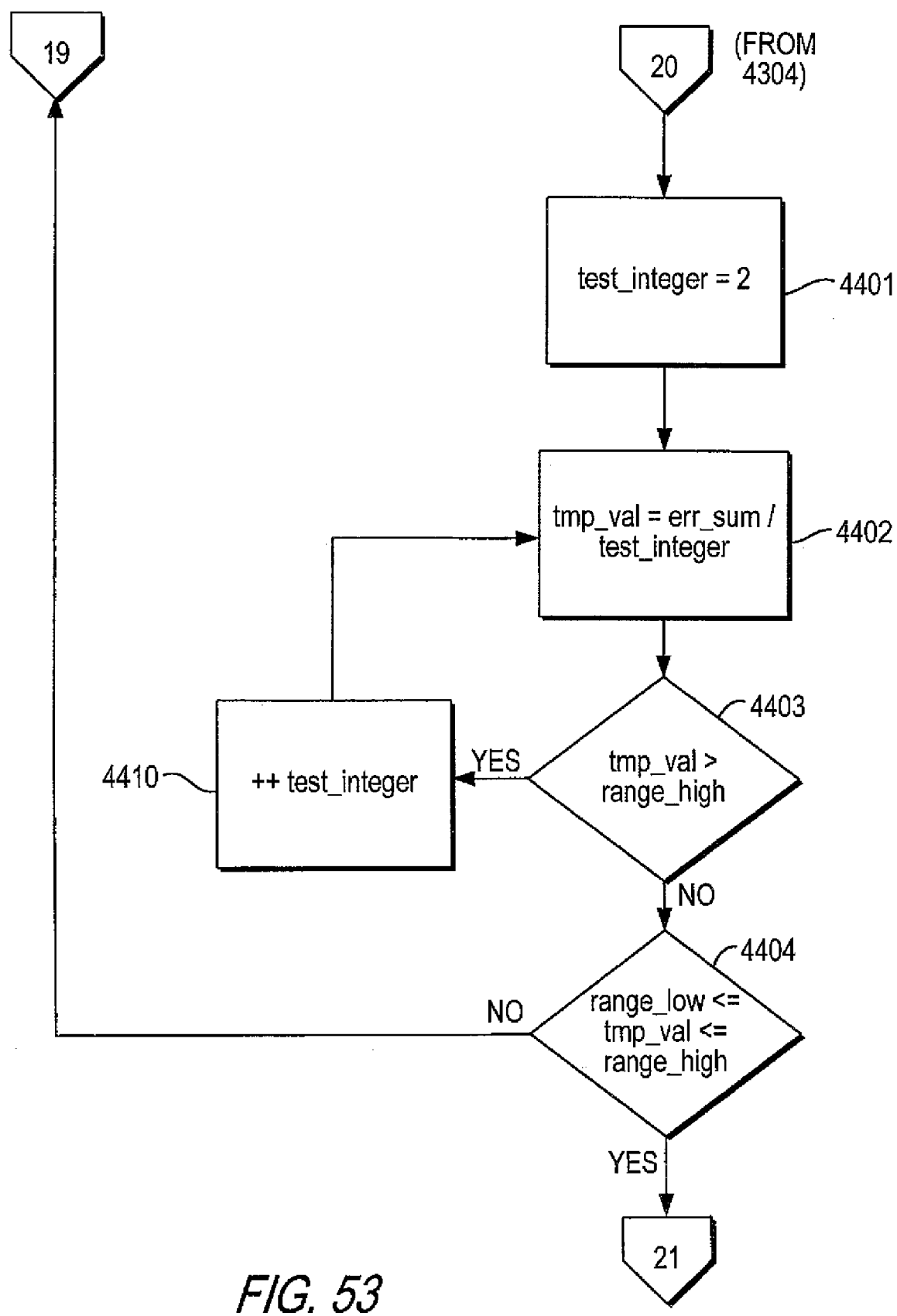
Figure 54:
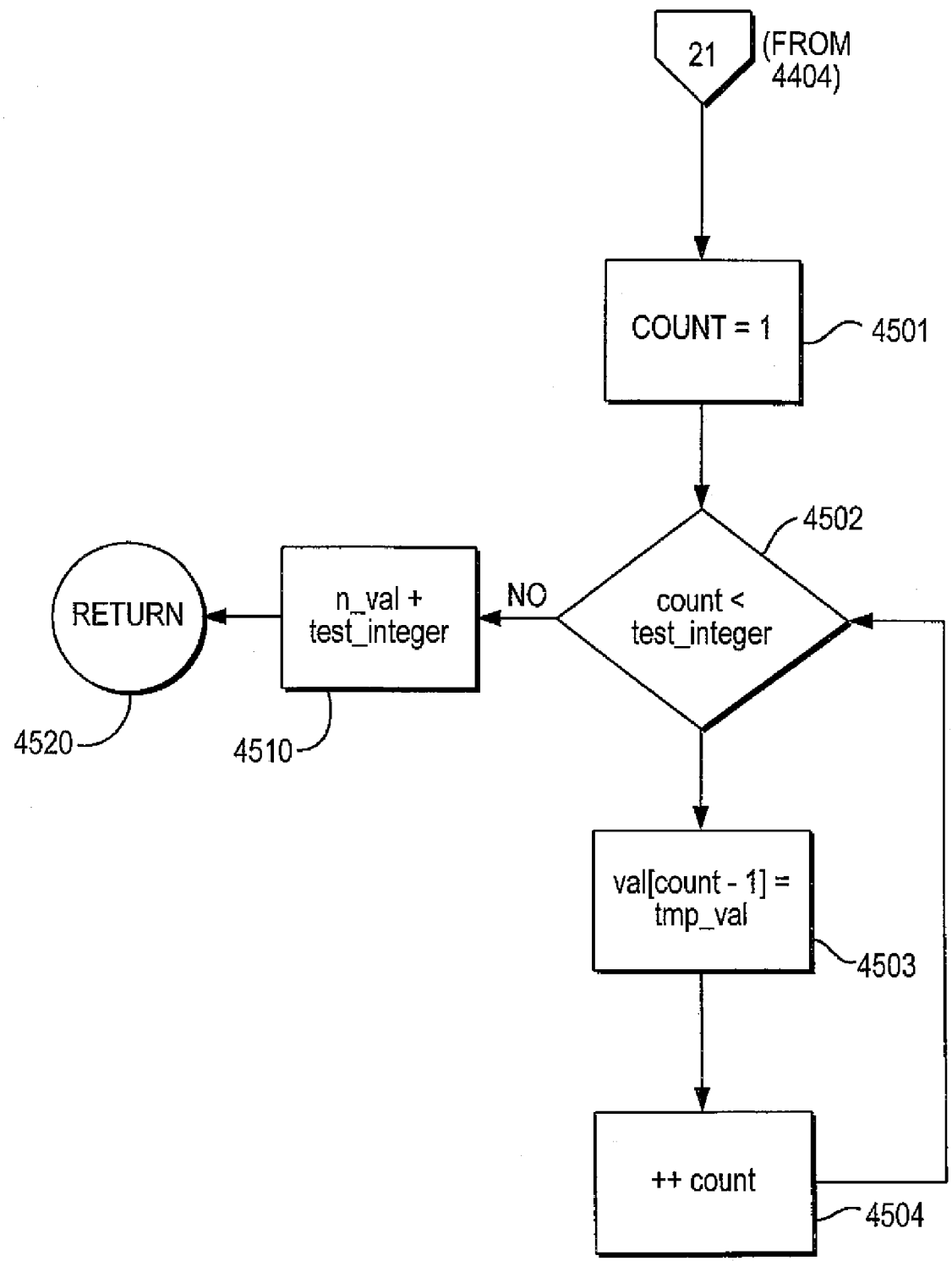

FIGS. 52-54 depict an exemplary process flow for an error correction subroutine. As described above in connection with the exemplary Process Pulse routine, at 3805 of FIG. 38, an error correction subroutine is called. With reference to FIG. 52, process flow begins at 4301, where the subroutine begins. At 4302, for example a variable err_sum, which accumulates current pp interval times, has the most recent pp interval added to it. Additionally, the variable n_val is set to 0. Process flow continues at 4303, where the new value for err_sum is tested as to whether it is in range. If it is in range, process flow can move, for example, to 4310, where the variable n_val is set to 1, representing a correct pp interval being identified, and the value of that pp interval is set equal to the number of milliseconds in err_sum, and process flow returns at 4320 to Process Pulse. On the other hand, if at 4303 the tentative pp interval time is not within range, process flow can move to 4304, where, for example, the subroutine tests whether the current pp interval time is below the range. If yes, process flow returns to 4302 and an additional pp interval time is added to the variable err_sum. If no, then the current sum is considered as too high and a suitable integer must be found with which to divide it to create two or more "in range" pp intervals. Process flow then continues from 4304 through breakpoint 20 to 4401 of FIG. 53.

There, test_integer =2 is set as a test divisor and process flow can move, for example, to 4402 where a temporary variable tmp_val is set up to hold the quotient of err_sum/test_integer, representing a possible actual corrected pp interval. Process flow can then move to 4403, where, for example, tmp_val is tested for being above the range. If yes, then at 4410, for example, the test_integer variable is incremented and the proposed division occurs one more time at 4402. On the other hand, if at 4403 tmp_val is not above the range, than at 4404, for example, tmp_val can again be tested for being within the range, and if yes, process flow can move (through breakpoint 21) to 4501 of FIG. 54.

At 4501 of FIG. 54, a count variable can be set to 1, and at 4502, for example, the subroutine can query whether count is less than the current value of test_integer. If no, then process flow can move, for example, to 4510, and the variable n_val can be set equal to test_integer and at 4520, for example, return to Process Pulse, at breakpoint 6 of FIG. 47. On the other hand, if count is less than test_integer at 4502, then process flow can, for example, loop through 4503, 4504 and 4502, incrementing the value of count each loop (at 4504) until count equals test_integer, at which time process flow can return to Process Pulse. Next described is an exemplary error detection subroutine with reference to FIGS. 55-56.

Figure 55:
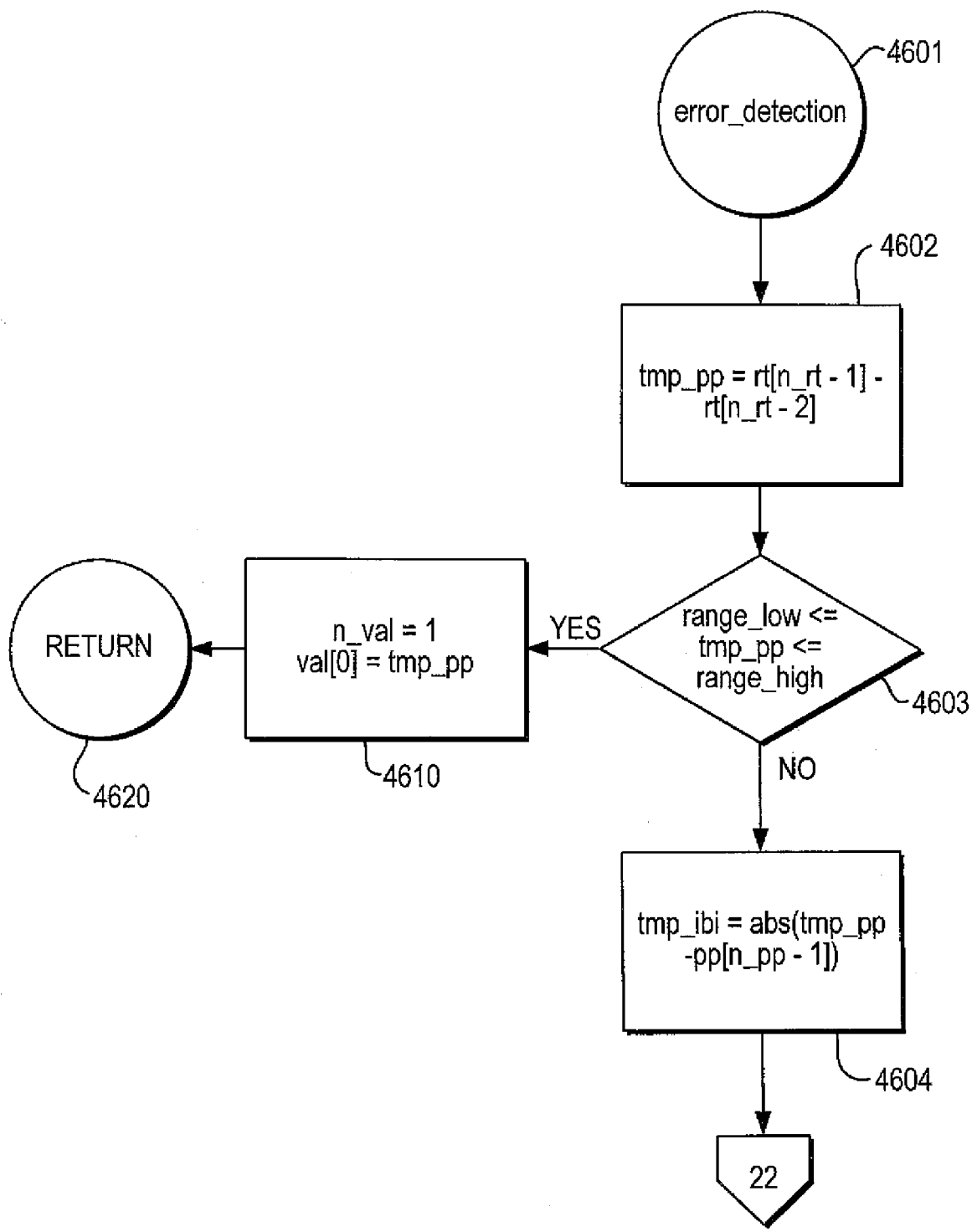
FIGS. 55-56 depict an exemplary process flow for an exemplary procedure for error detection for a sequence of detected pulses according to an exemplary embodiment of the present invention.
Figure 56:
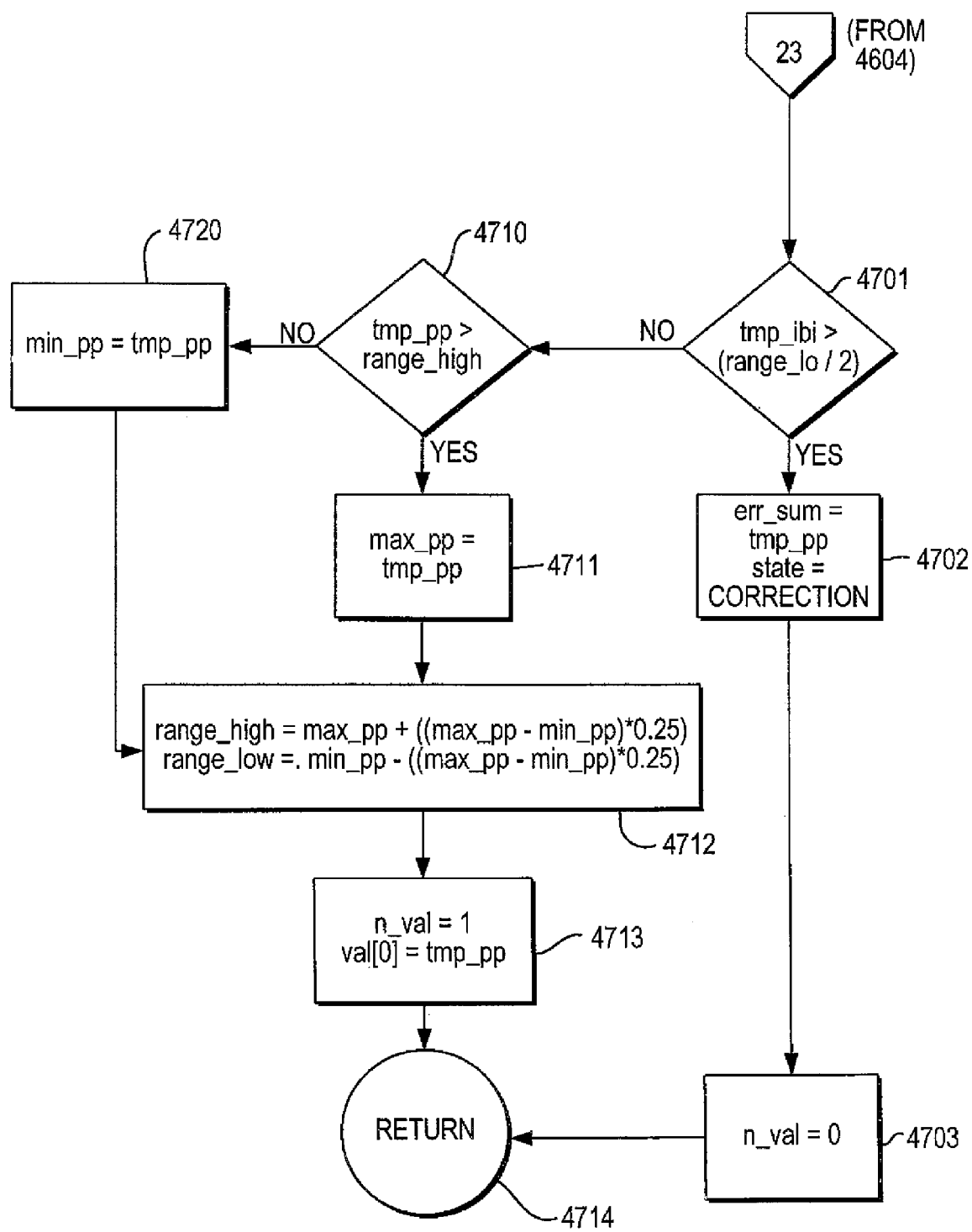

With reference to FIG. 55, process flow begins at 4601 and continues to 4602, where a current pp interval is loaded into temporary (in the sense of tentatively correct) pp interval tmp_pp. At 4603, the tmp_pp is tested for being within range. If yes, then n_val is set to 1 and val[0] is set equal to tmp_pp at 4610 and at 4620 process flow returns to the calling program, Process Pulse, in particular to 3911 in FIG. 48. However, if at 4603 tmp_pp is found to be out of range then, at 4604, temporary interbeat interval variable tmp_ibi is generated to use in detecting any errors as described above. Process flow can then continue (through breakpoint 22) to 4701 of FIG. 56, where tmp_ibi is tested for being greater than half the lower end of the range, which is a test for being too large, as described above. If yes, there is assumed to be an error, and flow continues to 4702, where the variable err_sum is set equal to tmp_pp (err sum is an input to the error correction subroutine described above), "state" is set to be CORRECTION, and process flow can move, for example, to 4703 where n_val is set to 0 and process flow returns to Process Pulse, which can then, based on n_val =0 and state =CORRECTION, return at 3911 of FIG. 48 to 3820 of FIG. 47, and ultimately flow to an error-correction subroutine at 3805.

If at 4701 tmp_ibi is not greater than half of the lower end of the range, in which case it is not considered to be large and thus no error present in the pp interval data, process flow can continue to 4710, and, for example, test whether the tmp_pp is greater than the top of the range. Because tmp_ibi was not found to be large at 4701, and thus no error is assumed present, if at 4710 the tmp_pp interval is still larger than the existing top of the range, the range needs to be recalculated using the new pp interval as max_pp, which holds the value for the maximum possible pp interval which is not the result of an error in the data. At 4711, for example, max_pp can be set equal to tmp_pp and, using this new value, at 4712, for example, the upper and lower ends of the range are recalculated. Flow can then continue, for example, to 4713 where the n_val is set equal to 1 and val[0] is set equal to the current pp interval, tmp_pp. At 4714, for example, process flow can return to the calling routine Process Pulse. If at 4710 the current pp interval is not greater than the existing upper end of the range then, for example, at 4720 the minimum possible pp interval is set equal to the current pp interval. Then process flow continues as described above through 4712, 4713 and 4714, where process flow returns to the calling program.

Figure 57:
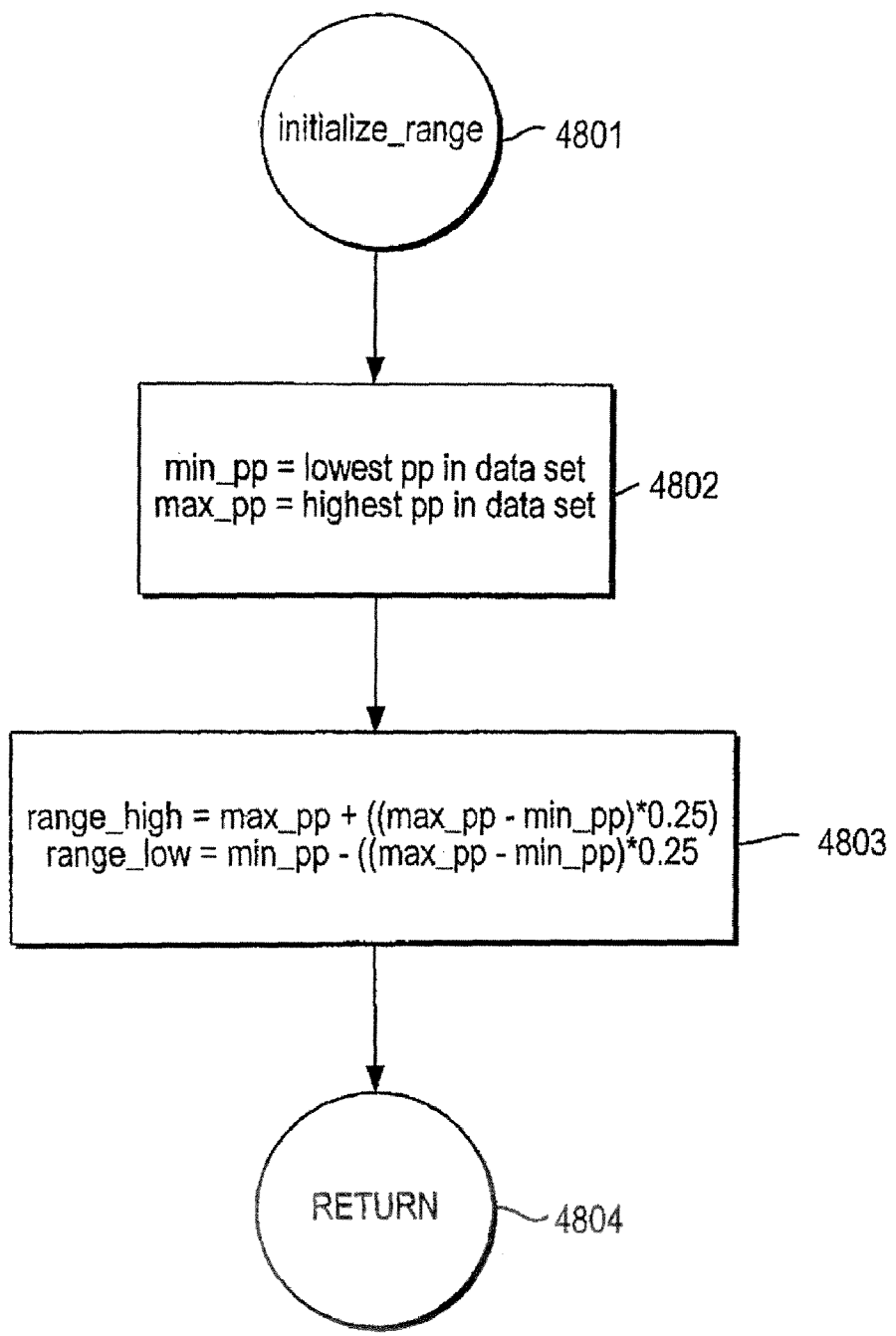
FIG. 57 depicts an exemplary process flow for an exemplary procedure for initializing a range for detected pulses according to an exemplary embodiment of the present invention.

With reference to FIG. 57, process flow for the subroutine initialize_range is next described. This subroutine can be used in exemplary embodiments of the present invention to calculate the range for pp intervals within which the data is assumed to be error free, for use in the error detection and correction routines. Beginning at 4801 at the subroutine call, process flow moves, for example, to 4802, where the variables min_pp and max_pp are set using the following pseudocode:

min_pp=lowest pp in data set; max_pp=highest pp in data set. Then, for example, at 4803, the upper and lower ends of the range of data points used for error detection and correction, as described above. This can, for example, be implemented using the following pseudocode: range_high=max_pp+ ((max_pp−min_pp)*0.25; range_low=min_pp −((max_pp−min_pp)*0.25). Using these exemplary values, the range is now set, and at 4804 process flow returns to the calling routine, i.e., Process Pulse. In particular, process flow returns to 4102 in FIG. 50.

FIGS. 58-59 depict an exemplary process flow for a wave processing subroutine. In an exemplary embodiment of the present invention, such a subroutine can be called, for example, by a pulse acquisition processing routine such as Process Pulse, as described above. After the subroutine is called at 4901, for example, process flow can continue at 4902, where the get_waves subroutine described above can be called to input the waves identified from the pulse data. Process flow continues, for example, to 4903, where, given the acquired waves, a score indicative of a user's stress level reflected in the identified waves can be assigned using an exemplary determine_stress subroutine. Flow can then continue, for example, to 4904 where the waves are sorted and the instantaneous frequency calculated based on the current pp interval using the expression frequency=60000/(ppts[v2 [n_waves-1]]−ppts[v1[n_waves-1]]), where ppts[v] is the pulse point time stamp at data point v. From there, for example, process flow can continue to 5001 on FIG. 59, where a score between 0-3 can be assigned to a user based upon the frequency of the current wave, where a higher score indicates a lower stress level. At 5002, for example, the subroutine can, for example, display to the user each of his or her (i) stress level (obtained from the call to determine_stress at 4903); (ii) frequency (from 4904); and (iii) score (from 5001), at which point, for example, at 5003, process flow can return to the calling routine, Process Pulse.

FIGS. 60-62 depict an exemplary subroutine for determining a stress score. What is being measured is how unrelaxed a given user is, by operating on the wavelengths of his or her RSA waves. With reference to FIG. 60, at 5104 the determine_stress subroutine calls assigned_wavelengths, which assigns a wavelength between wl_lo and wl_high (which are set at 5102) to each wave. Using these wavelengths and how many waves there are (i.e., the value of n_waves), FIGS. 60-61 depicts process flow for each value of n_waves between 1 and 4. A score1 is determined at each of 5110, 5201, 5202 and 5203, which is a weighted sum of the differences between each wave's wavelength and w_lo, which measures how far off the baseline that particular wave is. Thus, a perfect relaxation score would have a_w{n}=w_lo for all n, and each score1 would equal zero. In alternate exemplary embodiments of the present invention score1 can be calculated without weighting the sums of differences, and this is the method as described above. Score1 is what was described as the "wavelength" score. As can be seen at each of 5110, 5201, 5202 and 5203, a "variance" score, score2 is also computed. Score1 and score2 can be combined at 5302 using a 70/30 relative contribution factor to obtain score3. Other relative weightings can be used in alternate exemplary embodiments according to the present invention as may be found useful. Score3 can be used to calculate stress_level using, for example, the equation stress_level=(score3−21)* (100/(100−21)). Stress_level is returned to process_waves at 4903.

Figure 63:
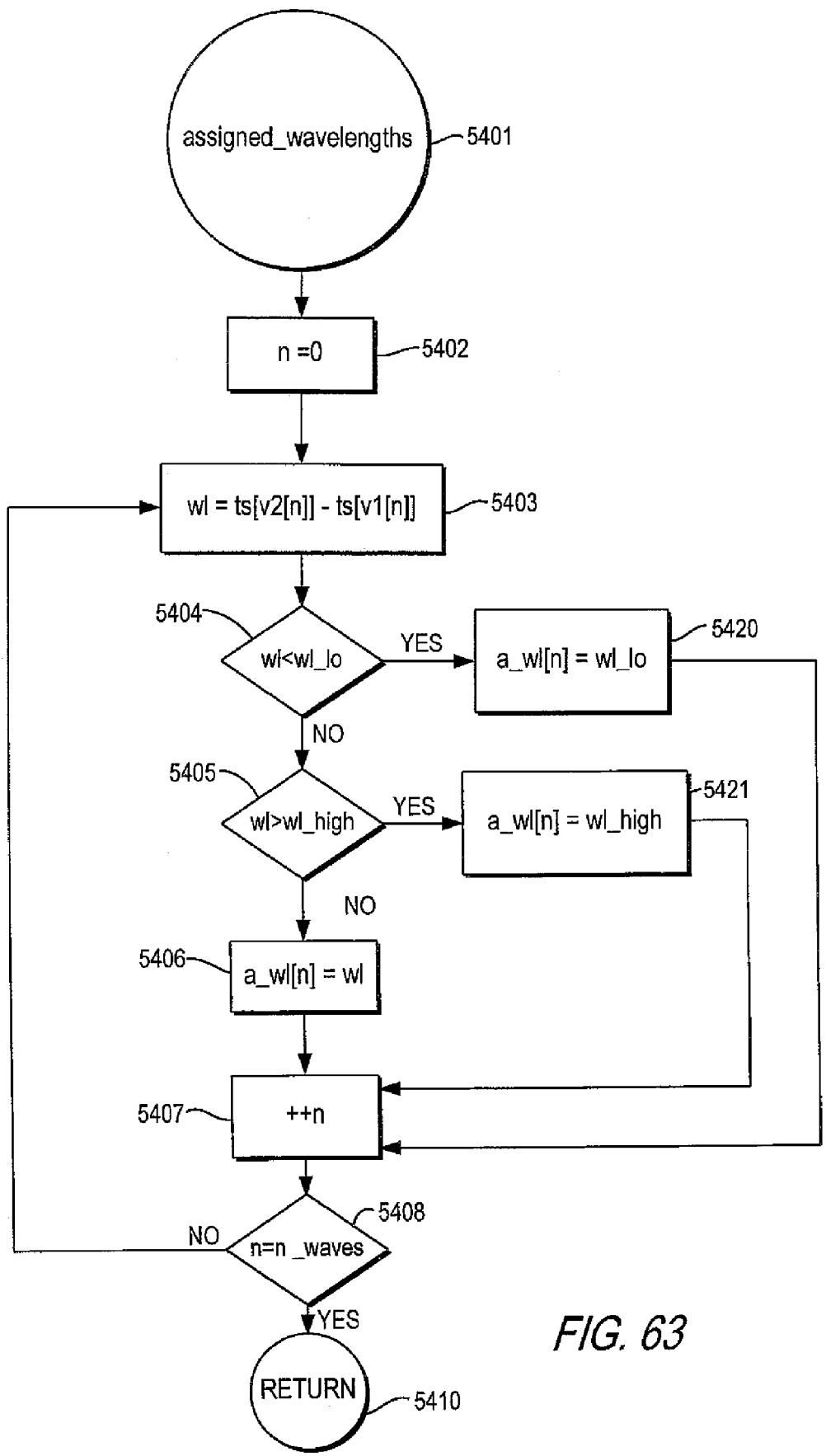
FIG. 63 depicts an exemplary process flow for an exemplary procedure for assigning wavelengths to RSA waves according to an exemplary embodiment of the present invention.

With reference to FIG. 63, an exemplary subroutine for assigning wavelengths to acquired waves is depicted. This subroutine can be used, for example, in the exemplary determine_stress routine depicted in FIGS. 60-62, as described above, which takes wavelengths as inputs. In an exemplary embodiment of the present invention, process flow can begin at 5401 with a call to the subroutine. At 5402 a counter variable n is set equal to zero, and at 5403, for example, a current wavelength wl is calculated by subtracting the timestamp of the current v2 from that of the current v1, using the expression wl=ts[v2[n]]−ts[v1[n]]. At 5404 and 5405, for example, the value of wl is compared with that of wl_lo and wl_high, which can be set in the calling subroutine as seen at 5102 of FIG. 60 (where, for example, they are set as 3 and 10, respectively). If wl is less than wl_lo or higher than wl_high, a_wl[n] is truncated at either wl_lo or wl_high, as the case may be, and flow continues at 5407 where the value of n is pre-incremented. If, however, wl has a value between wl_low and wl_high, then, for example, at 5406, a_wl[n] is set to wl, and process flow continues to 5407. At 5408 the value of n is compared with that of n_waves, to insure that each acquired wave has been assigned a wavelength. If they are equal, at 5410, for example, process flow ends for this subroutine, and returns to 5105 n FIG. 60. If they are not equal, then flow loops through 5403 for each acquired wave until all acquired waves have been assigned wavelengths.

Exemplary embodiments of the present invention also provide, for example, methods and devices which can determine the phase of RSA waves in real-time, using the phase changes to detect the drop point, using the phase changes to detect the completion of a wave, and determining parasympathetic intensity of the newly formed wave.

FIGS. 64 to 74 depict exemplary flow processes for an exemplary procedure for determining the phase of RSA waves on a pulse-by-pulse basis, using the phase changes to detect the drop point, using the phase changes to detect the completion of a wave, and determining parasympathetic intensity of the newly formed wave. This exemplary embodiment describes a single, interrupt driven process that executes each time a new pulse is received.

The exemplary processes and process flows illustrated in FIGS. 64 through 74, as well as any exemplary functions implementing such processes, including any auxilliary functions and/or processes called or utilized by such exemplary flow processes, are presented for illustrative purposes. Those skilled in the art will recognize that each exemplary process or function, whether at a called function or process level, or at an overall level for an entire top level process, can be implemented in a variety of functionally equivalent ways, and the description of FIGS. 64 to 74 which follows is in no way to be construed as limiting the wide variety of possible implementations in actual systems or devices, or requiring that the illustrative exemplary process flow be literally followed.

Bearing this in mind, for economy of expression as well as for elegance of illustration, the process flow in each of FIGS. 64 to 74 will next be described without continual reference to the exemplary nature of each stage or step in process flow, it being understood that in exemplary embodiments of the present invention functionally equivalent implementations can, for example, use different processes, as well as different sequences of processes and organizations of process flow, from that which is illustrated in FIGS. 64 through 74, to achieve equivalent functionalities. All of such alternate embodiments and equivalent functional implementations are understood to be within the methods and techniques of the present invention.

Figure 64:
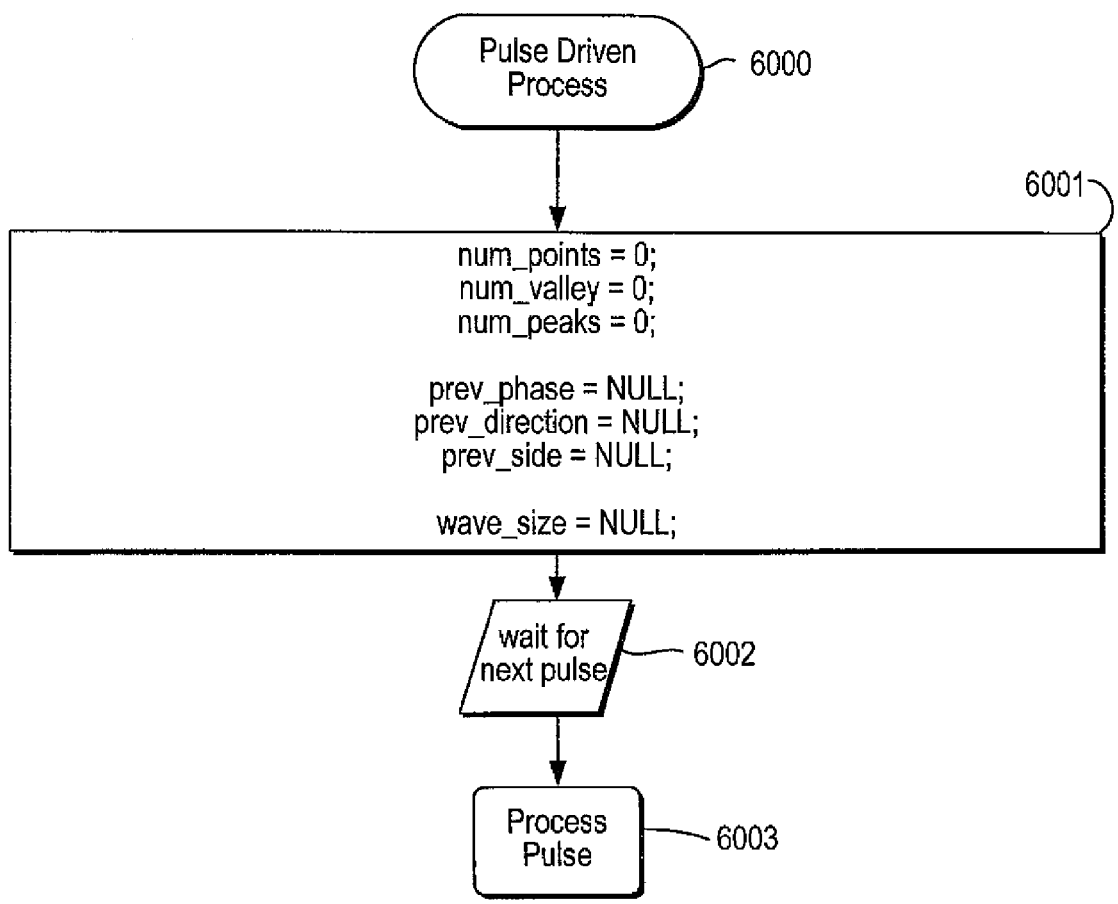
FIGS. 64-74 depict an exemplary flow process for an exemplary procedure for determining the phase of RSA waves in real-time, using the phase changes to detect the drop point, using the phase changes to detect the completion of a wave, and determining parasympathetic intensity of the newly formed wave.

This exemplary process begins at 6000 (FIG. 64). The first step, 6001, in the process is to clear all counters: num_points (tracks the number of pulses received), num_valley (tracks the number of wave valleys identified), num_peaks (tracks the number of wave peaks identified), prev_phase (keeps track of the previous wave phase), prev_direction (keeps track of the previous wave direction), prev_side (keeps track of the previous wave side), and wave_size (tracks the length of the last wave).

The process then flows to 6002 where it waits for the next pulse beat to arrive. When a new pulse is detected, the process flows to 6003, where the pulse is processed. After the pulse is processed, the flow returns to 6002 where it waits for another pulse to arrive.

Figure 65:
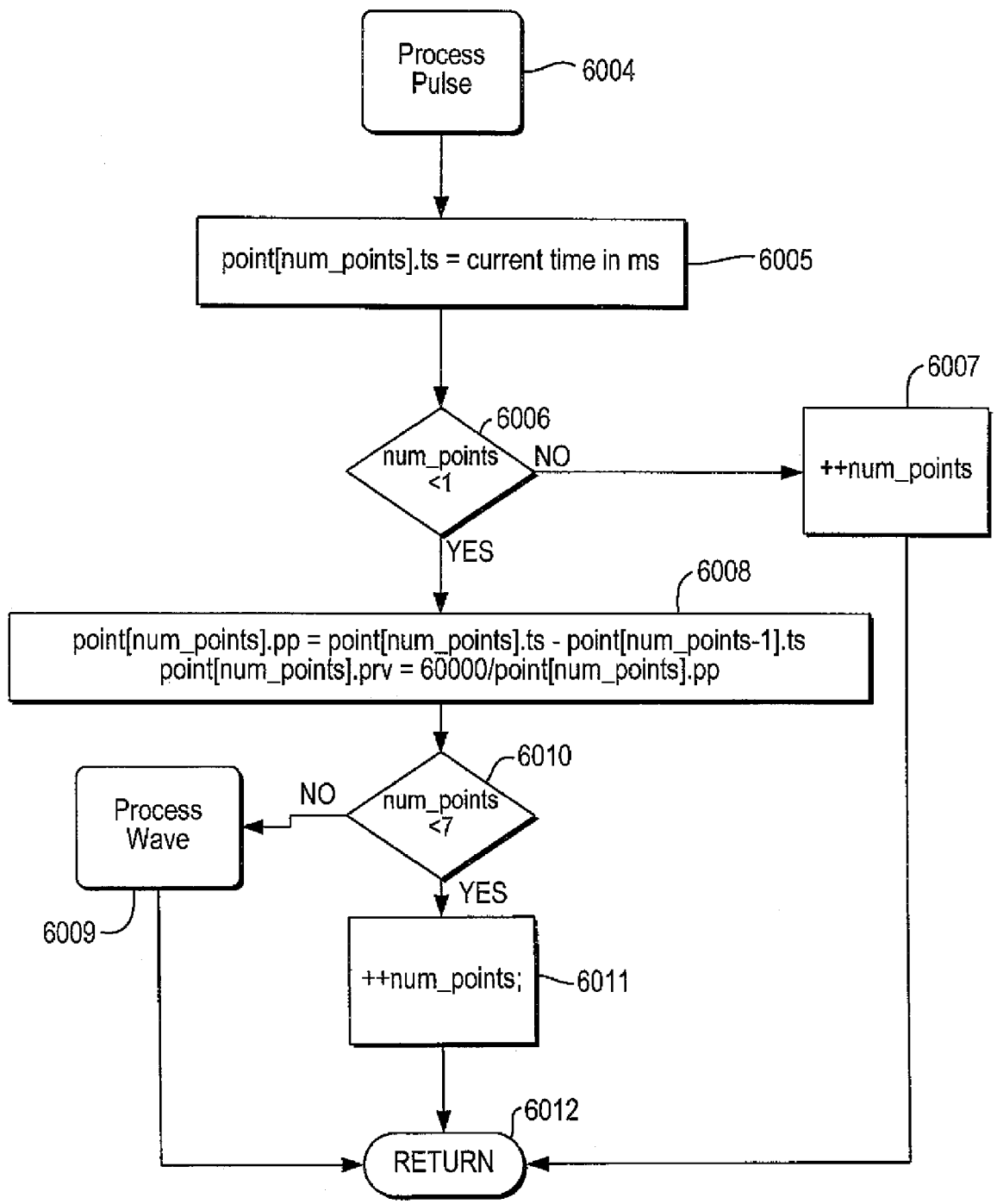

FIG. 65 describes an exemplary process for processing a pulse. This process begins at 6004. The first step in the process, at 6005, is to get and record the timestamp in ms of the new pulse beat, which is stored as point[num_points].ts. Then the process flows to 6006 where it assesses whether there are at least two points within the record. If not, the process flows to 6007 where the num_points counter is incremented. The process further continues to 6012 and returns. However, if there are at least two points in the record, the process flows to 6008.

At 6008 the peak-to-peak (pp) time of the last two points is computed and recorded as point[num_points].pp. Also, the pulse-rate-value represented by the pp time is computed and recorded as point[num_points].prv. Then the flow continues to 6010.

At 6010 the process assesses whether there are at least 8 points in the record. If not, the flow continues to 6011, and the num_points counter is incremented. The process further continues to 6012 and returns. However, if there are at least 8 points in the record, the process flows to 6009, which calls the Process Wave process. After the Process Wave process returns, the process in FIG. 65 flows to 6012 and returns.

Figure 66:
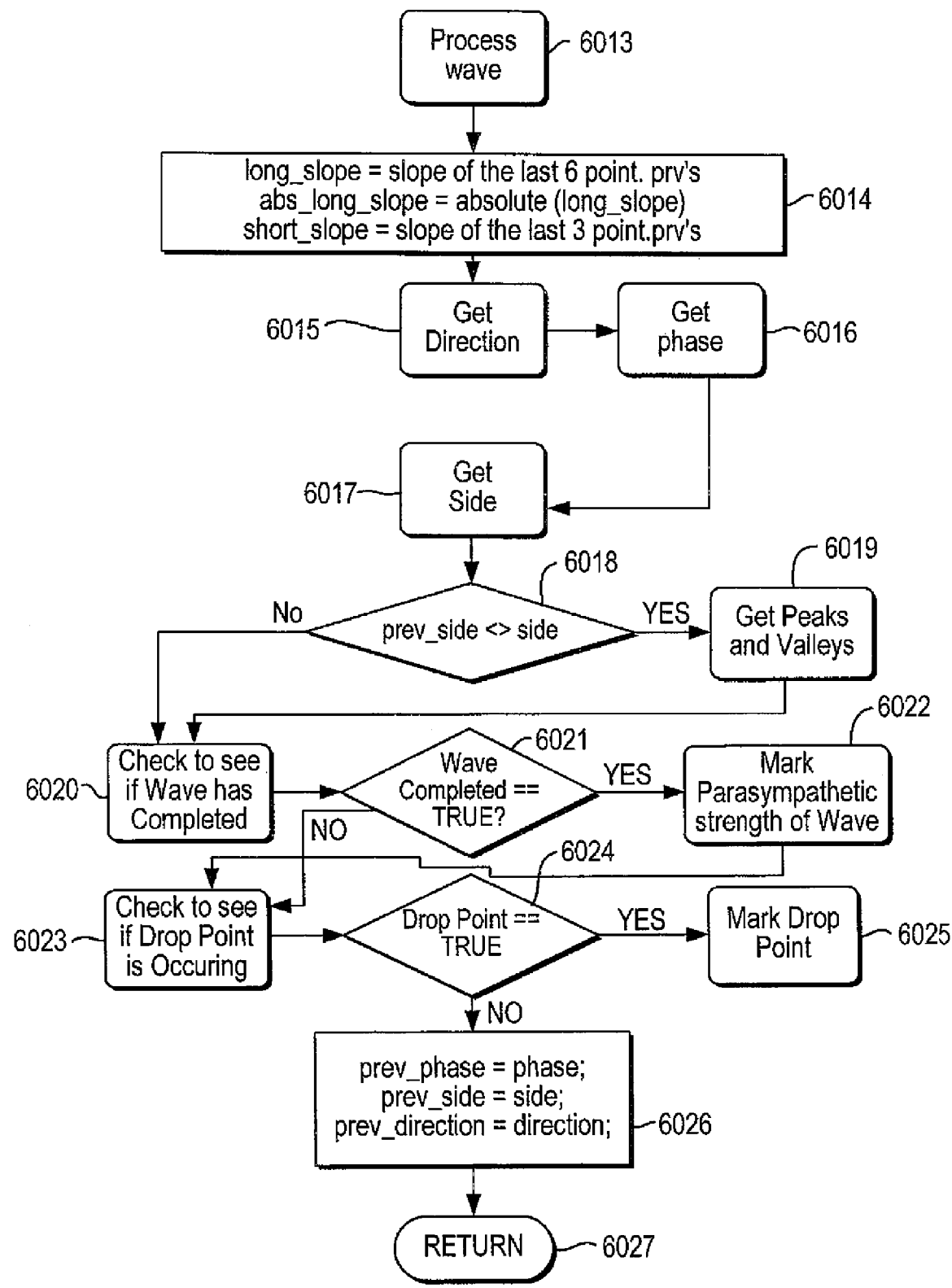

FIG. 66 describes a process for processing wave information. The process begins at 6013. The first step, at 6014, consists of computing and storing the long_slope, abs_long_slope, and the short_slope. The flow then continues to 6015 where the direction is determined by the Get Direction process. After the Get Direction process returns, the flow continues to 6016 where the phase of the wave is determined by the Get Phase process. After the Get Phase process has returned, the flow continues to 6017 where the side of the wave is determined by the Get Side process. After the Get Side process returns the flow continues to 6018.

At 6018 the process determines whether or not there has been a change in sides. If the wave has not changed sides, the process flows to 6020. Otherwise, the process flows to 6019 where the peaks and valleys are assessed by the Get Peaks and Valleys process. After this process returns, the flow continues to 6020.

At 6020, the process sets a flag indicating whether a wave has just completed or not via the Check to See if Wave has Completed process. After this process returns, the flow continues to 6021 where the Wave Completed flag is checked. If a wave has not just completed, the flow continues to 6023. Otherwise, the flow continues to 6022. At 6022 the Mark Parasympathetic Strength of Wave process delineates the newly formed wave, assesses its parasympathetic activity, and marks the activity under the wave using visual symbols. After this process returns, the flow continues to 6023.

At 6023, a flag is set indicating whether the drop point has just been crossed or not. The Check to See if Drop Point is Occurring process makes this determination and sets the flag accordingly. After this process has returned, the flow continues to 6024 where the flag is analyzed. If the drop point flag has not been set, the flow continues to 6026. Otherwise, the flow continues to 6025. At 6025 the process Mark Drop Point places a visual symbol above the wave at the drop point, and provides an auditory cue of the drop point. After this process returns, the flow continues to 6026.

At 6026, the prev_phase, prev_side, and prev_direction markers are assigned. Then the flow continues to 6027, where the Process Wave functions returns.

Figure 67:
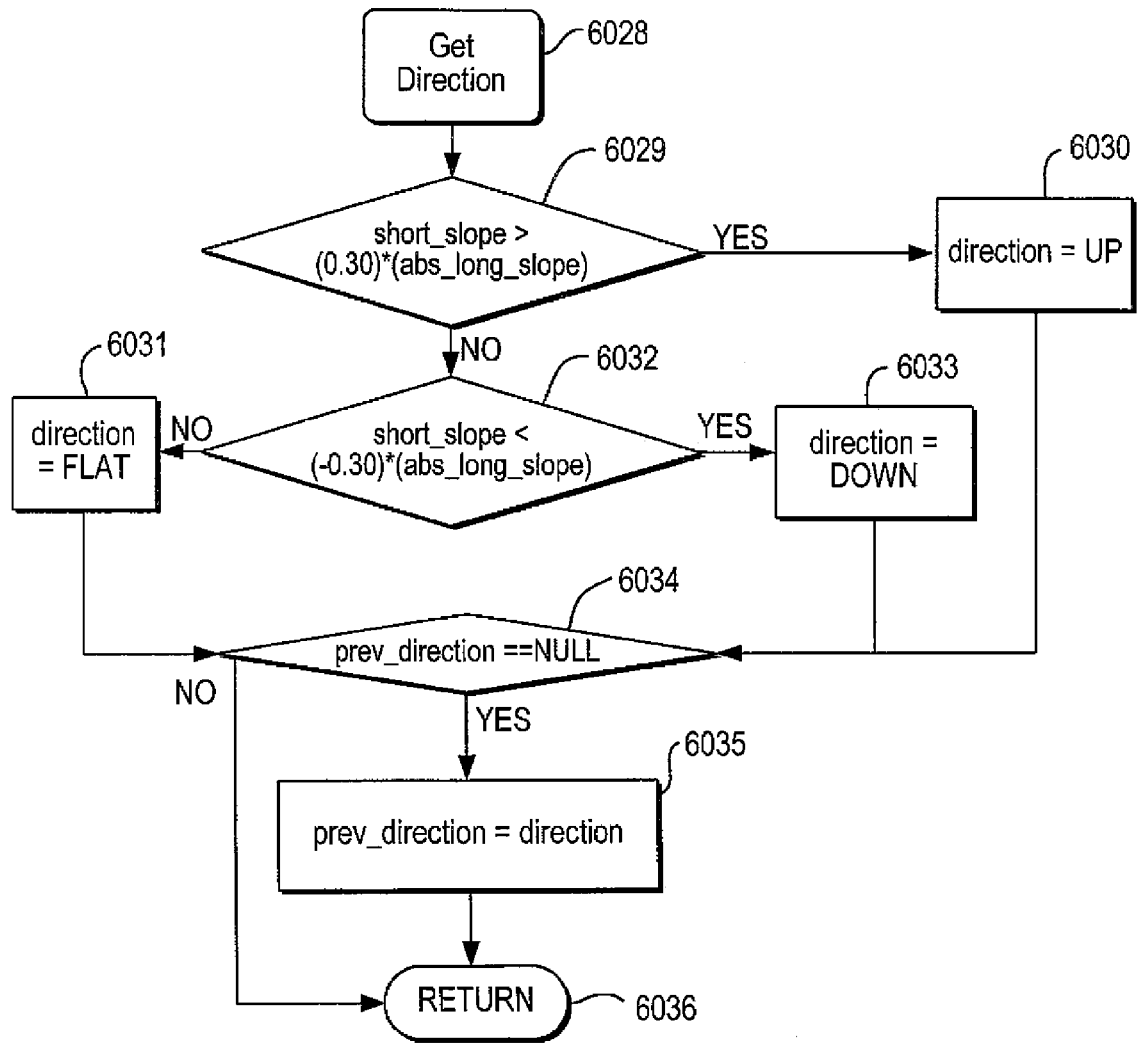

FIG. 67 describes the Get Direction process. The first step at 6029 checks to see if the short term slope is greater than 30% of the absolute long slope. If it is, the flow continues to 6030. Otherwise the flow continues to 6032.

At 6030 the direction is recorded as UP. Then the flow continues to 6034.

At 6032 the process checks to see if the short slope is less than 30% of −1× absolute long slope. If it is, the flow continues to 6033. If not, the flow continues to 6031.

At 6033 the direction is recorded as DOWN. Then the flow continues to 6034.

At 6031 the direction is recorded as FLAT. Then the flow continues to 6034.

At 6034, the process checks to see if the prev_direction has never been set yet. If it has not been set, the flow continues to 6035. Otherwise the flow continues to 6036 where the process returns.

At 6035, prev_direction gets recorded as the current direction (direction). The flow continues to 6036 where the process returns.

Figure 68:
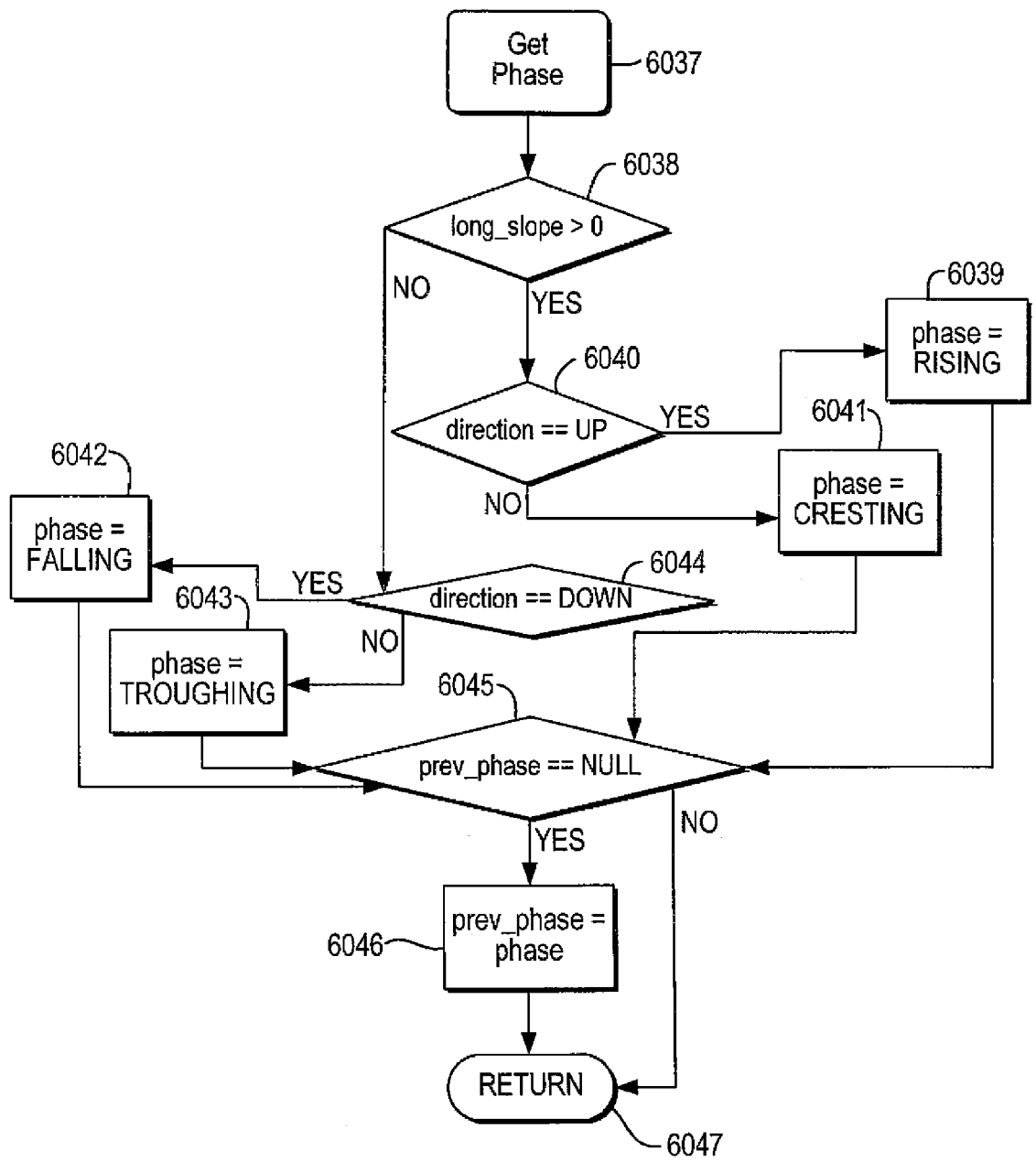

FIG. 68 describes an exemplary Get Phase process. The first step at 6038 checks to see if the long slope is positive. If it is, the flow continues to 6040. If it is not, the flow continues to 6044.

At 6040 the process checks to see if the direction is UP. If it is, the flow continues to 6039. If it is not, the flow continues to 6041.

At 6039 the phase is recorded as RISING. The flow then continues to 6045.

At 6041 the phase is recorded as CRESTING. The flow then continues to 6045.

At 6044 the process checks to see if the direction is DOWN. If it is, the flow continues to 6042. Otherwise the flow continues to 6043.

At 6042 the phase is recorded as FALLING. Then the flow continues to 6045.

At 6043 the phase is recorded as TROUGHING. Then the flow continues to 6045.

At 6045 the process checks to the see if the prev_phase has not yet been recorded. If it has not, the flow continues to 6046. If it has, the flow continues to 6047.

At 6046, the prev_phase is recorded as the current phase (phase). Then the flow continues to 6047.

At 6047, the Get Phase process returns.

Figure 69:
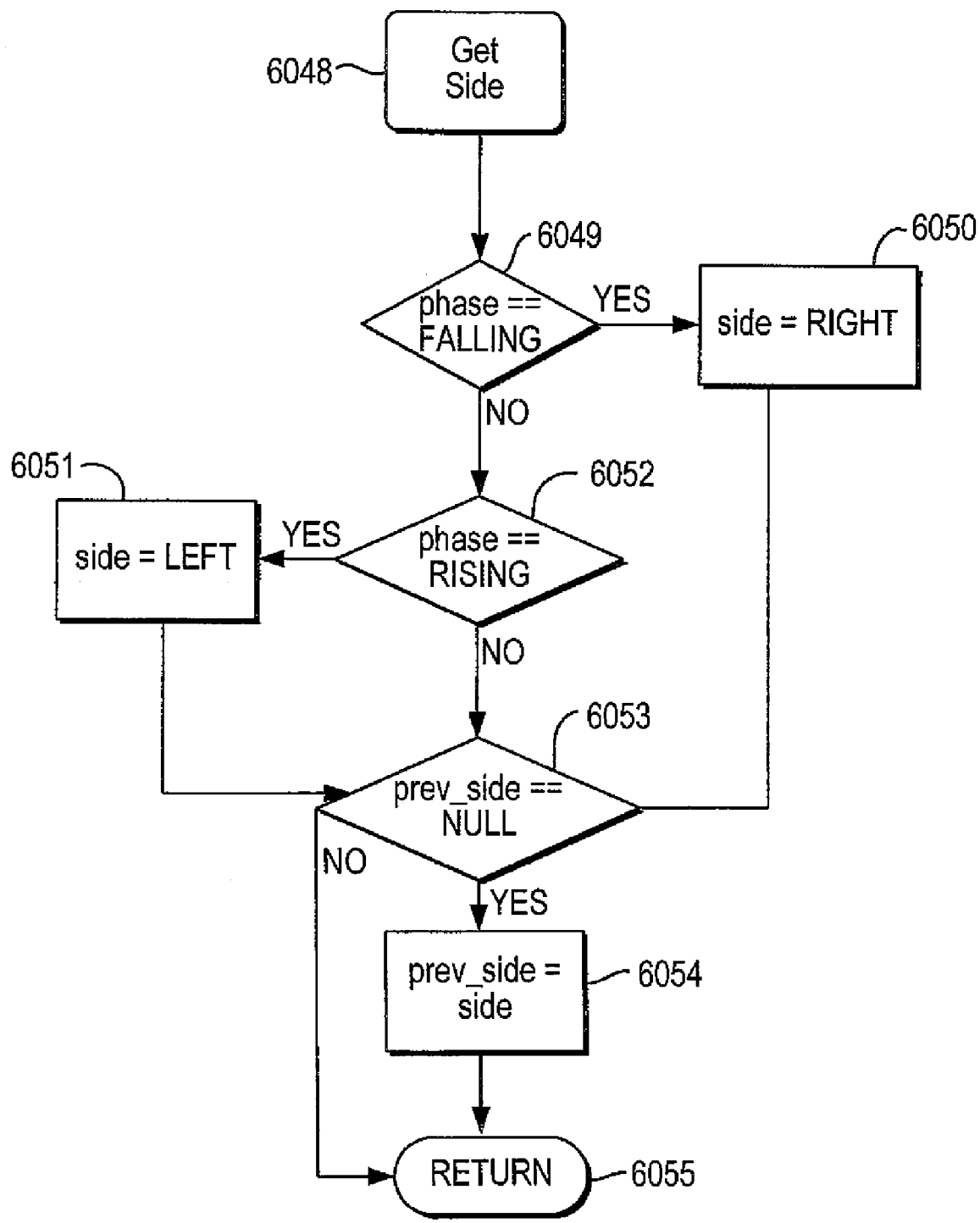

FIG. 69 describes the Get Side process. At 6049, the process checks to see if the phase is FALLING. If it is, the flow continues to 6050. If it is not, then the flow continues to 6052.

At 6050 the side is recorded as RIGHT. The flow continues to 6053.

At 6052 the process checks to see if the phase is RISING. If it is, the flow continues to 6051. Otherwise the flow continues to 6053.

At 6051 the side is recorded as LEFT. The flow continues to 6053.

At 6053 the process checks to see if the prev_side has yet been recorded. If it has not, then the flow continues to 6054. Otherwise the flow continues to 6055.

At 6054 the prev_side is recorded as the current side (side). The flow then continues to 6055. At 6055, the Get Side process returns.

Figure 70:
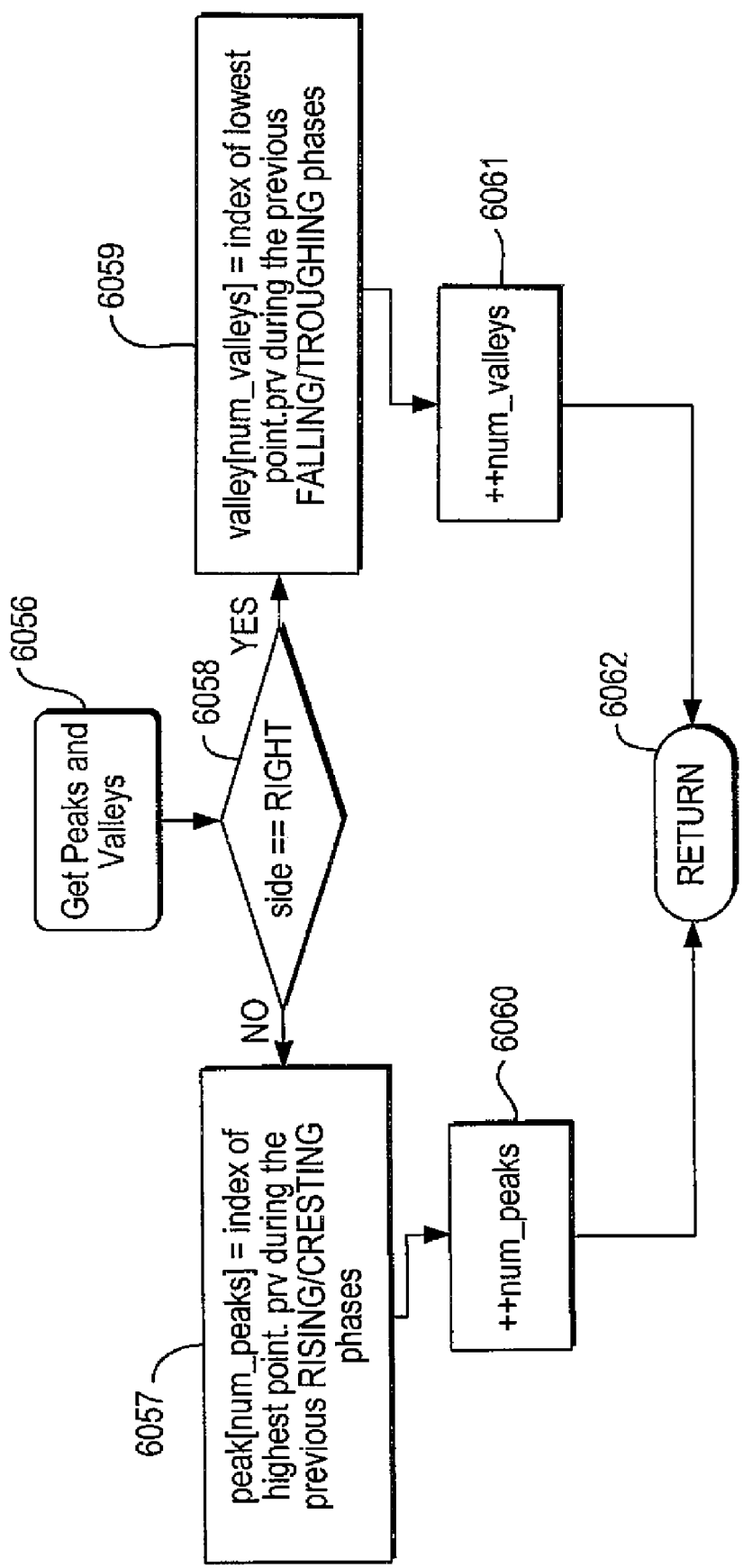

FIG. 70 describes an exemplary Get Peaks and Valleys process. In the first step at 6058, the process checks to see if the wave is currently forming the RIGHT side. If yes, the flow continues to 6059. If not, flow continues to 6057.

At 6057 the peak is identified as the highest prv value during the previous RISING and CRESTING phases. This value is recorded as peak[num_peaks]. Then the flow continues to 6060. At 6060, the num_peaks counter is incremented. Then the flow continues to 6062.

At 6059 the valley is identified as the lowest prv value during the previous FALLING and TROUGHING phases. This value is recorded as valley[num_valleys]. Then the flow continues to 6061. At 6061 the num_valleys counter is incremented. Then the flow continues to 6062. At 6062 the Get Peaks and Valleys process returns.

Figure 71:
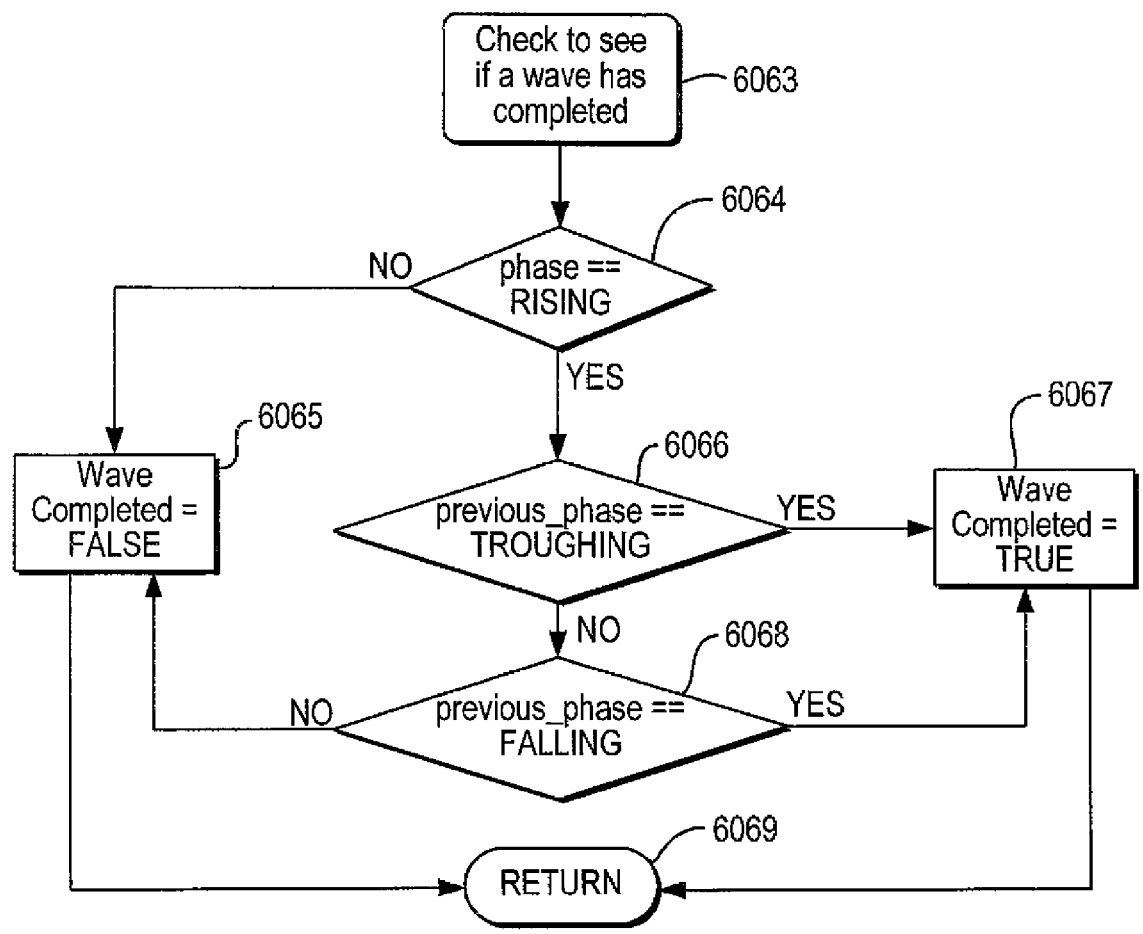

FIG. 71 describes the Check to See if a Wave Has Completed process. In the first step at 6064, the process checks to see if the current phase is RISING. If it is, then the flow continues to 6066. Otherwise, the flow continues to 6065.

At 6065 the wave completed flag is set to false. The flow then continues to 6069.

At 6066 the process checks to see if the previous_phase was TROUGHING. If so, the flow continues to 6067. Otherwise the flow continues to 6068.

At 6067 the wave completed flag is set to true. The flow then continues to 6069.

At 6068 the process checks to see if the previous phase was FALLING. If so, the flow continues to 6067. Otherwise the flow continues to 6069. At 6069 the Check to See if a Wave has Completed process returns.

Figure 72:
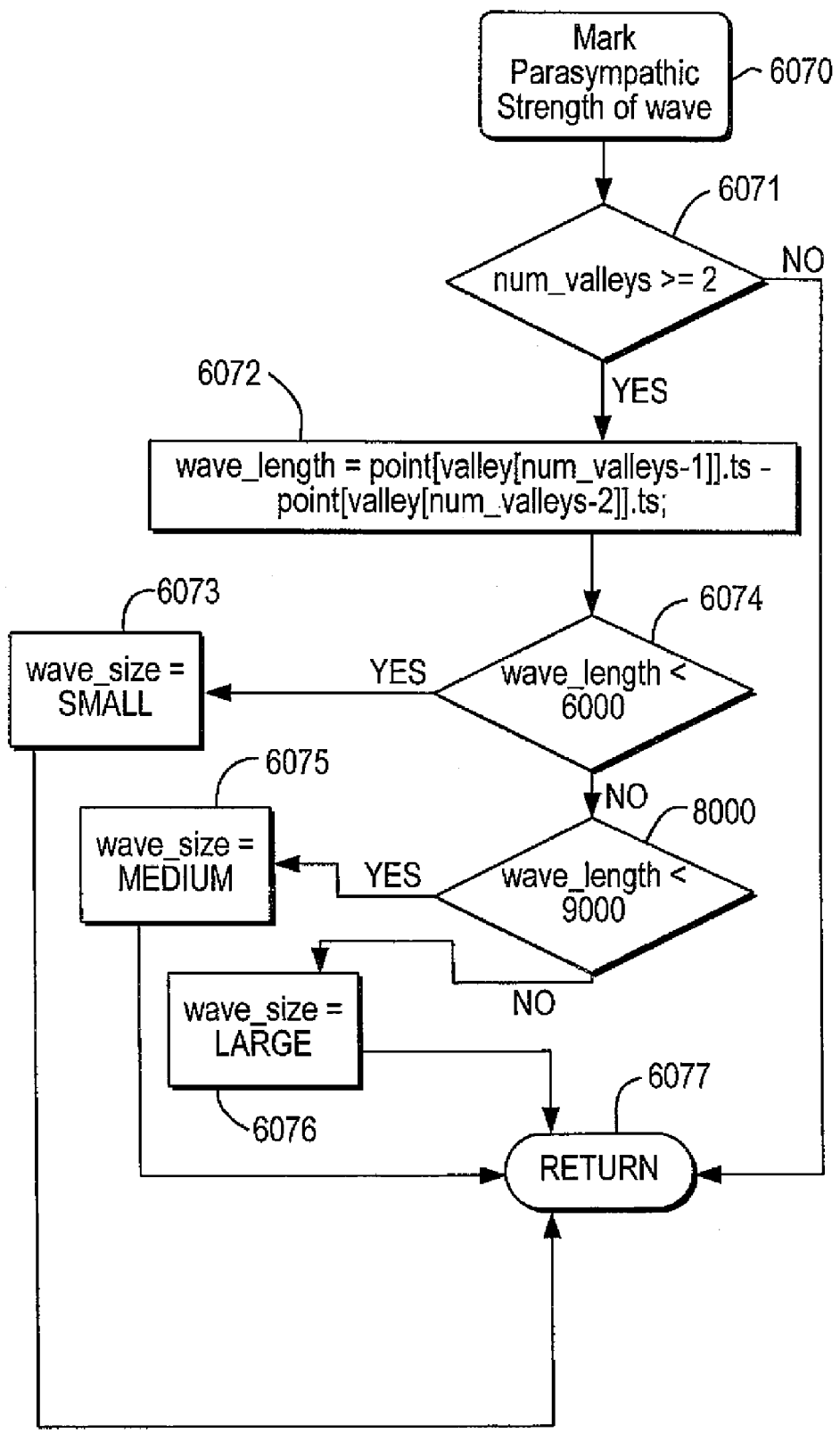

FIG. 72 describes an exemplary Mark Parasympathetic Strength of Wave process. In the first step at 6071 the process checks to see if there are at least two valleys in the record. If not, the flow continues to 6077. If yes, the flow continues 6072.

At 6072, the wave length is computed and recorded as wave_length. Then the flow continues to 6074. At 6074, the process checks to see if the wave length is less than 6 seconds. If it is, the flow continues to 6073. If it is not, the flow continues to 8000.

At 6073 the wave size is determined to be SMALL. This indicates very little parasympathetic activity when the wave was formed. The process can then visually mark the wave with an appropriate symbol indicating the parasympathetic activity. In the preferred embodiment, a one dot symbol is placed below the wave. The flow then continues to 6077.

At 8000 the wave length is checked to see if it is less than 9 seconds in length. If it is, the flow continues to 6075. Otherwise the flow continues to 6076.

At 6075 the wave size is marked as MEDIUM. A medium level of parasympathetic activity likely formed the wave. The process can then visually mark the wave with an appropriate symbol indicating the parasympathetic activity. In the preferred embodiment, a two dot symbol is placed below the wave. The flow continues to 6077.

At 6076 the wave size is marked as LARGE. A high amount of parasympathetic activity is represented by such waves. The process can then visually mark the wave with an appropriate symbol indicating the parasympathetic activity. In the preferred embodiment, a three dot symbol is placed below the wave. The flow continues to 6077.

At 6077 the Mark Parasympathetic Strength of Wave process then returns.

Figure 73:
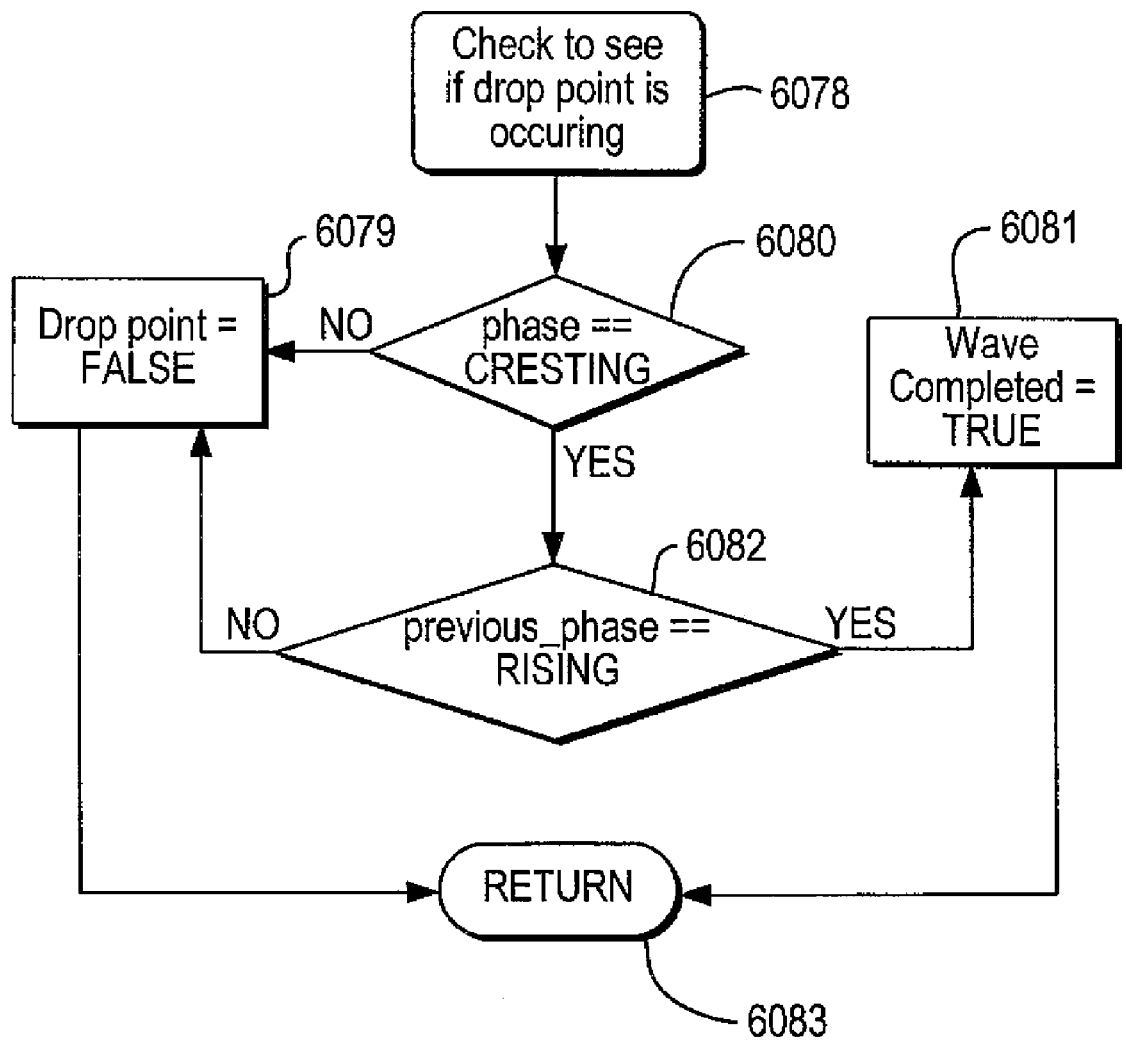

FIG. 73 describes an exemplary Check to See if Drop Point is Occurring process. In the first step at 6080, the process checks to see if the current phase is CRESTING. If it is, the flow continues to 6082. Otherwise, the flow continues to 6079.

At 6079 the drop point flag is set to false. Then the flow continues to 6083.

At 6082 the process checks to see if the previous phase was RISING. If it was, the flow continues to 6081. Otherwise, the flow continues to 6079.

At 6081 the drop point flag is set to true. Then the flow continues to 6083. At 6083 the Check to See if Drop Point is Occurring process returns.

Figure 74:
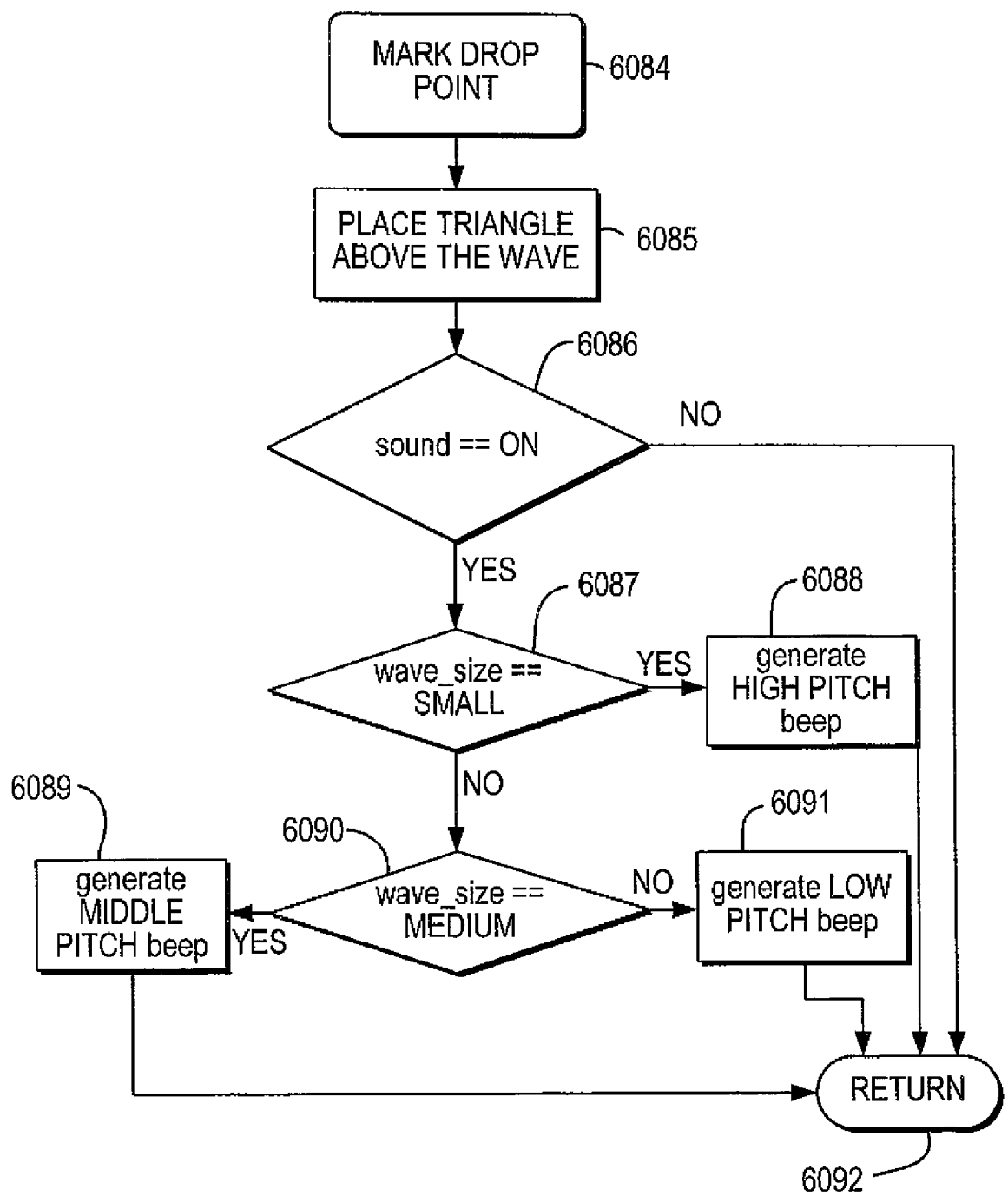

FIG. 74 describes an exemplary Mark Drop Point process. The first step at 6085, a triangle is placed above the wave. Then the flow continues to 6086 where the process checks to see if the sound is ON. If yes, the flow continues to 6087. If not, the flow continues to 6092.

At 6087 the process checks to see if the wave size is SMALL. If yes, the flow continues to 6088. If not, the flow continues to 6090.

At 6088 the device generates a high pitch beep. This auditorily indicates that the drop point has been encountered, as well as auditorily indicating that the previous wave was formed by a low level of parasympathetic activity. The flow then continues to 6092.

At 6090 the process checks to see if the wave size is MEDIUM. If it is, the flow continues to 6089. If it is not, the flow continues to 6091.

At 6089 the device generates a middle pitch beep. This auditorily indicates that the drop point has been encountered, as well as auditorily indicating that the previous wave was formed by a medium level of parasympathetic activity. The flow then continues to 6092.

At 6091 the device generates a low pitch beep. This auditorily indicates that the drop point has been encountered, as well as auditorily indicating that the previous wave was formed by a high level of parasympathetic activity. The flow then continues to 6092. At 6092 the Mark Drop Point process returns.

Exemplary procedures for determining, for example, the phase of RSA waves in real-time, using the phase changes to detect the drop point, using the phase changes to detect the completion of a wave, and determining parasympathetic intensity of the newly formed wave also may be implemented using the following pseudocode corresponding substantially to the flow processes depicted in FIGS. 64-74.

```
num_points = 0;
num_valley = 0;
num_peaks = 0;
prev_phase = NULL;
prev_direction = NULL;
prev_side = NULL;
wave_size = NULL;
Function Process_Pulse
point[num_points].ts = current time in mc
if (num_points < 1) then
{
    ++num_points;
```

```
        return;
    }
    point[num_points].pp = point[num_points].ts – point[num_points–1].ts
    point[num_points].prv = 60000/point[num_points].pp
    if (num_points < 7) then
    {
        ++num_points;
        return;
    }
    long_slope = slope of the last 6 point.prv's
    abs_long_slope = absolute (long_slope)
    short_slope = slope of the last 3 point.prv's
    if (short_slope > (0.30)*(abs_long_slope)) then direction = UP
    else if (short_slope < (–0.30)*(abs_long_slope)) then direction = DOWN
    else direction = FLAT;
    if (prev_direction == NULL) then prev_direction = direction
    if (long_slope > 0) then
    {
        if (direction == UP) then phase = RISING
        else phase = CRESTING;
    }
    else
    {
        if (direction == DOWN) then phase = FALLING
        else phase = TROUGHING;
    }
    if (prev_phase == NULL) then prev_phase = phase;
    if (phase == FALLING) then side = RIGHT;
    else if (phase == RISING) then side = LEFT;
    if (prev_side == NULL) then prev_side = side;
    If (prev_side < > side)
    {
        if (side == RIGHT) then
        {
            valley[num_valleys] = index of lowest point.prv during the previous
    FALLING/TROUGHING phases
            ++num_valleys;
        }
        else
        {
            peak[num_peaks] = index of highest point.prv during the previous
    RISING/CRESTING phases
            ++num_peaks;
        }
    }
    if ((phase == RISING) && ((previous_phase == TROUGHING) | | (previous_phase =
    FALLING)) then
    {
        if (num_valleys >= 2) then
        {
            wave_length = point[valley[num_valleys–1]].ts – point[valley[num_valleys–2]].ts;
            if (wave_length < 6000) then wave_size = SMALL
            else if (wave_length < 9000) then wave_size = MEDIUM
            else wave_size = LARGE;
            display wave points underneath previous wave
        }
    }
    if ((phase == CRESTING) && (previous_phase == RISING))
    {
        if (sound == ON)
        {
            if (wave_size == SMALL) then generate HIGH PITCH beep
            else if (wave_size == MEDIUM) then generate MIDDLE PITCH beep
            else generate LOW PITCH beep
        }
    }
    prev_phase = phase;
    prev_side = side;
    prev_direction = direction;
    Return from Function
```

Exemplary embodiments of the present invention also provide for the identification of peaks and valleys in real time without first identifying TD4 segments. Thus, values may be processed sequentially (e.g., one by one).

FIGS. 75-83 describe exemplary flow processes for an exemplary procedure for determining wave phase and delineating waves on a pulse-by-pulse basis. This exemplary embodiment uses a global directional indicator and the position of the points in the range to provide, for example, a greater accuracy of phase determination and wave delineation.

The exemplary processes and process flows illustrated in FIGS. 75 through 83, as well as any exemplary functions implementing such processes, including any auxilliary functions and/or processes called or utilized by such exemplary flow processes, are presented for illustrative purposes. Those skilled in the art will recognize that each exemplary process or function, whether at a called function or process level, or at an overall level for an entire top level process, can be implemented in a variety of functionally equivalent ways, and the description of FIGS. 75 to 83 which follows is in no way to be construed as limiting the wide variety of possible implementations in actual systems or devices, or requiring that the illustrative exemplary process flow be literally followed.

Bearing this in mind, for economy of expression as well as for elegance of illustration, the process flow in each of FIGS. 75 to 83 will next be described without continual reference to the exemplary nature of each stage or step in process flow, it being understood that in exemplary embodiments of the present invention functionally equivalent implementations can, for example, use different processes, as well as different sequences of processes and organizations of process flow, from that which is illustrated in FIGS. 75 through 83, to achieve equivalent functionalities. All of such alternate embodiments and equivalent functional implementations are understood to be within the methods and techniques of the present invention.

Figure 75:
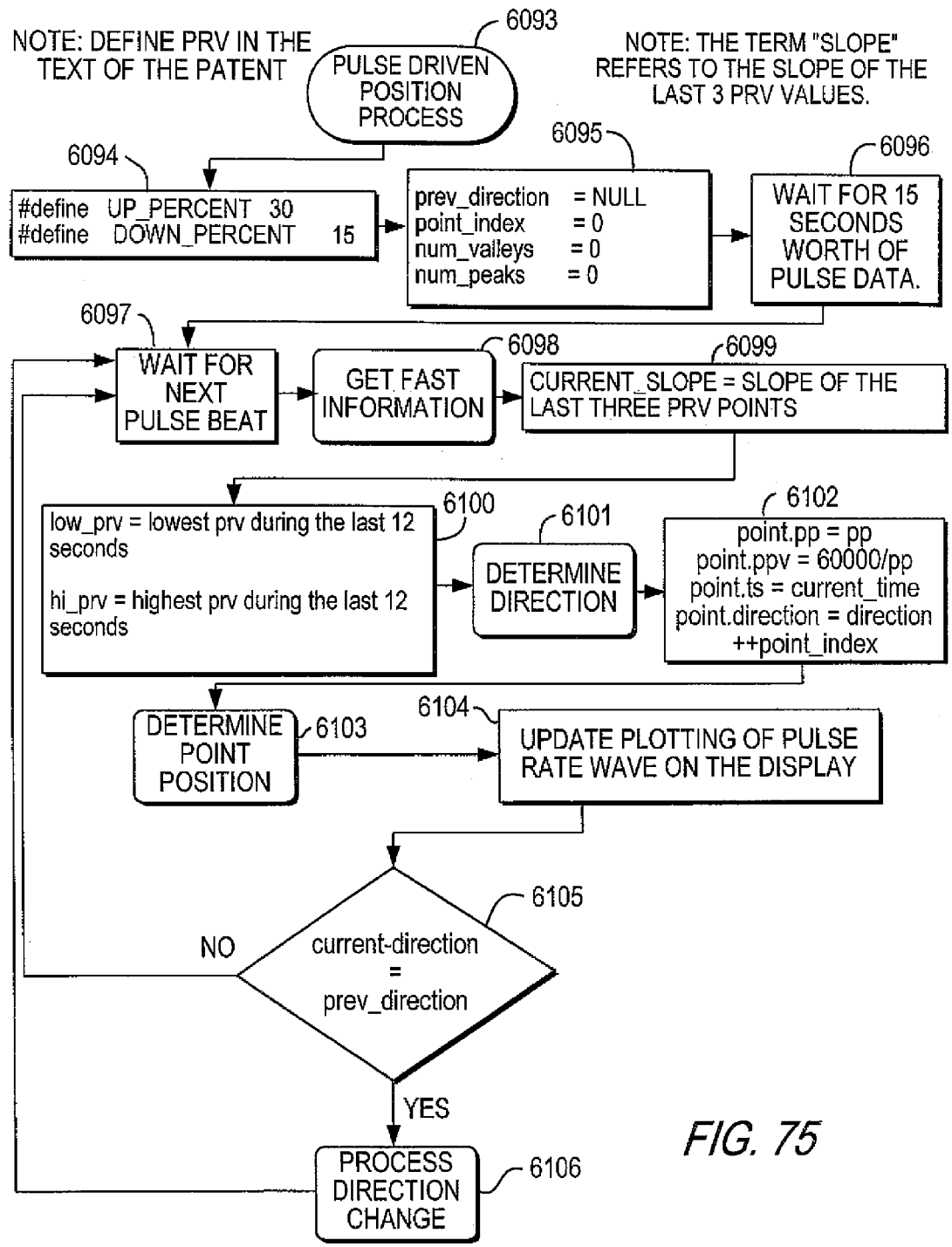
FIGS. 75-83 depict another exemplary flow process for an exemplary procedure for determining wave phase and delineating waves on a pulse-by-pulse basis.

As shown in FIG. 75, the process begins at 6093. The first step is 6094. At 6094, the process sets the UP PERCENT to 30 and the DOWN PERCENT to 15. Then the flow continues to 6095 where the counters and markers are initialized. Then the flow continues to 6096 where the process waits for 15 seconds worth of pulse information to arrive. Then the flow continues to 6097, where the process waits for the next pulse beat. After the next pulse beat is receive, the flow continues to 6098 where the global directional indicators are determined by the Get Fast Information process.

When that process returns, the flow continues to 6099 where the current slope is computed and recorded. Then the flow continues to 6100 where the lowest prv of the last 12 seconds and the highest prv of the last twelve seconds are computed and recorded. This provides us with the range of prv values over last 12 seconds.

The flow then continues to 6101. At 6101 the Determine Direction process determines the direction of the wave. When this process returns, the flow continues to 6102 where the current points peak-to-peak (pp) value, pulse rate value (prv), timestamp (ts), direction, and point index are computed and recorded.

Then the flow continues to 6103 where the Get Point Position process determines what part of the range the current point is within. A position of 100 means the point is at the very top or is above the range. A position of 0 means the point is at the very bottom or below the range. A value between 0 and 100 indicates the percent height of the point within the range.

When the Get Point Position process returns, the flow continues to 6104. At 6104 the wave plotting is update on the display. That is, the recently received prv value is plotted on the display. Then the flow continues to 6105.

At 6105 the process checks to see if the direction had changed when the last prv was received. If the direction did not change, the flow continues to 6097 where the process waits for the next pulse. If the direction did change, the flow continues to 6106 where the change of direction is handled by the Process Direction Change process. When this process returns, the flow continues to 6097 where the process waits for the next pulse to arrive.

Figure 76:
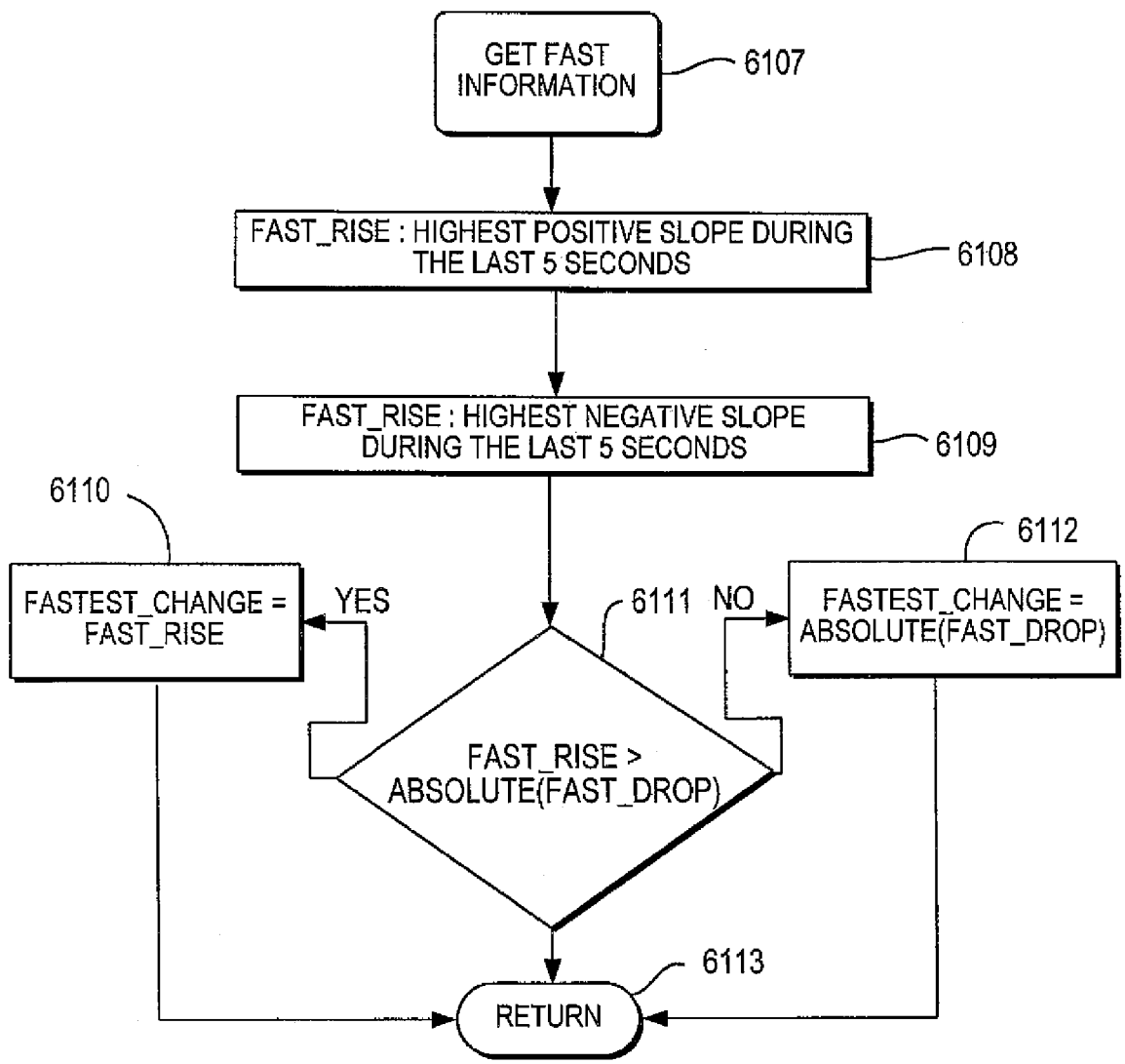

FIG. 76 describes an exemplary Get Fast Information process. In the first step at 6108, the highest positive slope during the last 5 seconds is recorded as fast_rise. Then the flow continues to 6109. At 6109 the highest negative slope during the last 5 seconds is recorded as fast_drop. Then the flow continues 6111.

At 6111 the process checks to see if the fast_rise is greater than the absolute value of the fast_drop. If it is, then the flow continues to 6110. If it is not, then the flow continues to 6112.

At 6110, the fast_rise is recorded as the fastest_change. Then the flow continues to 6113.

At 6112 the absolute value of fast_drop is recorded as the fastest_change. Then the flow continues to 6113. At 6113 the Get Fast Information process returns.

Figure 77:
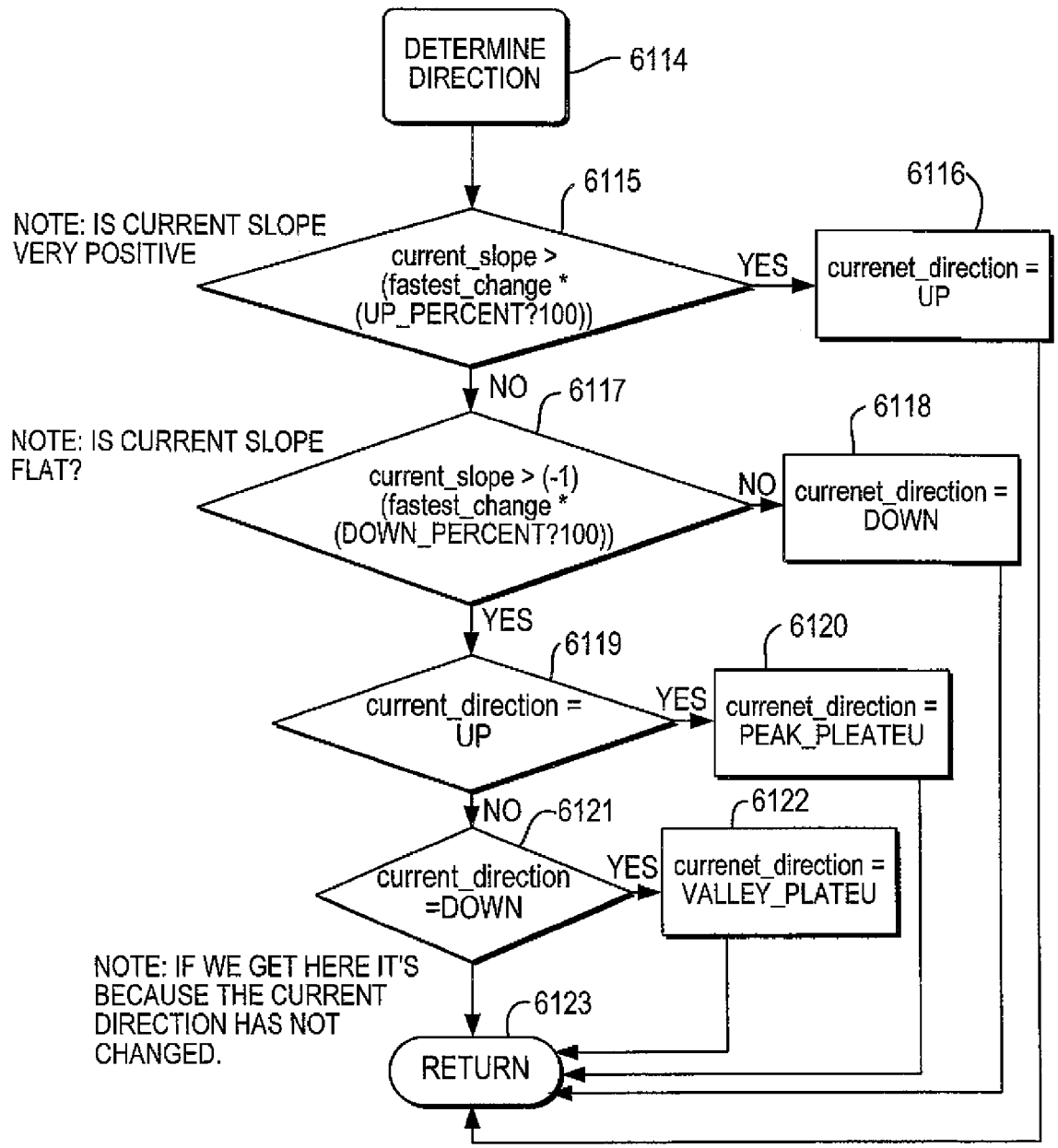

FIG. 77 describes an exemplary Determine Direction process. In the first step of the process at 6115 the process checks to see if the current slope is greater then UP PERCENT% of the fastest change. If it is, then the flow continues to 6116. If it is not then the flow continues to 6117.

At 6116 the current direction is recorded as UP. Then the flow continues to 6123.

At 6117 the process checks to see if the current slope is less than −1× DOWN PERCENT% of the fastest change. If it is, then the flow continues to 6119. If it is not then the flow continues to 6118.

At 6118 the current direction is recorded as DOWN. Then the flow continues to 6123.

At 6119 the process checks to see if the current direction is UP. If it is, then the flow continues to 6120. If it is not, then the flow continues to 6121.

At 6120 the current direction is recorded as PEAK_PLATEAU, also known as CREST. Then the flow continues to 6123.

At 6121 the process checks to see if the current direction is DOWN. If it is, then the flow continues to 6122. If it is not then the flow continues to 6123.

At 6122 the current direction is recorded as VALLEY_PLATEAU, also known as TROUGH. Then the flow continues to 6123. At 6123 the Determine Direction process returns.

Figure 78:
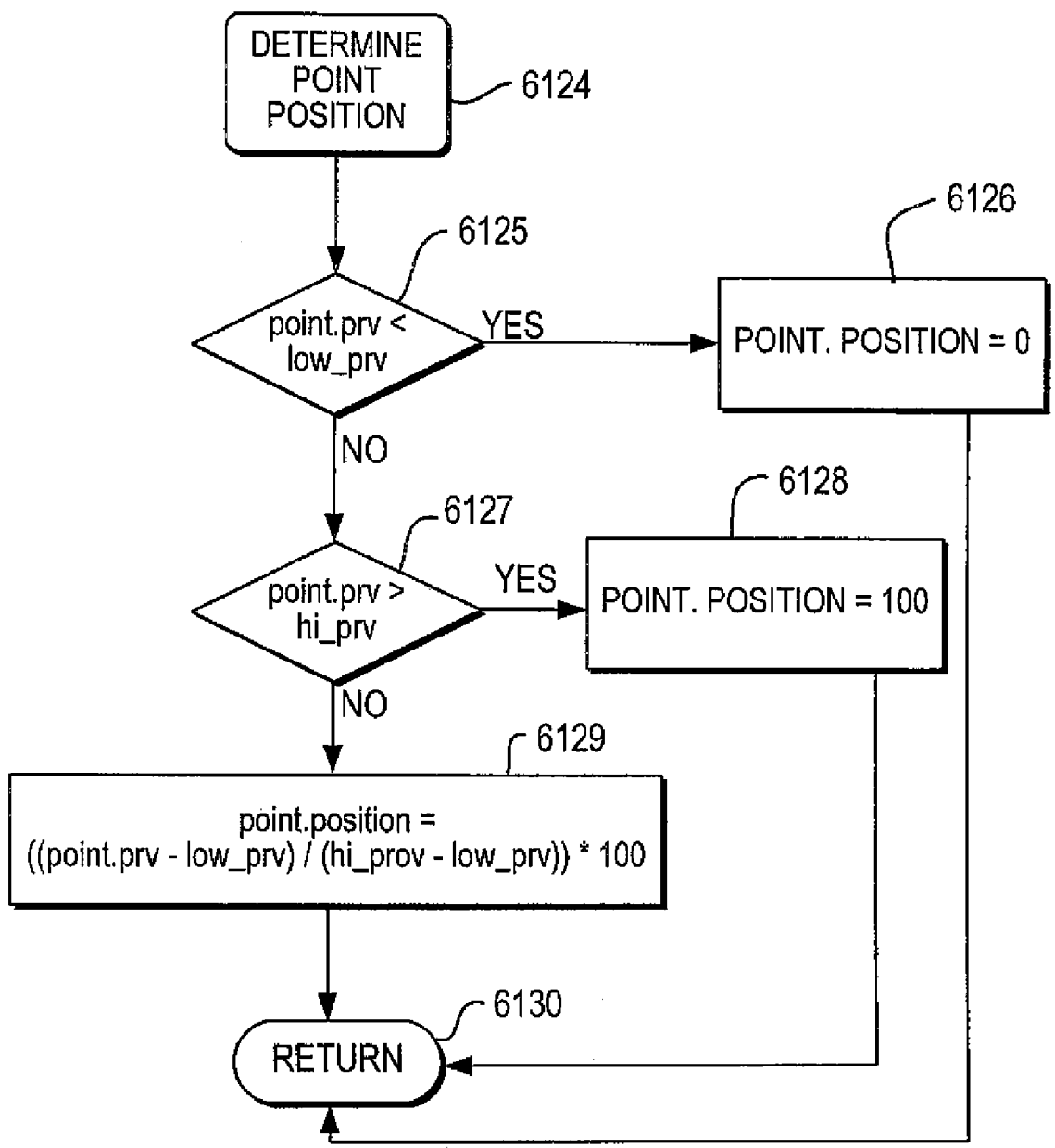

FIG. 78 describes an exemplary Determine Point Position process. In the first step at 6125 the process checks to see if the current point's prv is less than the lowest prv in the range. If it is, the flow continues to 6126. If it is not, then the flow continues to 6127.

At 6126 the point position is recorded as 0. Then the flow continues to 6130.

At 6127 the process checks to see if the current point's prv is greater than the highest prv in the range. If it is, then the flow continues to 6128. If it is not, then the flow continues to 6129.

At 6128 the point position is recorded as 100. Then the flow continues to 6130.

At 6129 the point's relative position in the range is computed and recorded. Then the flow continues to 6130. At 6130 the Determine Point Position process returns.

Figure 79:
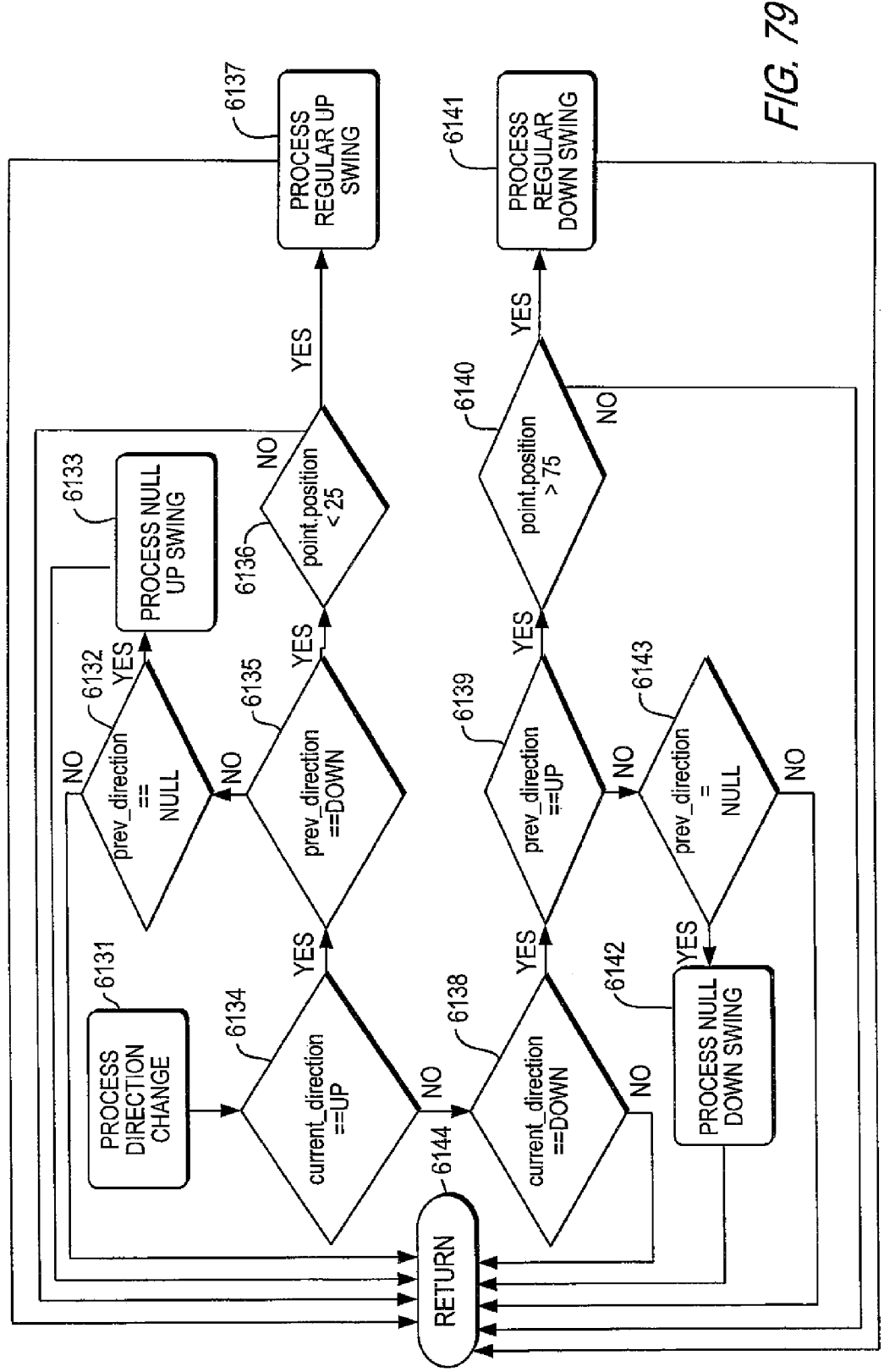

FIG. 79 describes an exemplary Process Direction Change process. In the first step at 6134, the process checks to see if the current direction is UP. If it is then the flow continues to 6135. If it is not then the flow continues to 6138.

At 6135 the process checks to see if the previous direction was DOWN. If it was then the flow continues to 6136. If it was not, then the flow continues to 6132.

At 6132 the process checks to see if the previous direction had ever been recorded. If it had not, the flow continues to 6133. If it had, the flow continues to 6144.

At 6133 the up swing of the wave is handled by the Process Null Up Swing process. After this process returns, the flow continues to 6144.

At 6136 the process checks to see if the current point position is in the bottom 25% of the range. If it is then the flow continues to 6137. If it is not, then the flow continues to 6144.

At 6137 the up swing of the wave is handled by the Process Regular Up Swing process. After this process returns, the flow continues to 6144.

At 6138 the process checks to see if the current direction is DOWN. If it is, then the flow continues to 6139. If it is not then the flow continues to 6144.

At 6139 the process checks to see if the previous direction was UP. If it was, then the flow continues to 6140. If it was not then the flow continues to 6143.

At 6140 the process checks to see if the current point's position is in the top 75% of the range. If it is, then the flow continues to 6141. If it is not, then the flow continues to 6144.

At 6141 the wave's down swing is handled by the Process Regular Down Swing process. After this process returns, the flow continues to 6144.

At 6143 the process checks to see if the previous direction has ever yet been recorded. If it has not then the flow continues to 6142. If it has, then the flow continues to 6144.

At 6142 the wave's down swing is handled by the Process Null Down Swing process. When this process returns, the flow continues to 6144. At 6144 the Process Change Direction process returns.

Figure 80:
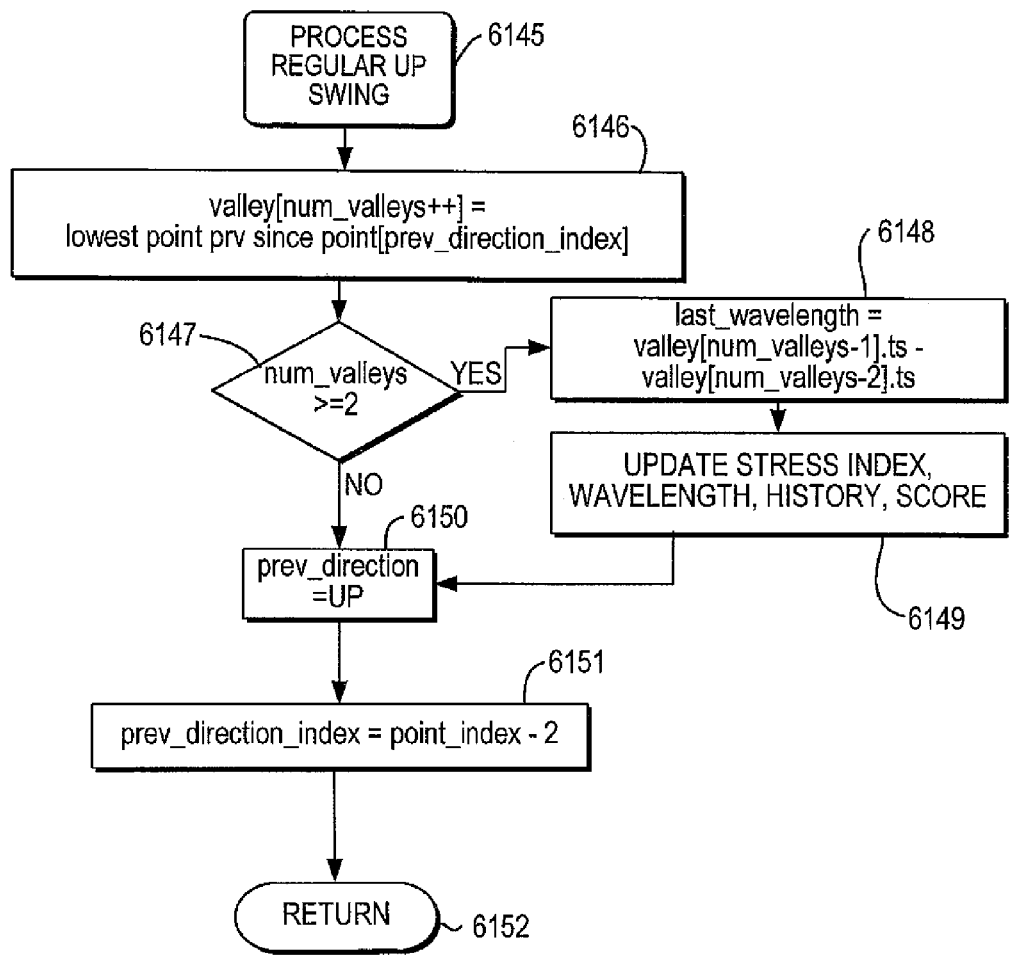

FIG. 80 describes an exemplary Process Regular Up Swing process. In the first step at 6146, the lowest prv since the previous direction began is recorded as the newest valley point. Then the flow continues to 6147.

At 6147 the process checks to see if there are at least two valley points on record. If there are, the flow continues to 6148. If there are not, then the flow continues to 6150.

At 6148 the wavelength of the last wave is computed and recorded. Then the flow continues to 6149. At 6149 the stress index is computed, and the score is computed. Also, the stress index, wavelength, history, score, and other wave based metrics are displayed on the screen. Then the flow continues to 6150.

At 6150 the previous direction is recorded as being UP. Then the flow continues to 6151. At 6151 the previous direction index is recorded as having occurred two points ago. Then the flow continues to 6152 where the Process Regular Up Swing process returns.

Figure 81:
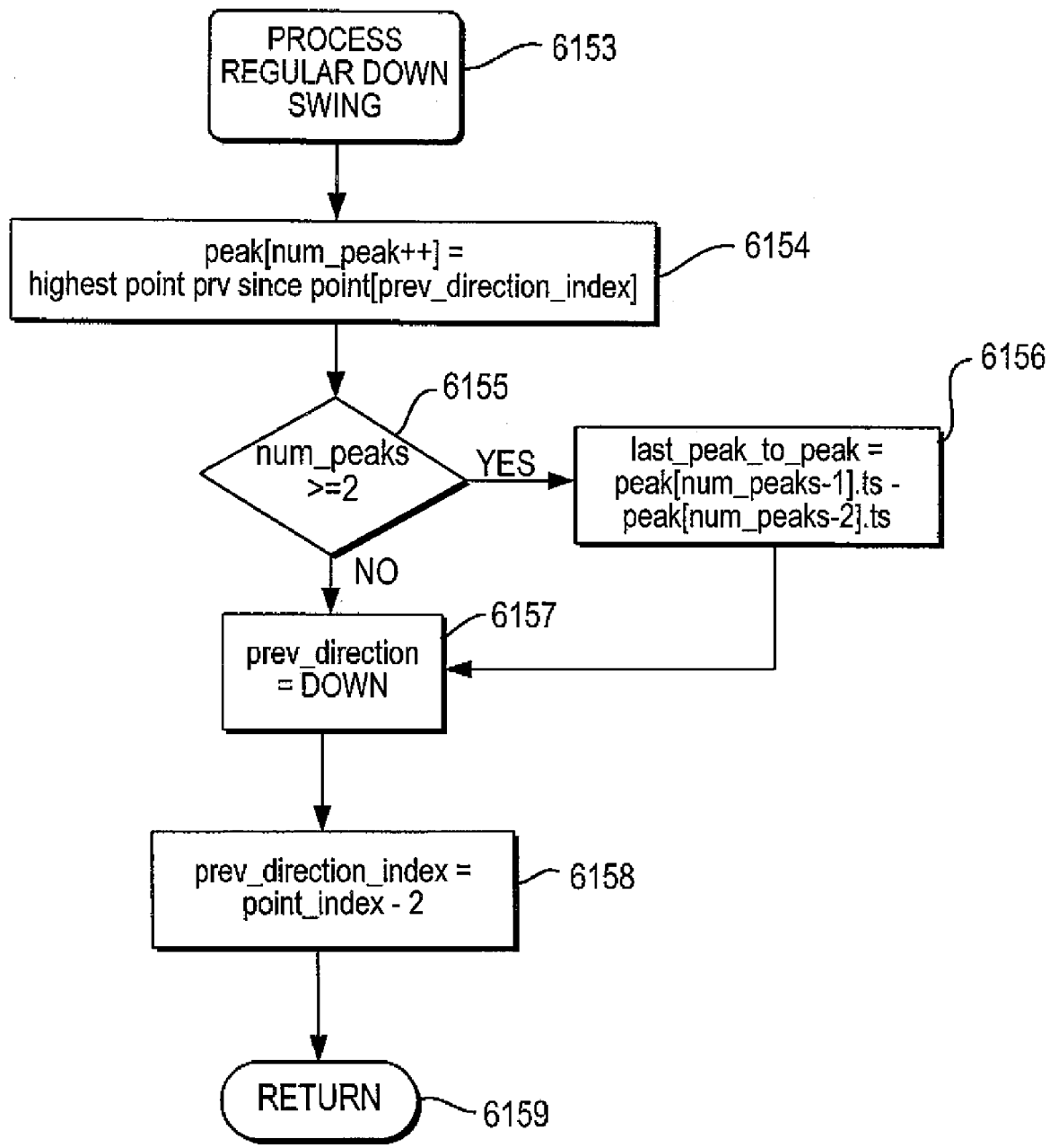

FIG. 81 describes an exemplary Process Regular Up Swing process. In the first step at 6154, the highest prv since the last direction change began is recorded as the next peak point. Then the flow continues to 6155.

At 6155 the process checks to see if there are at least two peaks recorded. If there are then the flow continues to 6156. If there are not, then the flow continues to 6157.

At 6156 the timestamps of the last two peaks are subtracted to compute and record the last peak to peak time. Then the flow continues to 6157.

At 6157 the previous direction indicator is set to DOWN. Then the flow continues to 6158 where the previous direction index is set to two points ago. Then the flow continues to 6159 where the Process Regular Up Swing Process returns.

Figure 82:
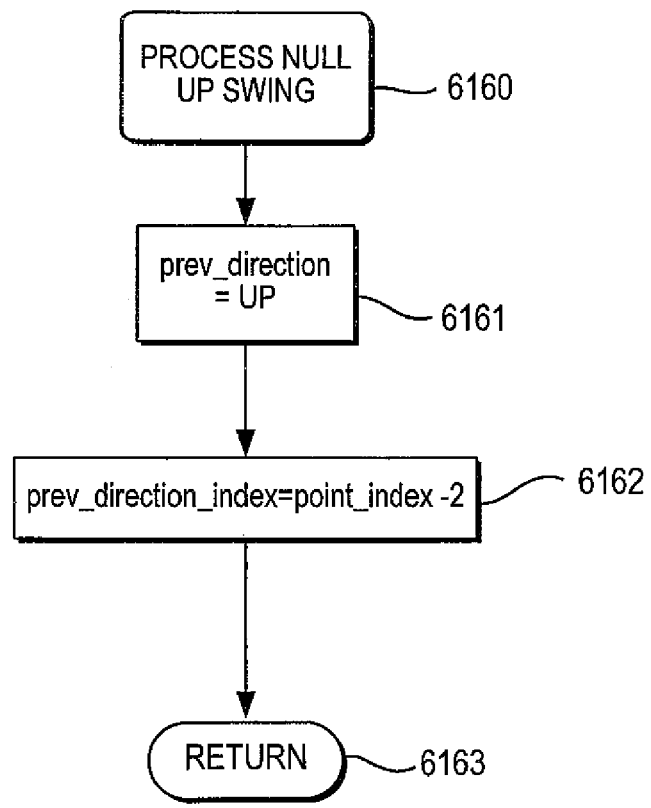

FIG. 82 describes an exemplary Process Null Up Swing process. In the first step at 6161 the previous direction indicator is set to UP. Then the flow continues to 6162, where the previous direction index is set to two points ago. Then the flow continues to 6163 where the Process Null Up Swing process returns.

Figure 83:
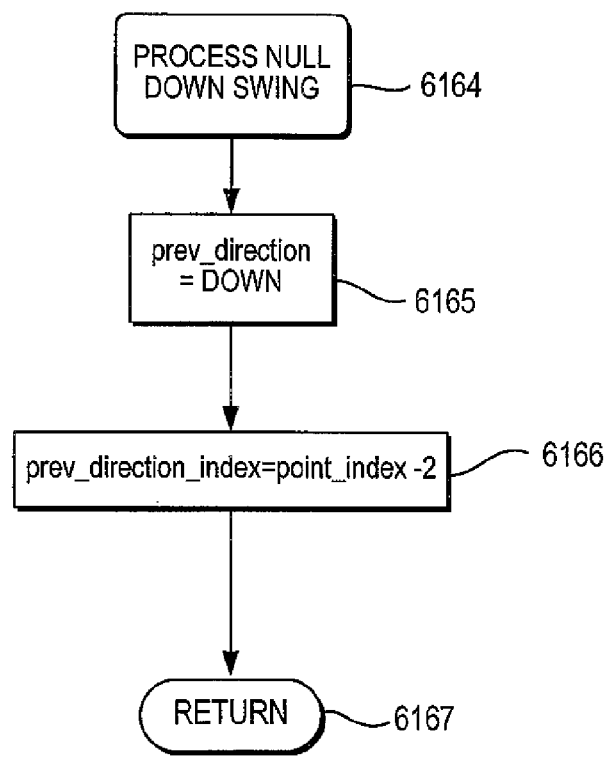

FIG. 83 describes an exemplary Process Null Down Swing process. In the first step at 6164 the previous direction indicator is set to DOWN. Then the flow continues to 6165, where the previous direction index is set to two points ago. Then the flow continues to 6167 where the Process Null Up Swing process returns.

Exemplary procedures for determining, for example, wave phase and delineating waves on a pulse-by-pulse basis also may be implemented using the following pseudocode corresponding substantially to the flow processes depicted in FIGS. 75-83.

```
//point_structure
    pp, prv, ts, direction
//define
#define     UP_PERCENT          30
#define     DOWN_PERCENT        15
//initialize
prev_direction      = NULL
point_index         = 0
num_valleys         = 0
num_peaks           = 0
Wait for 15 seconds worth of data. Use a rolling window of 15 seconds. Index each point with
point index
the term slope refers to the slope of three prv points
// main loop
fast_rise : highest positive slope during the last 5 seconds
fast_drop : highest negative slope during the last 5 seconds
if (fast_rise > absolute(fast_drop)) then
     fastest_change = fast_rise
else
     fastest_change = absolute(fast_drop)
current_slope = slope of the last three prv points
[Begin New Code]
low_prv = lowest prv during the last 12 seconds
hi_prv + highest prv during the last 12 seconds
[End New Code]
//determine direction
if (current_slope > (fastest_change * (UP_PERCENT/100))) then
current_direction = UP
else if (current_slope > (-1) * (fastest_change) * (DOWN_PERCENT/100))) then
{
     if current_direction = UP then current_direction = PEAK_PLATEAU
     else if current_direction = DOWN then current_direction = VALLEY_PLATEAU
}
```

```
else current_direction = DOWN
point.pp = pp
point.prv = 60000/pp
point.ts = current_time
point.direction = direction
[Begin New Code]
if (point.prv < low_prv) then
    point.position = 0
else if (point.prv > hi_prv) then
    point.position = 100
else point.position = ((point.prv – low_prv) / (hi_prov – low_prv)) * 100
[End New Code]
update prv display
if (current-direction != prev_direction)
{
    [Begin New Code]
    if ((current_direction == UP) && (prev_direction == DOWN) && (point.position < 25))
then
    [End New Code]
    {
        valley[num_valleys++] = lowest point prv since point[prev_direction_index]
        if (num_valleys >= 2) then
        {
            last_wavelength = valley[num_valleys-1].ts – valley[num_valleys-2].ts
            Update Stress Index, Wavelength, history, score
        }
        prev_direction = UP
        prev_direction_index = point_index – 2
    }
    [Begin New Code]
    if ((current_direction == DOWN) && (prev_direction == UP) && (point.position > 75))
then
    [End New Code]
    {
        peak[num_peaks++] = highest point prv since point[prev_direction_index]
        if (num_peaks >= 2) then
            last_peak_to_peak = peak[num_peaks-1].ts – peak[num_peaks-2].ts
        prev_direction = DOWN
        prev_direction_index = point_index – 2
    }
}
if ((current_direction == UP) && (prev_direction == NULL))
{
    prev_direction = UP
    prev_direction_index = point_index – 2
}
if ((current_direction == DOWN) && (prev_direction == NULL))
{
    prev_direction = DOWN
    prev_direction_index = point_index – 2
}
}
```

The present invention also provides processes for determining both the drop point and the completion of RSA waves in real time rather than on a pulse-by-pulse basis. FIGS. 84-87 describe two exemplary processes that run simultaneously. The first process, Realtime Process 1 (at 6168) is executed on a pulse by pulse basis. The second process, Realtime Process 2 (at 6171), is executed every 250 ms. The two processes work together to allow for the real time detection of the drop point and the real time detection of the termination of the current wave.

The exemplary processes and process flows illustrated in FIGS. 84 through 87, as well as any exemplary functions implementing such processes, including any auxilliary functions and/or processes called or utilized by such exemplary flow processes, are presented for illustrative purposes. Those skilled in the art will recognize that each exemplary process or function, whether at a called function or process level, or at an overall level for an entire top level process, can be implemented in a variety of functionally equivalent ways, and the description of FIGS. 84 to 87 which follows is in no way to be construed as limiting the wide variety of possible implementations in actual systems or devices, or requiring that the illustrative exemplary process flow be literally followed.

Bearing this in mind, for economy of expression as well as for elegance of illustration, the process flow in each of FIGS. 84 to 87 will next be described without continual reference to the exemplary nature of each stage or step in process flow, it being understood that in exemplary embodiments of the present invention functionally equivalent implementations can, for example, use different processes, as well as different sequences of processes and organizations of process flow, from that which is illustrated in FIGS. 84 through 87, to achieve equivalent functionalities. All of such alternate embodiments and equivalent functional implementations are understood to be within the methods and techniques of the present invention.

Figures 84A, 84B:
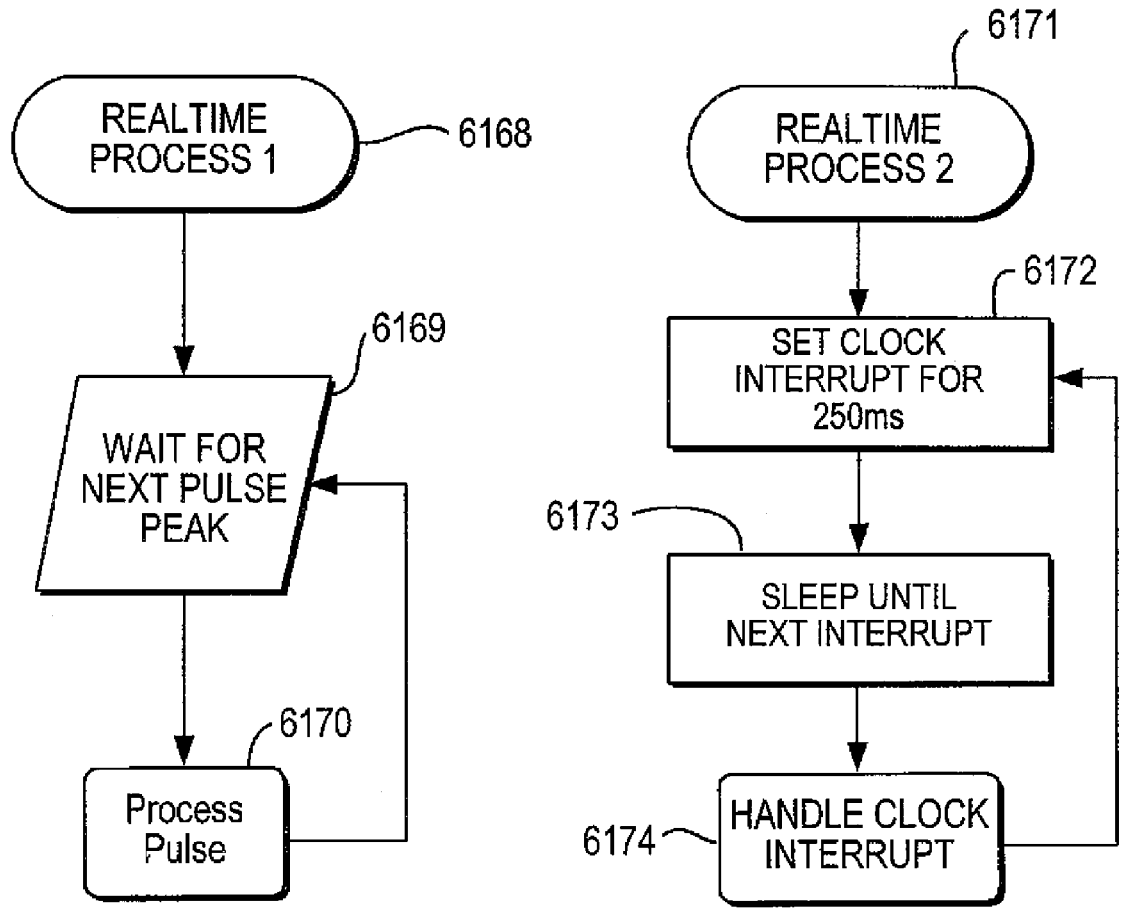
FIGS. 84-87 depict an exemplary flow process for an exemplary procedure for determining both the drop point and the completion of a wave in real time.

FIG. 84 describes the interrupt nature of the two exemplary processes. Realtime process 1 begins at 6168. In the first step at 6169, the process waits for the next pulse to be received. When a pulse is received, the flow continues to 6170, where the pulse is handled by the Handle Pulse Peak process. When this process returns, the flow continues back to 6169, where the process waits for the next pulse.

Meanwhile, Realtime Process 2, which begins at 6171, operates simultaneously. The first step in this process at 6172 is to set the clock interrupt to 250 ms so that this process is called every 250 ms. Then the flow continues to 6173 where the process sleeps until the clock interrupt occurs. When the clock interrupt occurs, the interrupt is handled by the Handle Clock Interrupt process. When this process returns, the flow continues to 6172, where the clock interrupt is set again.

Figure 85:
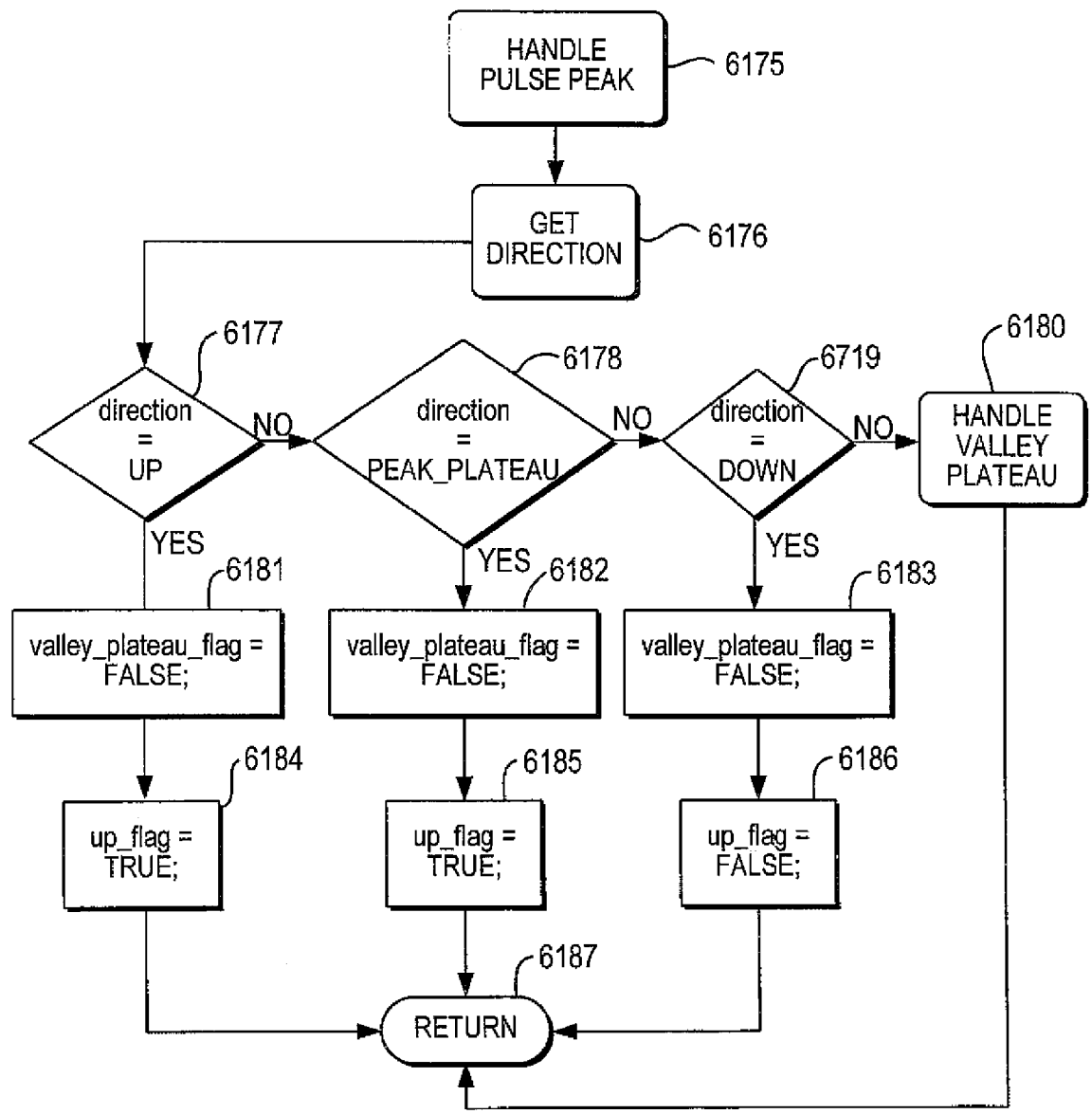

FIG. 85 describes an exemplary Handle Pulse Peak process. In the first step at 6176, the direction is determined by the Get Direction process. (The Get Direction process and related processes have been described in detail above and are thus not repeated here.) After this process returns, the flow continues to 6177.

At 6177 the process checks to see if the direction is UP. If it is then the flow continues to 6181. If it is not, then the flow continues to 6178.

At 6178 the process checks to see if the direction is PEAK_PLATEAU. If it is then the flow continues to 6182. If it is not then the flow continues to 6179.

At 6179 the process checks to see if the direction is DOWN. If it is then the flow continues to 6183. If it is not then the flow continues to 6180.

At 6180 the process Handle VALLEY PLATEAU handles the case where the wave is currently TROUGHING. When this process returns, the flow continues to 6187.

At 6181 the valley plateau flag is set to false. Then the flow continues to 6184, where the up flag is set to true. Then the flow continues to 6187.

At 6182 the valley plateau flag is set to false. Then the flow continues to 6185, where the up flag is set to true. Then the flow continues to 6187.

At 6183 the valley plateau flag is set to false. Then the flow continues to 6186 where the up flag is set to false. Then the flow continues to 6187. At 6187 the Handle Pulse Peak process returns.

Figure 86:
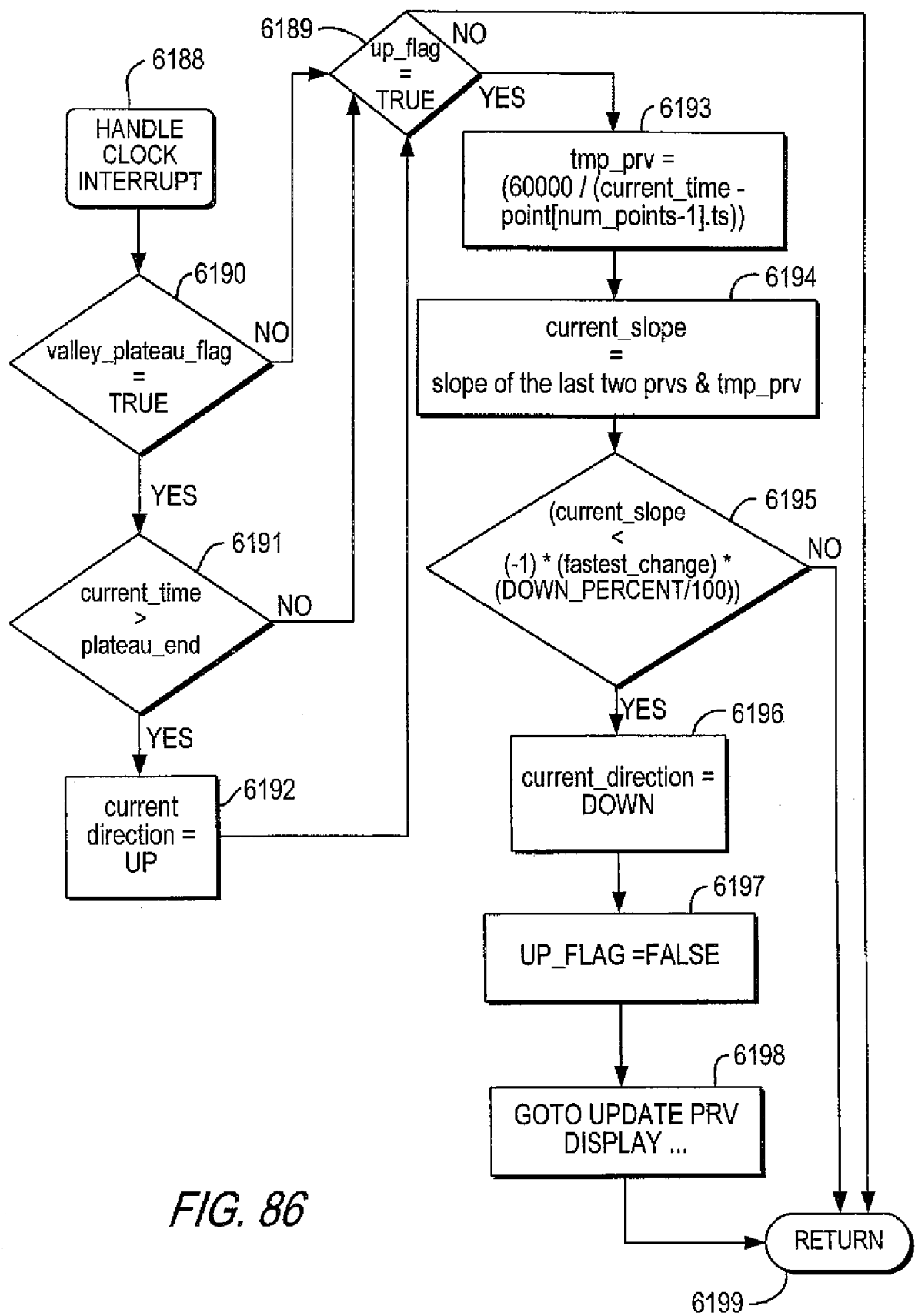

FIG. 86 describes an exemplary Handle Clock Interrupt process. In the first step at 6190 the process checks to see if the valley plateau flag is true. If it is then the flow continues to 6191. If it is not then the flow continues to 6189.

At 6189 the process checks to see if the up flag is true. If it is then the flow continues to 6193. If it is not then the flow continues to 6199.

At 6191 the process checks to see if the current time is past the computed plateau end. If it is, then the flow continues to 6192. If it is not, then the flow continues to 6189.

At 6192 the current direction is recorded as being UP. The UP swing was therefore detected in real-time. Therefore, the completion of the previous wave was detected in real time. Wave delineation, stress metrics, parasympathetic metrics, and the like can therefore be computed, recorded, displayed, and more at this point if desired.

The flow then continues to 6189. At 6189 the process checks to see if the up flag is set to true. If it is, then the flow continues to 6193. If it is not, then the flow continues to 6199.

At 6193 a phantom prv value is computed called tmp_prv. Then the flow continues to 6194 where the current slope is computed based upon the two previous real prv's and the phantom prv. Then the flow continues to 6195.

At 6195 the process checks to see if the current slope is less than −1× DOWN PERCENT% of the fastest change. The computation of fastest change has been described in prior examples. If the current slope is less, then the flow continues to 6196. If it is not less, then the flow continues to 6199.

At 6196 the current direction is recorded as DOWN. In other words, the transition to DOWN was detected in real time. The process did not need to wait for the next pulse beat. The next pulse beat will be occurring after the drop point.

The flow continues to 6197 where the up flag is set to false. Then the flow continues to 6198 where the drop point can be processed. The drop point can be indicated visually, auditorily, or both. After the drop point information is used, the flow continues to 6199. At 6199 the process Handle Clock Interrupt returns.

Figure 87:
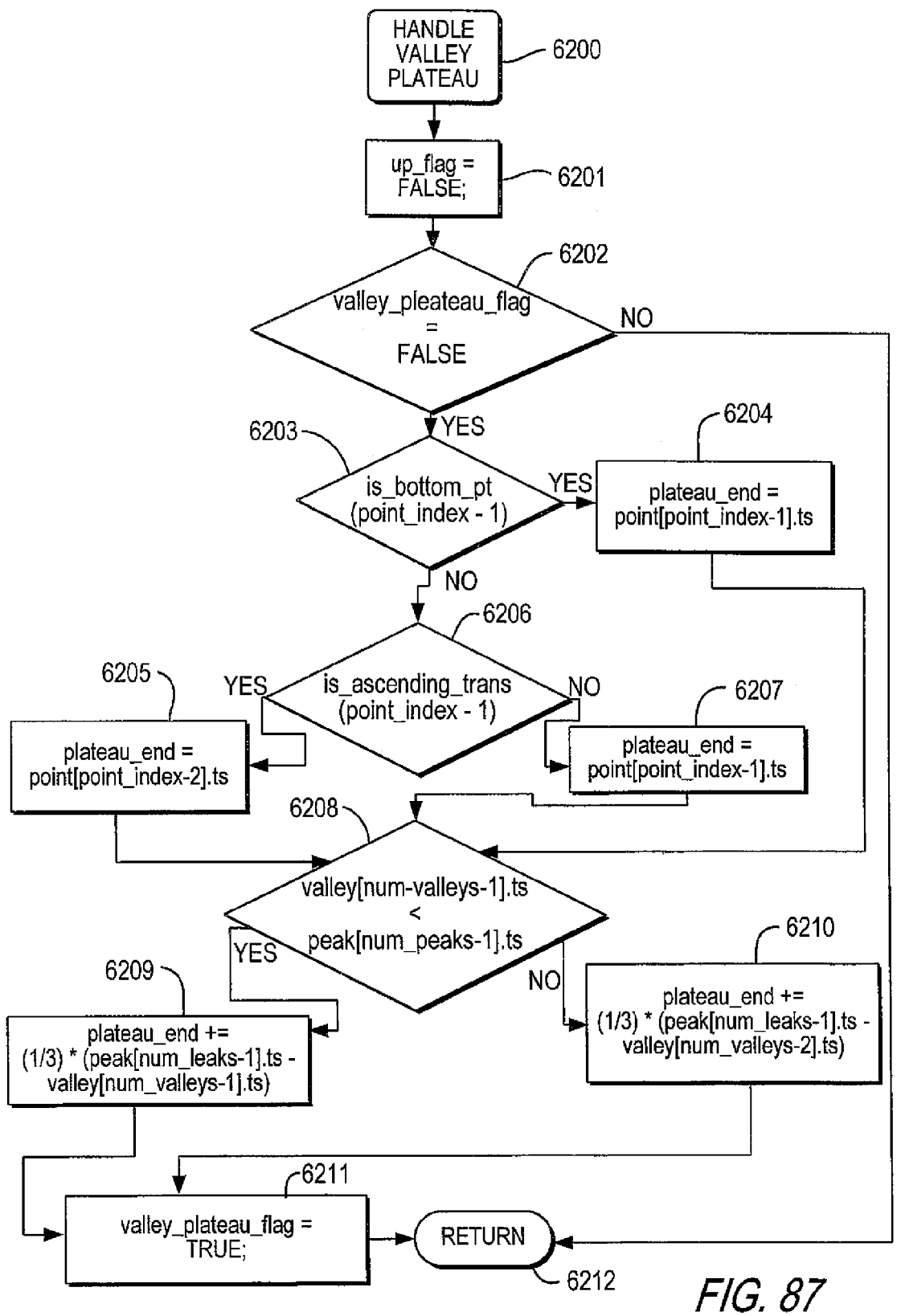

FIG. 87 describes an exemplary Handle VALLEY PLATEAU process. In the first step at 6201, the up flag is set to false. Then the flow continues to 6202.

At 6202 the process checks to see if the valley plateau flag is false. If it is false, then the flow continues to 6203. If it is not false, then the flow continues to 6212.

At 6203 the process checks to see if the previous point is a bottom point. If it is, then the flow continues to 6204. If it is not, then the flow continues to 6206.

At 6204 the timestamp of the previous point is recorded as the plateau end. Then the flow continues to 6208.

At 6206 the process checks to see if the previous point is an ascending transition point. If it is, then the flow continues to 6205. If it is not then the flow continues to 6207.

At 6205 the timestamp of two points ago is recorded as the plateau end. Then the flow continues to 6208.

At 6207 the current point's timestamp is recorded as the plateau end. Then the flow continues to 6208.

At 6208 the process checks to see if the timestamp of the last known valley is less than the timestamp of the last known peak. If it is, then the flow continues to 6209. If it is not, then the flow continues to 6210.

At 6209 one third of the time between the last peak and the last valley is added to the plateau end. Then the flow continues to 6211.

At 6210 one third of the time between the last peak and the second to last valley is added to the plateau end. Then the flow continues to 6211.

At 6211 the valley plateau flag is set to true. Then the flow continues to 6212. At 6212 the process Handle VALLEY PLATEAU returns.

Exemplary procedures for determining, for example, both the drop point and the completion of RSA waves in real time also may be implemented using the following pseudocode corresponding substantially to the flow processes depicted in FIGS. 84-87.

```
// point_index = the index of the last point
<per pp>
switch (direction)
case: UP
    valley_plateau_flag = FALSE;
    up_flag = TRUE;
case: PEAK_PLATEAU
    valley_plateau_flag = FALSE;
```

```
            up_flag = TRUE;
    case: DOWN
            valley_plateau_flag = FALSE;
            up_flag = FALSE;
    case: VALLEY_PLATEAU
    up_flag = FALSE;
    if (!valley_plateau_flag)
            {
                if (is_bottom_pt (point_index – 1)) then
                        plateau_end = point[point_index-1].ts    //use the middle point
                    else if (is_ascending_trans (point_index – 1)) then plateau_start =
    point[point_index-2].ts                                     //use the first point
                if (valley[num-valleys-1].ts < peak[num_peaks-1].ts) then
                        plateau_end += (1/3) * (peak[num_peaks-1].ts – valley[num_valleys-1].ts)
                                // last peak – last valley before the peak
                    else
                        plateau_end += (1/3) * (peak[num_leaks-1].ts – valley[num_valleys-2].ts)
                valley_plateau_flag = TRUE;
            }
    <every 250ms>
    if (valley_plateau_flag) then
    {
        if (current_time > plateau_end) then current_direction = UP
    }
    if (up_flag) then
    {
        tmp_prv = (60000 / (current_time – point[num_points-1].ts))
        current_slope = slope of the last two point prvs & tmp_prv
        if (current_slope < (–1) * (fastest_change) * (DOWN_PERCENT/100)) then
            {
                current_direction = DOWN
                up_flag =false
                goto update prv display ...
            }
    }
}
```

The present invention has been described with reference to particular embodiments. It should be noted, however, that variations and modifications may be made without departing from the spirit and scope of the invention. In particular, it should be appreciated that the various flow processess described herein may be modified to provide substantially equivalent functional implementations and as such are understood to be within the spirit and scope of the invention.

The invention claimed is:

1. A handheld, portable biofeedback device for reducing stress in a human subject comprising:
   a housing;
   a photoplethysmograph (PPG) sensor, wherein the PPG sensor generates data from the human subject;
   a control system coupled to the PPG sensor; and
   a display screen,
   wherein the control system is configured to process data from the human subject for output to the display screen, wherein the output data provides the human subject with information associated with a drop point of at least one respiratory sinus arrhythmia (RSA) wave using phase changes of the RSA wave to detect the drop point, wherein a current phase change of a current portion of the RSA wave is detected by comparing a current phase of the current portion of the RSA wave with a previous phase of a previous portion of the RSA wave.

2. The device of claim 1, wherein the information is visual.

3. The device of claim 1, wherein the information is auditory.

4. The device of claim 1, wherein the information is used to prompt the subject to begin exhalation.

5. The device of claim 1, wherein the information is provided to the subject in substantially real time.

6. The device of claim 1, wherein the device further comprises a breathing metronome capable of being activated by a subject, wherein the breathing metronome is programmed to deactivate after a predetermined period of time.

7. The device of claim 1, wherein the device is configured to extract information related to respiration of a subject.

8. The device of claim 7, wherein the information related to respiration includes rate, rhythm and volume.

9. The device of claim 1, wherein the housing includes a power source.

10. The device of claim 1, wherein power is provided by an A/C source.

11. The device of claim 1, wherein the device functions while grasped between a thumb and a forefinger of the human subject; and wherein the control system is further configured to display on the display screen an error message alerting the human subject to stop squeezing the device and start to relax the thumb when a pressure applied by the thumb on the device exceeds a predetermined value.

12. A method of generating parasympathetic outflow in a subject comprising the act of:
   determining by a device phase changes of at least one respiratory sinus arrhythmia (RSA) wave by comparing a current phase of a current portion of the RSA wave with a previous phase of a previous portion of the RSA wave; and
   providing the subject with information on a drop point of the RSA wave using the phase changes of the RSA wave to detect the drop point.

13. The method of claim 12, wherein the information is visual.

14. The method of claim 12, wherein the information is auditory.

15. The method of claim 12, wherein the information is used to prompt the subject to begin exhalation.

16. The method of claim 12, wherein the information is provided to the subject in substantially real time.

17. The method of claim 12, further comprising the acts of:

grasping the device between a thumb and a forefinger of the subject; and displaying on a display screen of the device an error message alerting the subject to stop squeezing the device and start to relax the thumb when a pressure applied by the thumb on the device exceeds a predetermined value.

* * * * *